(12) United States Patent
Lee et al.

(10) Patent No.: US 8,177,836 B2
(45) Date of Patent: May 15, 2012

(54) APPARATUS AND METHODS FOR MINIMALLY INVASIVE VALVE REPAIR

(75) Inventors: Anthony Lee, San Francisco, CA (US); Jasper Jackson, Newark, CA (US); Liem Ho, Mountain View, CA (US)

(73) Assignee: Medtronic, Inc., Minneapolis, MN (US)

( * ) Notice: Subject to any disclaimer, the term of this patent is extended or adjusted under 35 U.S.C. 154(b) by 397 days.

(21) Appl. No.: 12/401,183

(22) Filed: Mar. 10, 2009

(65) Prior Publication Data

US 2009/0264903 A1 Oct. 22, 2009

Related U.S. Application Data

(60) Provisional application No. 61/035,245, filed on Mar. 10, 2008.

(51) Int. Cl.
*A61F 2/24* (2006.01)
(52) U.S. Cl. .................................................. 623/2.11
(58) Field of Classification Search .................. 606/108, 606/139–142, 158, 198, 200, 213, 75, 116, 606/219, 151; 128/831, 834; 600/426; 623/23.72, 623/23.74, 2.11; 411/457
See application file for complete search history.

(56) References Cited

U.S. PATENT DOCUMENTS

| | | | |
|---|---|---|---|
| 43,098 A | 6/1864 | Cooper |
| 636,728 A | 11/1899 | Kindel |
| 655,190 A | 8/1900 | Bramson |
| 1,087,186 A | 2/1914 | Scholfield |
| 1,167,014 A | 1/1916 | O'Brien |
| 1,539,221 A | 5/1925 | John |
| 1,583,271 A | 5/1926 | Biro |
| 1,625,602 A | 4/1927 | Gould et al. |
| 1,867,624 A | 7/1932 | Hoffman |
| 2,201,610 A | 5/1940 | Dawson |
| 2,240,330 A | 4/1941 | Flagg et al. |
| 2,256,382 A | 9/1941 | Dole |
| 2,264,679 A | 12/1941 | Ravel |
| 2,413,142 A | 12/1946 | Jones et al. |
| 2,430,293 A | 11/1947 | Howells |

(Continued)

FOREIGN PATENT DOCUMENTS

DE 0219999 3/1910

(Continued)

OTHER PUBLICATIONS

"VCS Clip Applier System," published in 1995 by Auto Suture Company, a Division of U.S. Surgical Corporation (8 pages).

(Continued)

*Primary Examiner* — Melanie Tyson
*Assistant Examiner* — Son Dang

(57) ABSTRACT

A surgical fastening apparatus including at least one self-closing clip and a deployment device. The self-closing clip comprises a wire defining an intermediate portion interconnecting opposing, first and second side portions having a memory set loop shape. The deployment device includes a clip holding assembly and an actuator. The clip holding assembly includes first and second containment arms and a transfer rod. The containment arms have a distal segment defining a lumen extending from an open, distal end. The transfer rod is associated with at least one of the containment arms in an axially movable fashion and forms an engagement feature. The actuator is connected to the transfer rod for controlling movement of the rod. Upon final assembly in a pre-deployment state, the engagement feature of the transfer rod engages the intermediate portion of the clip, and the side portions are captured by the containment arms.

19 Claims, 34 Drawing Sheets

U.S. PATENT DOCUMENTS

| | | | |
|---|---|---|---|
| 2,505,358 A | 4/1950 | Gusberg et al. |
| 2,516,710 A | 7/1950 | Mascolo |
| 2,715,486 A | 8/1955 | Marcoff-Moghadam |
| 2,890,519 A | 6/1959 | Storz, Jr. |
| 2,940,452 A | 6/1960 | Smialowski |
| 3,055,689 A | 9/1962 | Jorgensen |
| 3,057,355 A | 10/1962 | Smialowski |
| 3,082,426 A | 3/1963 | Miles |
| 3,143,742 A | 8/1964 | Cromie |
| 3,150,379 A | 9/1964 | Brown |
| 3,180,337 A | 4/1965 | Smialowski |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| 3,656,185 A | 4/1972 | Carpentier |
| RE27,391 E | 6/1972 | Merser |
| 3,753,438 A | 8/1973 | Wood et al. |
| 3,776,237 A | 12/1973 | Hill et al. |
| 3,802,438 A | 4/1974 | Wolvek |
| 3,825,009 A | 7/1974 | Williams |
| 3,837,345 A | 9/1974 | Matar |
| 3,874,388 A | 4/1975 | King et al. |
| 3,875,648 A | 4/1975 | Bone |
| 3,905,403 A | 9/1975 | Smith et al. |
| 3,908,662 A | 9/1975 | Razgulov et al. |
| 3,910,281 A | 10/1975 | Kletschka et al. |
| 3,958,576 A | 5/1976 | Komiya |
| 3,976,079 A | 8/1976 | Samuels |
| 3,995,619 A | 12/1976 | Glatzer |
| 4,006,747 A | 2/1977 | Kronenthal et al. |
| 4,018,228 A | 4/1977 | Goosen |
| 4,038,725 A | 8/1977 | Keefe |
| 4,042,979 A | 8/1977 | Angell |
| 4,073,179 A | 2/1978 | Hickey et al. |
| 4,103,690 A | 8/1978 | Harris |
| 4,111,206 A | 9/1978 | Vishnevsky et al. |
| 4,129,059 A | 12/1978 | Van Eck |
| 4,140,125 A | 2/1979 | Smith |
| 4,170,990 A | 10/1979 | Baumgart et al. |
| 4,185,636 A | 1/1980 | Gabbay et al. |
| 4,192,315 A | 3/1980 | Hilzinger et al. |
| 4,214,587 A | 7/1980 | Sakura |
| 4,217,902 A | 8/1980 | March |
| 4,243,048 A | 1/1981 | Griffin |
| 4,324,248 A | 4/1982 | Perlin |
| 4,345,601 A | 8/1982 | Fukuda |
| 4,352,358 A | 10/1982 | Angelchik |
| 4,366,819 A | 1/1983 | Kaster |
| 4,396,139 A | 8/1983 | Hall et al. |
| 4,416,266 A | 11/1983 | Baucom |
| 4,456,017 A | 6/1984 | Miles |
| 4,465,071 A | 8/1984 | Samuels et al. |
| 4,470,415 A | 9/1984 | Wozniak |
| 4,470,533 A | 9/1984 | Schuler |
| 4,474,181 A | 10/1984 | Schenck |
| 4,485,816 A | 12/1984 | Krumme |
| 4,492,229 A | 1/1985 | Grunwald |
| 4,522,207 A | 6/1985 | Kleiman et al. |
| 4,523,592 A | 6/1985 | Daniel |
| 4,532,927 A | 8/1985 | Miksza, Jr. |
| 4,535,764 A | 8/1985 | Ebert |
| 4,549,545 A | 10/1985 | Levy |
| 4,553,542 A | 11/1985 | Schenck et al. |
| 4,576,605 A | 3/1986 | Kaidash et al. |
| 4,586,502 A | 5/1986 | Bedi et al. |
| 4,586,503 A | 5/1986 | Kirsch et al. |
| 4,593,693 A | 6/1986 | Schenck |
| 4,595,007 A | 6/1986 | Mericle |
| 4,612,932 A | 9/1986 | Caspar et al. |
| 4,622,970 A | 11/1986 | Wozniak |
| 4,624,255 A | 11/1986 | Schenck et al. |
| 4,637,380 A | 1/1987 | Orejola |
| 4,641,652 A | 2/1987 | Hutterer et al. |
| 4,665,906 A | 5/1987 | Jervis |
| 4,665,917 A | 5/1987 | Clanton et al. |
| 4,683,895 A | 8/1987 | Pohndorf |
| 4,706,362 A | 11/1987 | Strausburg |
| 4,719,917 A | 1/1988 | Barrows et al. |
| 4,719,924 A | 1/1988 | Crittenden et al. |
| 4,730,615 A | 3/1988 | Sutherland et al. |
| 4,732,151 A | 3/1988 | Jones |
| 4,809,695 A | 3/1989 | Gwathmey et al. |
| 4,820,298 A | 4/1989 | Leveen et al. |
| 4,844,318 A | 7/1989 | Kunreuther |
| 4,873,975 A | 10/1989 | Walsh et al. |
| 4,887,601 A * | 12/1989 | Richards ............. 606/219 |
| 4,890,615 A | 1/1990 | Caspari et al. |
| 4,896,668 A | 1/1990 | Popoff et al. |
| 4,899,744 A | 2/1990 | Fujitsuka et al. |
| 4,901,721 A | 2/1990 | Hakki |
| 4,923,461 A | 5/1990 | Caspari et al. |
| 4,924,866 A | 5/1990 | Yoon |
| 4,926,860 A | 5/1990 | Stice et al. |
| 4,929,240 A | 5/1990 | Kirsch et al. |
| 4,930,674 A | 6/1990 | Barak |
| 4,932,955 A | 6/1990 | Merz et al. |
| 4,935,027 A | 6/1990 | Yoon |
| 4,950,015 A | 8/1990 | Nejib et al. |
| 4,950,283 A | 8/1990 | Dzubow et al. |
| 4,950,285 A | 8/1990 | Wilk |
| 4,957,498 A | 9/1990 | Caspari et al. |
| 4,983,176 A | 1/1991 | Cushman et al. |
| 4,990,152 A | 2/1991 | Yoon |
| 4,991,567 A | 2/1991 | McCuen et al. |
| 4,994,069 A | 2/1991 | Ritchart et al. |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,007,920 A | 4/1991 | Torre |
| 5,007,921 A * | 4/1991 | Brown ............. 606/221 |
| 5,011,481 A | 4/1991 | Myers et al. |
| 5,020,713 A | 6/1991 | Kunreuther |
| 5,026,379 A | 6/1991 | Yoon |
| 5,032,127 A | 7/1991 | Frazee et al. |
| 5,035,692 A | 7/1991 | Lyon et al. |
| 5,035,702 A | 7/1991 | Taheri |
| 5,042,707 A | 8/1991 | Taheri |
| 5,047,047 A | 9/1991 | Yoon |
| 5,053,047 A | 10/1991 | Yoon |
| 5,064,431 A | 11/1991 | Gilbertson et al. |
| 5,074,874 A | 12/1991 | Yoon et al. |
| 5,088,692 A | 2/1992 | Weiler |
| 5,100,418 A | 3/1992 | Yoon |
| 5,100,421 A | 3/1992 | Christoudias |
| 5,104,407 A | 4/1992 | Lam et al. |
| 5,119,983 A | 6/1992 | Green et al. |
| 5,123,913 A | 6/1992 | Wilk et al. |
| 5,127,413 A | 7/1992 | Ebert |
| 5,129,913 A | 7/1992 | Ruppert |
| 5,152,769 A | 10/1992 | Baber |
| 5,154,189 A | 10/1992 | Oberlander |
| 5,158,566 A | 10/1992 | Pianetti |
| 5,171,250 A | 12/1992 | Yoon |
| 5,171,252 A | 12/1992 | Friedland |
| 5,174,087 A | 12/1992 | Bruno |
| 5,178,634 A | 1/1993 | Ramos Martinez |
| 5,192,294 A | 3/1993 | Blake, III |
| 5,196,022 A | 3/1993 | Bilweis |
| 5,201,880 A | 4/1993 | Wright et al. |
| 5,207,694 A | 5/1993 | Broomé |
| 5,217,027 A | 6/1993 | Hermens |
| 5,219,358 A | 6/1993 | Bendel et al. |
| 5,221,259 A | 6/1993 | Weldon et al. |
| 5,221,269 A * | 6/1993 | Miller et al. ............. 604/528 |
| 5,222,961 A | 6/1993 | Nakao et al. |
| 5,222,976 A | 6/1993 | Yoon |
| 5,234,447 A | 8/1993 | Kaster et al. |
| 5,236,440 A | 8/1993 | Hlavacek |
| 5,242,456 A | 9/1993 | Nash et al. |
| 5,242,457 A | 9/1993 | Akopov et al. |

| Patent No. | Date | Inventor |
|---|---|---|
| 5,246,443 A | 9/1993 | Mai |
| 5,250,053 A | 10/1993 | Snyder |
| 5,258,011 A | 11/1993 | Drews |
| 5,261,917 A | 11/1993 | Hasson et al. |
| 5,269,783 A | 12/1993 | Sander |
| 5,269,809 A | 12/1993 | Hayhurst et al. |
| 5,282,825 A | 2/1994 | Muck et al. |
| 5,290,289 A | 3/1994 | Sanders et al. |
| 5,304,117 A | 4/1994 | Wilk |
| 5,304,204 A | 4/1994 | Bregen |
| 5,306,296 A | 4/1994 | Wright et al. |
| 5,312,436 A | 5/1994 | Coffey et al. |
| 5,314,468 A | 5/1994 | Ramos Martinez |
| 5,330,503 A | 7/1994 | Yoon |
| 5,334,196 A | 8/1994 | Scott et al. |
| 5,336,233 A | 8/1994 | Chen |
| 5,336,239 A | 8/1994 | Gimpelson |
| 5,346,459 A | 9/1994 | Allen |
| 5,350,420 A | 9/1994 | Cosgrove et al. |
| 5,353,804 A | 10/1994 | Kornberg et al. |
| 5,355,897 A | 10/1994 | Pietrafitta et al. |
| 5,356,424 A | 10/1994 | Buzerak et al. |
| 5,364,406 A | 11/1994 | Sewell |
| 5,366,459 A | 11/1994 | Yoon |
| 5,366,462 A | 11/1994 | Kaster et al. |
| 5,366,479 A | 11/1994 | McGarry et al. |
| 5,374,268 A | 12/1994 | Sander |
| 5,376,096 A | 12/1994 | Foster |
| 5,382,259 A | 1/1995 | Phelps et al. |
| 5,383,904 A | 1/1995 | Totakura et al. |
| 5,387,227 A | 2/1995 | Grice |
| 5,403,331 A | 4/1995 | Chesterfield |
| 5,403,333 A | 4/1995 | Kaster et al. |
| 5,403,338 A | 4/1995 | Milo |
| 5,403,346 A | 4/1995 | Loeser |
| 5,413,584 A | 5/1995 | Schulze |
| 5,417,684 A | 5/1995 | Jackson et al. |
| 5,417,700 A | 5/1995 | Egan |
| 5,423,821 A | 6/1995 | Pasque |
| 5,431,666 A | 7/1995 | Sauer et al. |
| 5,437,680 A | 8/1995 | Yoon |
| 5,437,681 A | 8/1995 | Meade et al. |
| 5,437,685 A | 8/1995 | Blasnik |
| 5,439,479 A | 8/1995 | Shichman et al. |
| 5,445,167 A | 8/1995 | Yoon et al. |
| 5,445,644 A | 8/1995 | Pietrafitta et al. |
| 5,450,860 A | 9/1995 | O'Connor |
| 5,451,231 A | 9/1995 | Rabenau et al. |
| 5,452,733 A | 9/1995 | Sterman et al. |
| 5,454,834 A | 10/1995 | Boebel et al. |
| 5,456,246 A | 10/1995 | Schmiedling et al. |
| 5,462,561 A | 10/1995 | Voda |
| 5,474,557 A | 12/1995 | Mai |
| 5,480,405 A | 1/1996 | Yoon |
| 5,486,187 A | 1/1996 | Schenck |
| 5,486,197 A | 1/1996 | Le et al. |
| 5,488,958 A | 2/1996 | Topel et al. |
| 5,496,334 A | 3/1996 | Klundt et al. |
| 5,499,990 A | 3/1996 | Schulken et al. |
| 5,500,000 A | 3/1996 | Feagin et al. |
| 5,522,884 A | 6/1996 | Wright |
| 5,527,342 A | 6/1996 | Pietrzak et al. |
| 5,533,236 A | 7/1996 | Tseng |
| 5,538,509 A | 7/1996 | Dunlap et al. |
| 5,545,214 A | 8/1996 | Stevens |
| 5,549,619 A | 8/1996 | Peters et al. |
| 5,556,411 A | 9/1996 | Taoda et al. |
| 5,562,685 A | 10/1996 | Mollenauer et al. |
| 5,569,205 A | 10/1996 | Hart et al. |
| 5,569,274 A | 10/1996 | Rapacki et al. |
| 5,569,301 A | 10/1996 | Granger et al. |
| 5,571,119 A | 11/1996 | Atala |
| 5,571,175 A | 11/1996 | Vanney et al. |
| 5,573,543 A * | 11/1996 | Akopov et al. ............... 606/144 |
| 5,582,616 A | 12/1996 | Bolduc et al. |
| 5,582,619 A | 12/1996 | Ken |
| 5,584,879 A | 12/1996 | Reimold et al. |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,597,378 A | 1/1997 | Jervis |
| 5,601,571 A | 2/1997 | Moss |
| 5,601,572 A | 2/1997 | Middleman et al. |
| 5,601,600 A | 2/1997 | Ton |
| 5,603,718 A | 2/1997 | Xu |
| 5,609,608 A | 3/1997 | Benett et al. |
| 5,628,757 A | 5/1997 | Hasson |
| 5,630,540 A | 5/1997 | Blewett |
| 5,632,752 A | 5/1997 | Buelna |
| 5,632,753 A | 5/1997 | Loeser |
| 5,643,295 A | 7/1997 | Yoon |
| 5,643,305 A | 7/1997 | Al-Tameem |
| 5,645,568 A | 7/1997 | Chervitz et al. |
| 5,653,716 A | 8/1997 | Malo et al. |
| 5,653,718 A | 8/1997 | Yoon |
| 5,658,312 A | 8/1997 | Green et al. |
| 5,660,186 A | 8/1997 | Bachir |
| 5,665,109 A | 9/1997 | Yoon |
| 5,669,918 A | 9/1997 | Balazs et al. |
| 5,676,670 A | 10/1997 | Kim |
| 5,683,417 A | 11/1997 | Cooper |
| 5,690,662 A | 11/1997 | Chiu et al. |
| 5,695,504 A * | 12/1997 | Gifford et al. ............... 606/153 |
| 5,695,505 A | 12/1997 | Yoon |
| 5,697,913 A | 12/1997 | Sierocuk et al. |
| 5,697,943 A | 12/1997 | Sauer et al. |
| 5,700,270 A | 12/1997 | Peyser et al. |
| 5,700,271 A | 12/1997 | Whitfield et al. |
| 5,702,412 A | 12/1997 | Popov et al. |
| 5,707,362 A | 1/1998 | Yoon |
| 5,707,380 A | 1/1998 | Hinchliffe et al. |
| 5,709,693 A | 1/1998 | Taylor |
| 5,709,695 A | 1/1998 | Northrup, III |
| 5,715,987 A | 2/1998 | Kelley et al. |
| 5,720,755 A | 2/1998 | Dakov |
| 5,725,539 A | 3/1998 | Matern |
| 5,725,542 A | 3/1998 | Yoon |
| 5,728,135 A | 3/1998 | Bregen et al. |
| 5,732,872 A | 3/1998 | Bolduc et al. |
| 5,735,290 A | 4/1998 | Sterman et al. |
| 5,746,753 A | 5/1998 | Sullivan et al. |
| 5,755,778 A | 5/1998 | Kleshinski |
| 5,766,189 A | 6/1998 | Matsumo |
| 5,769,870 A | 6/1998 | Salahich et al. |
| 5,779,718 A | 7/1998 | Green et al. |
| 5,782,397 A | 7/1998 | Koukline |
| 5,782,844 A | 7/1998 | Yoon et al. |
| 5,797,920 A | 8/1998 | Kim |
| 5,797,933 A | 8/1998 | Snow et al. |
| 5,797,934 A | 8/1998 | Rygaard |
| 5,797,960 A | 8/1998 | Stevens et al. |
| 5,799,661 A | 9/1998 | Boyd et al. |
| 5,799,857 A | 9/1998 | Robertson et al. |
| 5,810,848 A | 9/1998 | Hayhurst |
| 5,810,851 A | 9/1998 | Yoon |
| 5,810,853 A | 9/1998 | Yoon |
| 5,810,882 A | 9/1998 | Bolduc et al. |
| 5,817,113 A | 10/1998 | Gifford, III et al. |
| 5,820,631 A | 10/1998 | Nobles |
| 5,824,002 A | 10/1998 | Gentelia et al. |
| 5,824,008 A | 10/1998 | Bolduc et al. |
| 5,827,265 A | 10/1998 | Glinsky et al. |
| 5,827,316 A | 10/1998 | Young et al. |
| 5,830,221 A | 11/1998 | Stein et al. |
| 5,830,222 A | 11/1998 | Makower |
| 5,833,698 A | 11/1998 | Hinchliffe et al. |
| 5,849,019 A | 12/1998 | Yoon |
| 5,851,216 A | 12/1998 | Allen |
| 5,855,614 A | 1/1999 | Stevens et al. |
| 5,868,702 A | 2/1999 | Stevens et al. |
| 5,868,763 A | 2/1999 | Spence et al. |
| 5,871,528 A | 2/1999 | Camps et al. |
| 5,879,371 A | 3/1999 | Gardiner et al. |
| 5,881,943 A | 3/1999 | Heck et al. |
| 5,882,340 A | 3/1999 | Yoon |
| 5,891,130 A | 4/1999 | Palermo et al. |
| 5,891,160 A | 4/1999 | Williamson, IV et al. |

| | | | | | | |
|---|---|---|---|---|---|---|
| 5,893,369 | A | 4/1999 | LeMole | 6,183,512 B1 | 2/2001 | Howanec, Jr. et al. |
| 5,893,865 | A | 4/1999 | Swindle et al. | 6,190,373 B1 | 2/2001 | Palermo et al. |
| 5,893,886 | A | 4/1999 | Zegdi et al. | 6,193,733 B1 | 2/2001 | Adams |
| 5,895,394 | A | 4/1999 | Kienzle et al. | 6,193,734 B1 | 2/2001 | Bolduc et al. |
| 5,904,697 | A | 5/1999 | Gifford, III et al. | 6,197,037 B1 | 3/2001 | Hair |
| 5,908,428 | A | 6/1999 | Scirica et al. | 6,217,611 B1 | 4/2001 | Klostermeyer |
| 5,911,352 | A | 6/1999 | Racenet et al. | 6,221,083 B1 | 4/2001 | Mayer |
| 5,919,207 | A | 7/1999 | Taheri | 6,241,738 B1 | 6/2001 | Dereume |
| 5,931,842 | A | 8/1999 | Goldsteen et al. | 6,241,741 B1 | 6/2001 | Duhaylongsod et al. |
| 5,941,434 | A | 8/1999 | Green | 6,248,117 B1 | 6/2001 | Blatter |
| 5,941,442 | A | 8/1999 | Geiste et al. | 6,250,308 B1 | 6/2001 | Cox |
| 5,941,888 | A | 8/1999 | Wallace et al. | 6,254,615 B1 | 7/2001 | Bolduc et al. |
| 5,941,908 | A | 8/1999 | Goldsteen et al. | 6,269,819 B1 | 8/2001 | Oz et al. |
| 5,944,730 | A | 8/1999 | Nobles et al. | 6,280,460 B1 | 8/2001 | Bolduc et al. |
| 5,951,576 | A | 9/1999 | Wakabayashi | 6,283,979 B1 | 9/2001 | Mers Kelly et al. |
| 5,951,600 | A | 9/1999 | Lemelson | 6,283,993 B1 | 9/2001 | Cosgrove et al. |
| 5,954,735 | A | 9/1999 | Rygaard | 6,296,622 B1 | 10/2001 | Kurz et al. |
| 5,957,363 | A | 9/1999 | Heck | 6,296,656 B1 | 10/2001 | Bolduc et al. |
| 5,957,938 | A | 9/1999 | Zhu et al. | 6,306,141 B1 | 10/2001 | Jervis |
| 5,957,940 | A | 9/1999 | Tanner et al. | 6,332,893 B1 | 12/2001 | Mortier et al. |
| 5,961,481 | A | 10/1999 | Sterman et al. | 6,346,074 B1 | 2/2002 | Roth |
| 5,961,539 | A | 10/1999 | Northrup, III et al. | 6,346,112 B2 | 2/2002 | Adams |
| 5,964,772 | A | 10/1999 | Bolduc et al. | 6,350,269 B1 | 2/2002 | Shipp et al. |
| 5,964,782 | A | 10/1999 | Lafontaine et al. | 6,352,543 B1 | 3/2002 | Cole |
| 5,972,024 | A | 10/1999 | Northrup, III et al. | 6,358,258 B1 | 3/2002 | Arcia et al. |
| 5,976,159 | A | 11/1999 | Bolduc et al. | 6,361,559 B1 | 3/2002 | Houser et al. |
| 5,976,161 | A | 11/1999 | Kirsch et al. | 6,368,348 B1 | 4/2002 | Gabbay |
| 5,976,164 | A | 11/1999 | Bencini et al. | 6,371,964 B1 | 4/2002 | Vargas et al. |
| 5,976,178 | A | 11/1999 | Goldsteen et al. | 6,387,105 B1 | 5/2002 | Gifford, III et al. |
| 5,984,917 | A | 11/1999 | Fleischman et al. | 6,391,038 B2 | 5/2002 | Vargas et al. |
| 5,984,959 | A | 11/1999 | Robertson et al. | 6,402,764 B1 | 6/2002 | Hendricksen et al. |
| 5,989,242 | A | 11/1999 | Saadat et al. | 6,406,492 B1 | 6/2002 | Lytle |
| 5,989,268 | A | 11/1999 | Pugsley, Jr. et al. | 6,406,493 B1 | 6/2002 | Tu et al. |
| 5,989,276 | A | 11/1999 | Houser et al. | 6,409,739 B1 | 6/2002 | Nobles et al. |
| 5,989,278 | A | 11/1999 | Mueller | 6,409,758 B2 | 6/2002 | Stobie et al. |
| 5,993,468 | A | 11/1999 | Rygaard | 6,416,527 B1 | 7/2002 | Berg et al. |
| 5,997,556 | A | 12/1999 | Tanner | 6,418,597 B1 | 7/2002 | Deschenes et al. |
| 6,001,110 | A | 12/1999 | Adams | 6,419,658 B1 | 7/2002 | Restelli et al. |
| 6,007,544 | A | 12/1999 | Kim | 6,419,681 B1 | 7/2002 | Vargas et al. |
| 6,010,531 | A | 1/2000 | Donlon et al. | 6,419,695 B1 | 7/2002 | Gabbay |
| 6,013,084 | A | 1/2000 | Ken et al. | 6,425,900 B1 | 7/2002 | Knodel et al. |
| 6,022,367 | A | 2/2000 | Sherts | 6,428,550 B1 | 8/2002 | Vargas et al. |
| 6,024,748 | A | 2/2000 | Manzo et al. | 6,428,555 B1 | 8/2002 | Koster, Jr. |
| 6,032,849 | A | 3/2000 | Mastri et al. | 6,451,048 B1 | 9/2002 | Berg et al. |
| 6,033,419 | A | 3/2000 | Hamblin, Jr. et al. | 6,461,320 B1 | 10/2002 | Yencho et al. |
| 6,036,699 | A | 3/2000 | Andreas et al. | 6,475,222 B1 | 11/2002 | Berg et al. |
| 6,036,703 | A | 3/2000 | Evans et al. | 6,478,804 B2 | 11/2002 | Vargas et al. |
| 6,036,710 | A | 3/2000 | McGarry et al. | 6,485,496 B1 | 11/2002 | Suyker et al. |
| 6,042,607 | A | 3/2000 | Williamson, IV et al. | 6,491,707 B2 | 12/2002 | Makower et al. |
| 6,056,751 | A | 5/2000 | Fenton, Jr. | 6,497,671 B2 | 12/2002 | Ferrera et al. |
| 6,063,070 | A | 5/2000 | Eder | 6,497,710 B2 | 12/2002 | Yencho et al. |
| 6,066,148 | A | 5/2000 | Rygaard | 6,514,265 B2 | 2/2003 | Ho et al. |
| 6,074,401 | A | 6/2000 | Gardiner et al. | 6,517,558 B2 | 2/2003 | Gittings et al. |
| 6,074,418 | A | 6/2000 | Buchanan et al. | 6,524,338 B1 | 2/2003 | Gundry |
| 6,077,291 | A | 6/2000 | Das | 6,533,812 B2 | 3/2003 | Swanson et al. |
| 6,080,114 | A | 6/2000 | Russin | 6,537,288 B2 | 3/2003 | Vargas et al. |
| 6,083,237 | A | 7/2000 | Huitema et al. | 6,547,799 B2 | 4/2003 | Hess et al. |
| 6,106,538 | A | 8/2000 | Shiber | 6,551,332 B1 | 4/2003 | Nguyen et al. |
| 6,110,188 | A | 8/2000 | Narciso | 6,562,053 B2 | 5/2003 | Schulze et al. |
| 6,113,611 | A | 9/2000 | Allen et al. | 6,575,985 B2 | 6/2003 | Knight et al. |
| 6,113,612 | A | 9/2000 | Swanson et al. | 6,589,255 B2 | 7/2003 | Schulze et al. |
| 6,120,524 | A | 9/2000 | Taheri | 6,607,541 B1 | 8/2003 | Gardiner et al. |
| 6,132,438 | A | 10/2000 | Fleischman et al. | 6,607,542 B1 | 8/2003 | Wild et al. |
| 6,139,540 | A | 10/2000 | Rost et al. | 6,613,059 B2 | 9/2003 | Schaller et al. |
| 6,143,004 | A | 11/2000 | Davis et al. | 6,629,988 B2 | 10/2003 | Weadock |
| 6,149,658 | A | 11/2000 | Gardiner et al. | 6,635,214 B2 | 10/2003 | Rapacki et al. |
| 6,152,935 | A | 11/2000 | Kammerer et al. | 6,641,593 B1 | 11/2003 | Schaller et al. |
| 6,152,937 | A | 11/2000 | Peterson et al. | 6,648,900 B2 | 11/2003 | Fleischman et al. |
| 6,159,165 | A | 12/2000 | Ferrera et al. | 6,651,670 B2 | 11/2003 | Rapacki et al. |
| 6,159,225 | A | 12/2000 | Makower | 6,651,672 B2 | 11/2003 | Roth |
| 6,165,183 | A | 12/2000 | Kuehn et al. | 6,652,540 B1 | 11/2003 | Cole et al. |
| 6,165,185 | A | 12/2000 | Shennib et al. | 6,652,541 B1 | 11/2003 | Vargas et al. |
| 6,171,320 | B1 | 1/2001 | Monassevitch | 6,660,015 B1 | 12/2003 | Berg et al. |
| 6,171,321 | B1 | 1/2001 | Gifford, III et al. | 6,679,851 B2 * | 1/2004 | Burbank et al. ............... 600/564 |
| 6,176,413 | B1 | 1/2001 | Heck et al. | 6,682,540 B1 | 1/2004 | Sancoff et al. |
| 6,176,864 | B1 | 1/2001 | Chapman | 6,695,859 B1 | 2/2004 | Golden et al. |
| 6,179,840 | B1 | 1/2001 | Bowman | 6,702,826 B2 | 3/2004 | Liddicoat et al. |
| 6,179,848 | B1 | 1/2001 | Solem | 6,709,442 B2 | 3/2004 | Miller et al. |
| 6,179,849 | B1 | 1/2001 | Yencho et al. | 6,712,829 B2 | 3/2004 | Schulze |

| | | |
|---|---|---|
| 6,719,768 B1 | 4/2004 | Cole et al. |
| 6,740,401 B1 | 5/2004 | Yahata et al. |
| 6,743,243 B1 | 6/2004 | Roy et al. |
| 6,749,622 B2 | 6/2004 | McGuckin, Jr. et al. |
| 6,776,782 B2 | 8/2004 | Schulze |
| 6,776,784 B2 | 8/2004 | Ginn |
| 6,776,785 B1 | 8/2004 | Yencho et al. |
| 6,802,847 B1 | 10/2004 | Carson et al. |
| 6,821,286 B1 | 11/2004 | Carranza et al. |
| 6,869,444 B2 | 3/2005 | Gabbay |
| 6,913,607 B2 | 7/2005 | Ainsworth et al. |
| 6,918,917 B1 | 7/2005 | Nguyen et al. |
| 6,918,919 B2 * | 7/2005 | Krag ........................ 606/185 |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,955,679 B1 | 10/2005 | Hendricksen et al. |
| 6,960,221 B2 | 11/2005 | Ho et al. |
| 6,979,337 B2 | 12/2005 | Kato |
| 6,979,338 B1 | 12/2005 | Loshakove et al. |
| 7,022,131 B1 | 4/2006 | Derowe et al. |
| 7,056,330 B2 | 6/2006 | Gayton |
| 7,063,711 B1 | 6/2006 | Loshakove et al. |
| 7,070,618 B2 | 7/2006 | Streeter |
| 7,182,769 B2 | 2/2007 | Ainsworth et al. |
| 7,220,265 B2 * | 5/2007 | Chanduszko et al. ........ 606/139 |
| 7,220,268 B2 | 5/2007 | Blatter |
| 7,556,647 B2 * | 7/2009 | Drews et al. ................. 623/2.11 |
| 7,883,538 B2 * | 2/2011 | To et al. ........................ 623/2.11 |
| 7,954,688 B2 * | 6/2011 | Argentine et al. ......... 227/176.1 |
| 2001/0018592 A1 | 8/2001 | Schaller et al. |
| 2001/0018593 A1 | 8/2001 | Nguyen et al. |
| 2001/0018611 A1 | 8/2001 | Solem et al. |
| 2001/0021856 A1 | 9/2001 | Bolduc et al. |
| 2001/0047181 A1 | 11/2001 | Ho et al. |
| 2002/0010490 A1 | 1/2002 | Schaller et al. |
| 2002/0042623 A1 | 4/2002 | Blatter et al. |
| 2002/0082614 A1 | 6/2002 | Logan et al. |
| 2002/0099395 A1 | 7/2002 | Acampora et al. |
| 2002/0151916 A1 | 10/2002 | Muramatsu et al. |
| 2002/0165561 A1 | 11/2002 | Ainsworth et al. |
| 2002/0173803 A1 | 11/2002 | Ainsworth et al. |
| 2003/0045893 A1 * | 3/2003 | Ginn ........................... 606/151 |
| 2003/0074012 A1 | 4/2003 | Nguyen et al. |
| 2003/0078603 A1 | 4/2003 | Schaller et al. |
| 2003/0083742 A1 | 5/2003 | Spence et al. |
| 2003/0093118 A1 | 5/2003 | Ho et al. |
| 2003/0125755 A1 | 7/2003 | Schaller et al. |
| 2003/0191481 A1 | 10/2003 | Nguyen et al. |
| 2003/0195531 A1 | 10/2003 | Nguyen et al. |
| 2003/0199974 A1 | 10/2003 | Lee et al. |
| 2004/0050393 A1 | 3/2004 | Golden et al. |
| 2004/0068276 A1 | 4/2004 | Golden et al. |
| 2004/0102797 A1 | 5/2004 | Golden et al. |
| 2004/0111099 A1 | 6/2004 | Nguyen et al. |
| 2004/0138685 A1 | 7/2004 | Clague et al. |
| 2004/0176663 A1 | 9/2004 | Edoga |
| 2004/0193259 A1 | 9/2004 | Gabbay |
| 2004/0220593 A1 * | 11/2004 | Greenhalgh ................... 606/151 |
| 2004/0249398 A1 * | 12/2004 | Ginn ........................... 606/151 |
| 2005/0004582 A1 | 1/2005 | Edoga |
| 2005/0021054 A1 | 1/2005 | Ainsworth et al. |
| 2005/0043749 A1 | 2/2005 | Breton et al. |
| 2005/0065601 A1 | 3/2005 | Lee et al. |
| 2005/0070924 A1 | 3/2005 | Schaller et al. |
| 2005/0075659 A1 | 4/2005 | Realyvasquez et al. |
| 2005/0075667 A1 | 4/2005 | Schaller et al. |
| 2005/0080454 A1 | 4/2005 | Drews |
| 2005/0101975 A1 | 5/2005 | Nguyen et al. |
| 2005/0107871 A1 * | 5/2005 | Realyvasquez et al. ..... 623/2.11 |
| 2005/0131429 A1 | 6/2005 | Ho et al. |
| 2005/0267572 A1 | 12/2005 | Schoon et al. |
| 2006/0004389 A1 | 1/2006 | Nguyen et al. |
| 2006/0025784 A1 * | 2/2006 | Starksen et al. ............... 606/151 |
| 2006/0135993 A1 * | 6/2006 | Seguin ........................ 606/219 |
| 2006/0253143 A1 | 11/2006 | Edoga |
| 2006/0271081 A1 | 11/2006 | Realyvasquez |
| 2006/0293701 A1 | 12/2006 | Ainsworth et al. |
| 2007/0010835 A1 | 1/2007 | Breton et al. |
| 2007/0027461 A1 | 2/2007 | Gardiner et al. |
| 2007/0106313 A1 | 5/2007 | Golden et al. |
| 2007/0142848 A1 | 6/2007 | Ainsworth et al. |
| 2008/0045982 A1 * | 2/2008 | To et al. ........................ 606/151 |
| 2010/0262167 A1 * | 10/2010 | Jelich et al. ................... 606/151 |

FOREIGN PATENT DOCUMENTS

| | | |
|---|---|---|
| DE | 0377052 | 6/1923 |
| DE | 2703529 | 1/1977 |
| DE | 3203410 | 5/1981 |
| DE | 3227984 | 2/1984 |
| DE | 3504202 | 8/1985 |
| DE | 4133800 | 10/1991 |
| DE | 4402058 | 4/1995 |
| DE | 19547617 | 9/1997 |
| DE | 19732234 | 1/1999 |
| EP | 0072232 | 2/1983 |
| EP | 0122046 | 10/1984 |
| EP | 0129441 | 12/1984 |
| EP | 0130037 | 1/1985 |
| EP | 0140557 | 5/1985 |
| EP | 0121362 | 9/1987 |
| EP | 0409569 | 1/1991 |
| EP | 0432692 | 6/1991 |
| EP | 0478949 | 8/1991 |
| EP | 0494636 | 7/1992 |
| EP | 0537955 | 4/1993 |
| EP | 0559429 | 9/1993 |
| EP | 0598529 | 5/1994 |
| EP | 0326426 | 12/1994 |
| EP | 0419597 | 12/1994 |
| EP | 0632999 | 1/1995 |
| EP | 0641546 | 3/1995 |
| EP | 0656191 | 6/1995 |
| EP | 0687446 | 12/1995 |
| EP | 0705568 | 4/1996 |
| EP | 0711532 | 5/1996 |
| EP | 0705569 | 10/1996 |
| EP | 0734697 | 10/1996 |
| EP | 0778005 | 6/1997 |
| EP | 0815795 | 1/1998 |
| GB | 2223410 | 4/1990 |
| JP | 07308322 | 11/1995 |
| JP | 08336544 | 12/1996 |
| JP | 10337291 | 12/1998 |
| RU | 2110222 | 5/1998 |
| SU | 577022 | 10/1977 |
| SU | 1186199 | 10/1985 |
| SU | 1456109 | 2/1989 |
| SU | 1560133 | 4/1990 |
| WO | 90/06725 | 6/1990 |
| WO | 90/09149 | 8/1990 |
| WO | 90/14795 | 12/1990 |
| WO | 91/07916 | 6/1991 |
| WO | 91/08708 | 6/1991 |
| WO | 91/17712 | 11/1991 |
| WO | 92/05828 | 4/1992 |
| WO | 92/12676 | 8/1992 |
| WO | 92/22041 | 12/1992 |
| WO | 93/01750 | 2/1993 |
| WO | 94/15535 | 7/1994 |
| WO | 94/15537 | 7/1994 |
| WO | 96/00035 | 1/1996 |
| WO | 96/06565 | 3/1996 |
| WO | 96/38090 | 12/1996 |
| WO | 97/12555 | 4/1997 |
| WO | 97/16122 | 5/1997 |
| WO | 97/27898 | 8/1997 |
| WO | 97/28744 | 8/1997 |
| WO | 97/31575 | 9/1997 |
| WO | 97/32526 | 9/1997 |
| WO | 97/40754 | 11/1997 |
| WO | 97/42881 | 11/1997 |
| WO | 98/19636 | 5/1998 |
| WO | 98/30153 | 7/1998 |
| WO | 98/42262 | 10/1998 |
| WO | 98/48707 | 11/1998 |
| WO | 98/52475 | 11/1998 |
| WO | 99/07294 | 2/1999 |

| | | |
|---|---|---|
| WO | 99/12484 | 3/1999 |
| WO | 99/15088 | 4/1999 |
| WO | 99/37218 | 7/1999 |
| WO | 99/62406 | 12/1999 |
| WO | 99/62408 | 12/1999 |
| WO | 99/62409 | 12/1999 |
| WO | 99/62415 | 12/1999 |
| WO | 99/63910 | 12/1999 |
| WO | 99/65409 | 12/1999 |
| WO | 00/03759 | 1/2000 |
| WO | 00/15144 | 3/2000 |
| WO | 00/59380 | 10/2000 |
| WO | 00/60995 | 10/2000 |
| WO | 00/64381 | 11/2000 |
| WO | 00/74603 | 12/2000 |
| WO | 01/19292 | 3/2001 |
| WO | 01/26557 | 4/2001 |
| WO | 01/26586 | 4/2001 |
| WO | 01/28432 | 4/2001 |
| WO | 01/54618 | 8/2001 |
| WO | 01/74254 | 10/2001 |
| WO | 02/13701 | 2/2002 |
| WO | 02/13702 | 2/2002 |
| WO | 02/30295 | 4/2002 |
| WO | 02/30298 | 4/2002 |
| WO | 02/34143 | 5/2002 |
| WO | 02/080779 | 10/2002 |
| WO | 02/080780 | 10/2002 |
| WO | 02/087425 | 11/2002 |
| WO | 03/053289 | 7/2003 |
| WO | 03/088875 | 10/2003 |
| WO | 2005/011468 | 2/2005 |
| WO | 2005/058170 | 6/2005 |

OTHER PUBLICATIONS

Chitwood Jr., *Mitral Valve Repair: Ischemic*, Mastery of Cardiothoracic Surgery, Lippencott-Raven Publishers, 1998, Chapter 32, pp. 309-321.

Emery, et al., "Suture Techniques for MIDCAB Surgery," Chapter 12 in *Techniques for Minimally Invasive Direct Coronary Artery Bypass (MIDCAB) Surgery*. R.W. Emery ed., Hanley & Belfus, Inc.: Philadelphia, Pa, 1997, pp. 87-91.

Grondin, et al., *Carpentier's Annulus and De Vega's Annuloplasty: The end of the tricuspid challenge*, Nov. 1975, vol. 70, pp. 852-861.

Holper, et al., *Surgery for Tricuspid Insufficiency: Long Term Follow-Up After De Vega Annuloplasty*, Thorac Cardiovasc Surgeon, 41, 1993.

Maisano, et al., *The Double Orifice Technique as a Standardized Approach to Treat Mitral Regurgitation Due to Severe Myxomatous Disease: Surgical Technique*, European Journal of Cardiothoracic Surgery, vol. 17, 2000, 201-205.

Rabago, et al., *The New De Vega Technique in Tricuspid Annuloplasty: Results in 150 patients*, J. Cardiovas Surg. 1980 21 pp. 231-238.

Rivera, et al., *Carpentier's Flexible Ring Versus De Vega's Annuloplasty*, J Thorac Cardiovas Surg, Feb. 1985, 89 pp. 196-203.

Wei, et al., *De Vega's Semicircular Annuloplasty for Tricuspid Valve Regurgitation*, Ann Thorac Surg, 1993, 55: pp. 482-485.

Wylie, et al., Manual of Vascular Surgery, R. H. Egdahl ed. Spring-Verlag: New York, vol. II, 1986, Table of Contents only (6 pages).

Wylie, et al., Manual of Vascular Surgery, Springer-Verlag New York, vol. I, 1980, Table of Contents only (3 pages).

Yun, et al. Mitral Valve Replacement, Mastery of Cardiothoracic Surgery, Lippencott-Raven Publishers, 1998, Chapter 34, pp. 329-341.

International Search Report PCT/US98/00462.
International Search Report PCT/US98/00795.
International Search Report PCT/US98/14211.
International Search Report PCT/US99/12563.
International Search Report PCT/US99/12566.
International Search Report PCT/US00/09092.
International Search Report PCT/US01/10501.
International Search Report PCT/US01/31709.
International Search Report PCT/US01/42653.
International Search Report PCT/US02/10865.
International Search Report PCT/US02/10866.
International Search Report PCT/US02/14261.
International Search Report PCT/US03/12073.
International Preliminary Examination Report PCT/US98/00462.
International Preliminary Examination Report PCT/US98/00795.
International Preliminary Examination Report PCT/US99/12566.
International Preliminary Examination Report PCT/US00/09092.
International Preliminary Examination Report PCT/US01/31709.
International Preliminary Examination Report PCT/US01/42653.
International Preliminary Examination Report PCT/US02/14261.
International Preliminary Examination Report PCT/US02/10865.
International Preliminary Examination Report PCT/US02/10866.
International Preliminary Examination Report PCT/US03/12073.
Written Opinion PCT/US99/12563.
Written Opinion PCT/US99/12566.
Written Opinion PCT/US00/09092.
Written Opinion PCT/US01/10501.
Written Opinion PCT/US01/31709.
Written Opinion PCT/US02/10866.
Written Opinion PCT/US02/14261.
Written Opinion PCT/US03/12073.
International Preliminary Report On Patentability PCT/US2004/023728.
US 6,503,260, 01/2003, Schaller et al. (withdrawn)

* cited by examiner

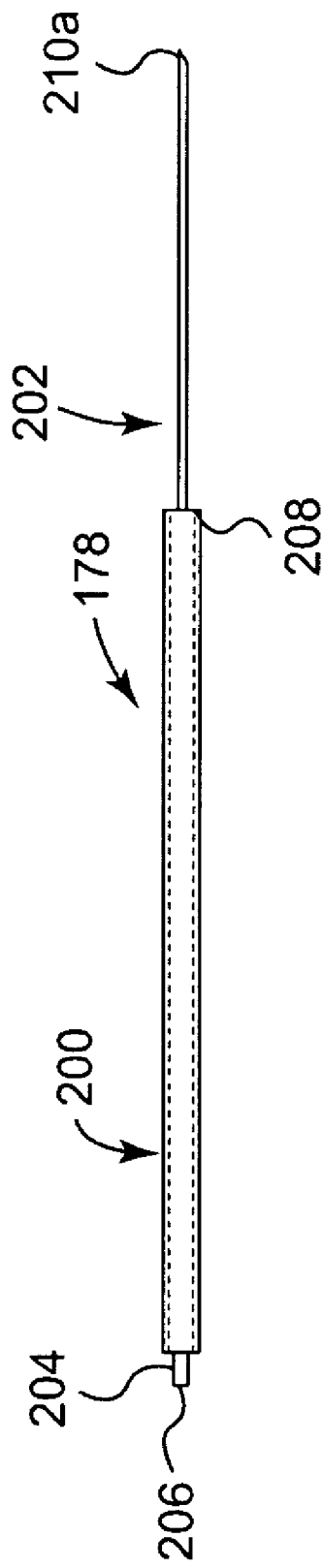
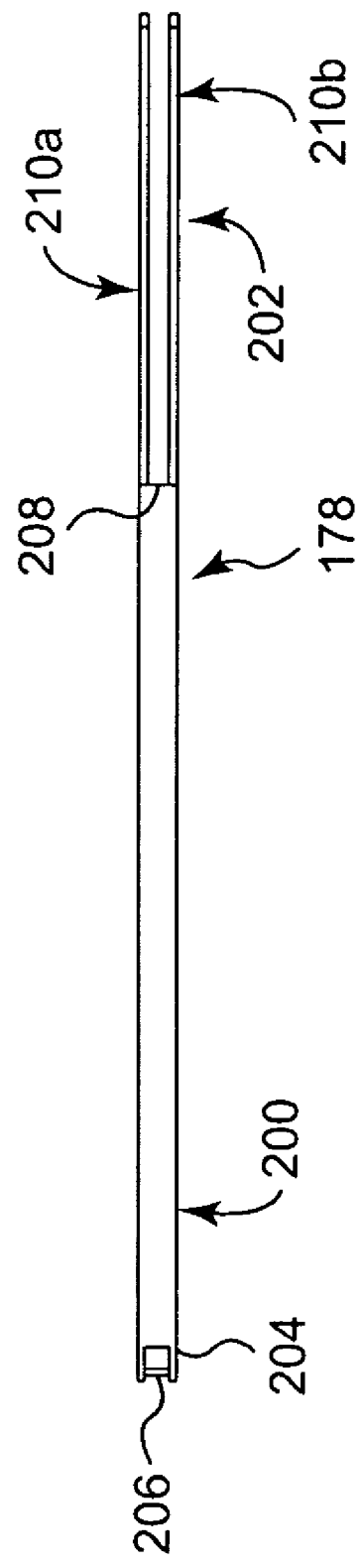
Fig. 17A
Fig. 17B

APPARATUS AND METHODS FOR MINIMALLY INVASIVE VALVE REPAIR

CROSS-REFERENCE TO RELATED APPLICATIONS

This application claims priority under 35 U.S.C. §119(e)(1) to U.S. Provisional Patent Application Ser. No. 61/035,245 filed Mar. 10, 2008, entitled "Apparatus and Methods for Minimally Invasive Valve Repair"; and the entire teachings of which are incorporated herein by reference.

FIELD

The invention relates to apparatus and methods for minimally invasive heart valve replacement and is especially useful in aortic valve repair procedures.

BACKGROUND

Essential to normal heart function are four heart valves, which allow blood to pass through the four chambers of the heart in one direction. The valves have either two or three cusps, flaps, or leaflets, which comprise fibrous tissue that attaches to the walls of the heart. The cusps open when the blood flow is flowing correctly and then close to form a tight seal to prevent backflow.

The four chambers are known as the right and left atria (upper chambers) and right and left ventricles (lower chambers). The four valves that control blood flow are known as the tricuspid, mitral, pulmonary, and aortic valves. In a normally functioning heart, the tricuspid valve allows one-way flow of deoxygenated blood from the right upper chamber (right atrium) to the right lower chamber (right ventricle). When the right ventricle contracts, the pulmonary valve allows one-way blood flow from the right ventricle to the pulmonary artery, which carries the deoxygenated blood to the lungs. The mitral valve, also a one-way valve, allows oxygenated blood, which has returned to the left upper chamber (left atrium), to flow to the left lower chamber (left ventricle). When the left ventricle contracts, the oxygenated blood is pumped through the aortic valve to the aorta.

Certain heart abnormalities result from heart valve defects, such as valvular insufficiency. Valvular insufficiency is a common cardiac abnormality where the valve leaflets do not completely close. This allows regurgitation (i.e., backward leakage of blood at a heart valve). Such regurgitation requires the heart to work harder as it must pump both the regular volume of blood and the blood that has regurgitated. If this insufficiency is not corrected, the added workload can eventually result in heart failure.

Another valve defect or disease, which typically occurs in the aortic valve, is stenosis or calcification. This involves calcium buildup in the valve which impedes proper valve leaflet movement.

In the case of aortic valve insufficiency or stenosis, treatment typically involves removal of the leaflets and replacement with a valve prosthesis. However, known procedures have involved generally complicated approaches that can result in the patient being on cardio-pulmonary bypass for an extended period of time. One procedure used in attaching a replacement aortic valve to the aortic annulus involves sewing the replacement aortic valve to the aorta with sutures. This procedure is time consuming and labor intensive. The surgeon individually places between about 15 and 24 stitches into the aortic valve annulus. Often, access to the valve annulus is tenuous, greatly increasing the difficulty of stitch replacement. After the stitches are placed in the annulus, they are then fed through the replacement valve. The valve is "parachuted" down to the annulus. Finally, the surgeon individually ties each suture. Tying sutures in areas of difficult access runs the risk of suture breakage, tying the suture too tight (potentially damaging tissue), or tying the tissue too loose such that the valve is not properly secured to the valve annulus.

Applicants believe that there remains a need for improved aortic valvular repair apparatus and methods that use minimally invasive techniques and/or reduce time in surgery.

SUMMARY

The present disclosure involves valve repair apparatus and other surgical fastening devices and methods that overcome problems and disadvantages of the prior art.

Some aspects of the present disclosure relate to a surgical fastening apparatus including at least one self-closing clip and a deployment device. The self-closing clip comprises a wire defining an intermediate portion interconnecting opposing, first and second side portions. In this regard, the side portions each have a memory set loop shape. Upon forced transition of the side portions to a more straightened shape, the side portions automatically self-revert to the loop shape. The deployment device includes at least one clip holding assembly and an actuator. The clip holding assembly is provided to selectively retain and deploy the clip, and includes first and second containment arms and a transfer rod. The containment arms are arranged in a side-by-side fashion, and each have a distal segment defining a lumen that extends from an open, distal end. The transfer rod is associated with at least one of the containment arms in an axially movable fashion relative to the longitudinal axis of the containment arm. In this regard, a distal region of the transfer rod forms an engagement feature. Finally, the actuator is connected to the transfer rod for controlling movement of the transfer rod relative to the containment arms. Upon final assembly of the apparatus in a pre-deployment state, the engagement feature of the transfer rod engages the intermediate portion of the clip and the first and second side portions of the clip are captured by the distal segments of the first and second containment arms. The clip can subsequently be deployed from the clip holding assembly by distally moving the transfer rod relative to the containment arms thus distally ejecting the clip from the captured relationship with the containment arms. In some embodiments, two of the transfer rods are provided with the clip holding assembly, slidably disposed within a corresponding one of the containment arms. In other embodiments, a plurality of similarly formed clip holding assemblies are provided, and are circumferentially spaced about the deployment device. With this configuration, a plurality of clips can simultaneously be deployed or ejected from the deployment device. In yet other embodiments, the actuator is rigidly connected to the clip holding assembly; and yet other embodiments, the actuator is remotely associated with the clip holding assembly, such as via flexible tubing.

Yet other aspects of the present disclosure relate to a method of surgically fastening a first body to a second body. The method includes providing a surgical fastening apparatus as described above. The first body is placed into contact with the distal ends of the contact arms. The apparatus is then maneuvered so as to bring the first body into contact with the second body. Finally, the clip is ejected from the clip holding assembly by distally advancing the transfer rod relative to the containment arms. During this ejection step, the first and second side portions of the clip each pass through the first and second bodies so as to fasten the first body to the second body. In some embodiments, the method relates to repair of a heart valve, such that the first body is a replacement valve and the second body is an annulus of a native valve structure.

BRIEF DESCRIPTION OF THE DRAWINGS

FIGS. 17A and 17B illustrate an inner component of the clip deployment assembly useful with the deployment device of FIG. 14;

DETAILED DESCRIPTION

Figure 1A:
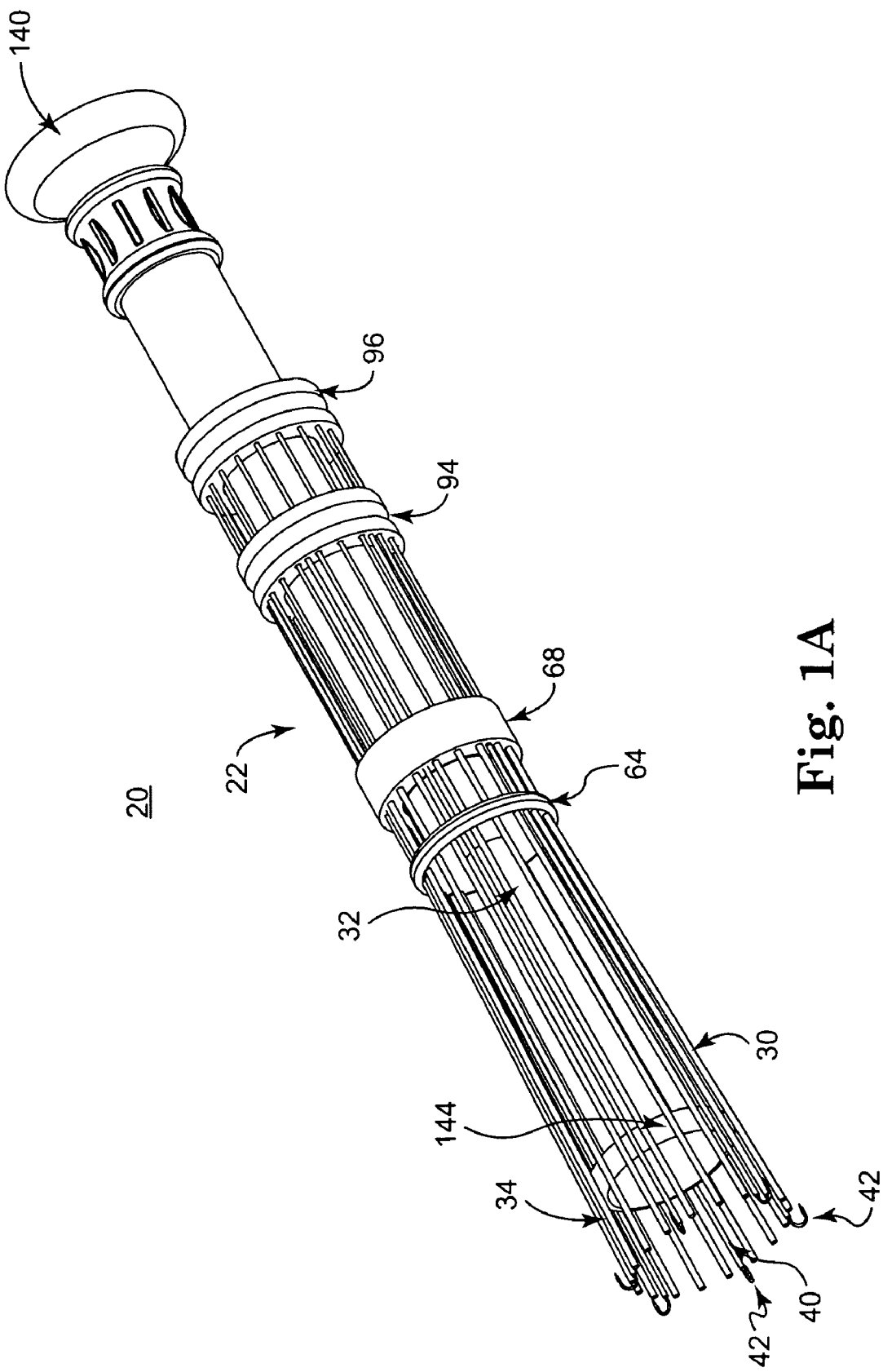
FIG. 1A is a perspective view of a surgical fastening apparatus (e.g., a replacement valve delivery system) constructed according to the principles of the present disclosure and illustrating a deployment device with valve holding mechanisms in an extended state.

This disclosure is not intended to be limited to particular embodiments or examples described, as such may, of course, vary. Further, when referring to the drawings like numerals indicate like elements.

Referring to FIG. 1A, a surgical fastening apparatus according to the present disclosure is shown and generally designated with reference numeral 20.

The apparatus 20 generally comprises a fastener deployment device 22 and a plurality of fasteners 24 (FIG. 9) as described below. The apparatus 20 can be employed as a prosthesis delivery apparatus and also can include one or more prosthesis holding mechanisms. In a further embodiment, the apparatus 20 also includes a prosthesis 26 (FIG. 11) such as a replacement valve, or other body to be surgically fastened which is held to the deployment device 22 through one or more prosthesis holding mechanisms. Thus, the apparatus 20 of the present disclosure can be considered as including, or not including, the body 26 to be surgically fastened.

The apparatus 20 can, for example, enable one to instantaneously attach a replacement aortic valve to the native aortic annulus of a patient. It can be used to implant stentless or stented replacement valves. In the illustrative embodiment, the apparatus 20 secures a prosthetic valve in place using a row of mattress stitches, each of which can be in the form of a self-closing fastener or clip, to reduce or minimize the likelihood of paravalvular leak. Mattress fasteners typically can handle higher pressure than a single stitch and therefore are especially desirable when repairing an aortic valve where pressures are relatively high.

By way of background, to implant a replacement aortic valve using the apparatus 20, the surgeon sets between 6 to 8 guide sutures into the aortic annulus, versus 12-18 sutures set for a normal valve replacement. The sutures are placed through the replacement valve 26 (FIG. 11) and the valve 26 is parachuted down to the annulus. The surgeon then deploys the attachment fasteners or clips 24 (FIG. 9) using the deployment device 22 to secure the valve 26 to the annulus. Among the many advantages of the present disclosure include, but are not limited to, a potential reduction the number of sutures on the order of about 50% as compared to typical procedures, no knots need to be tied, and the risk of tearing tissue is minimized. Further, the device 22 facilitates simultaneous ejection or deployment of all of the clips 24.

Figure 1B:
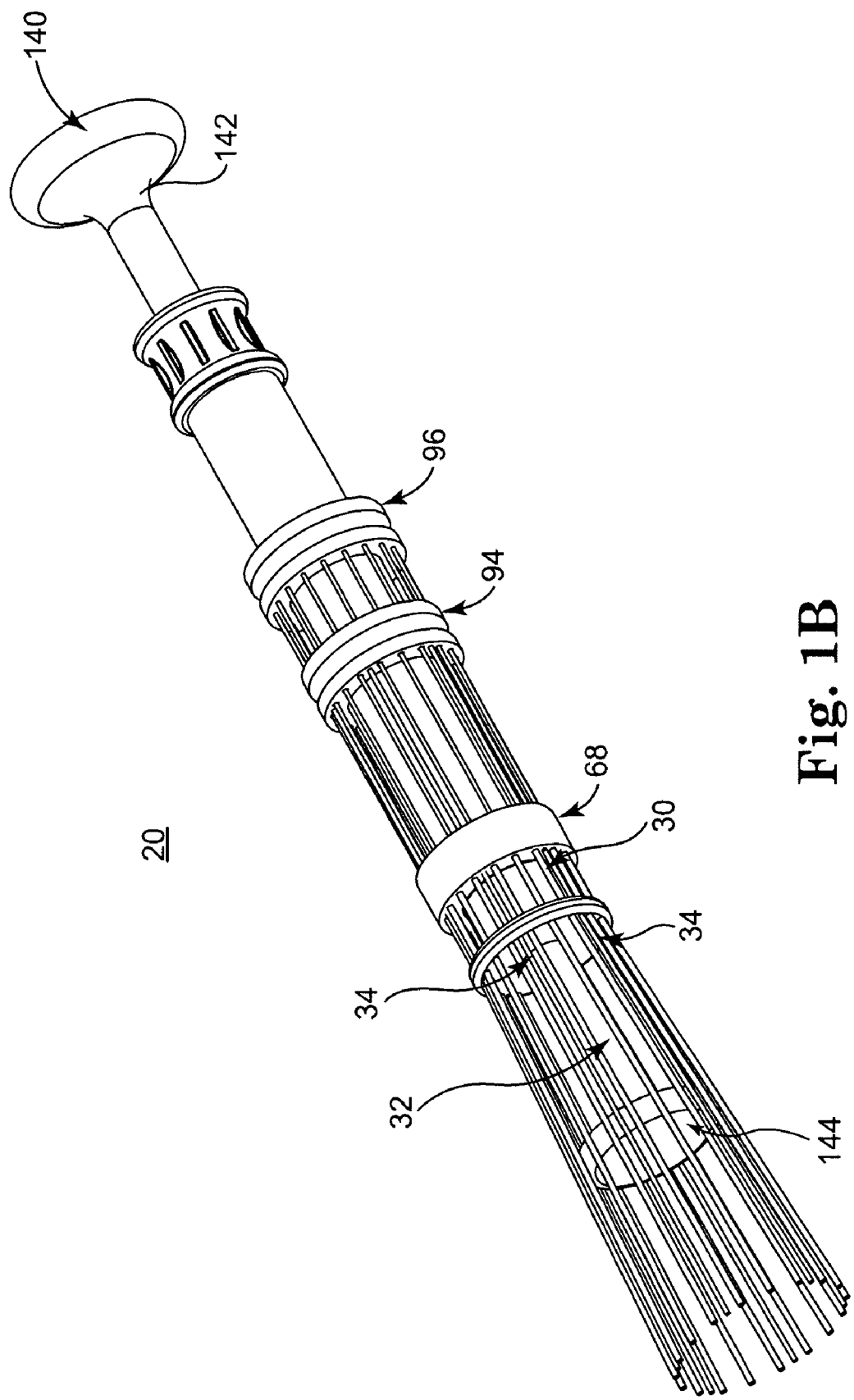
FIG. 1B is a perspective view of the apparatus of FIG. 1A with the valve holding mechanisms in a retracted state.

Referring to FIGS. 1A and 1B, the deployment device 22 comprises a plurality of clip holding assemblies 30, a valve sizing rod 32, and a plurality of valve holding assemblies 34. The attachment clips 24 (FIG. 9) are loaded inside the clip holding assemblies 30 at the distal end portion of the deployment device 22 prior to the procedure. In general terms, the clip holding assemblies 30 and the valve holding assemblies 34 are arranged longitudinally and circumferentially about the device 22. The valve sizing rod 32, in turn, effectuates a desired circumferential spacing of the assemblies 30, 34 at the distal end portion.

Figure 2:
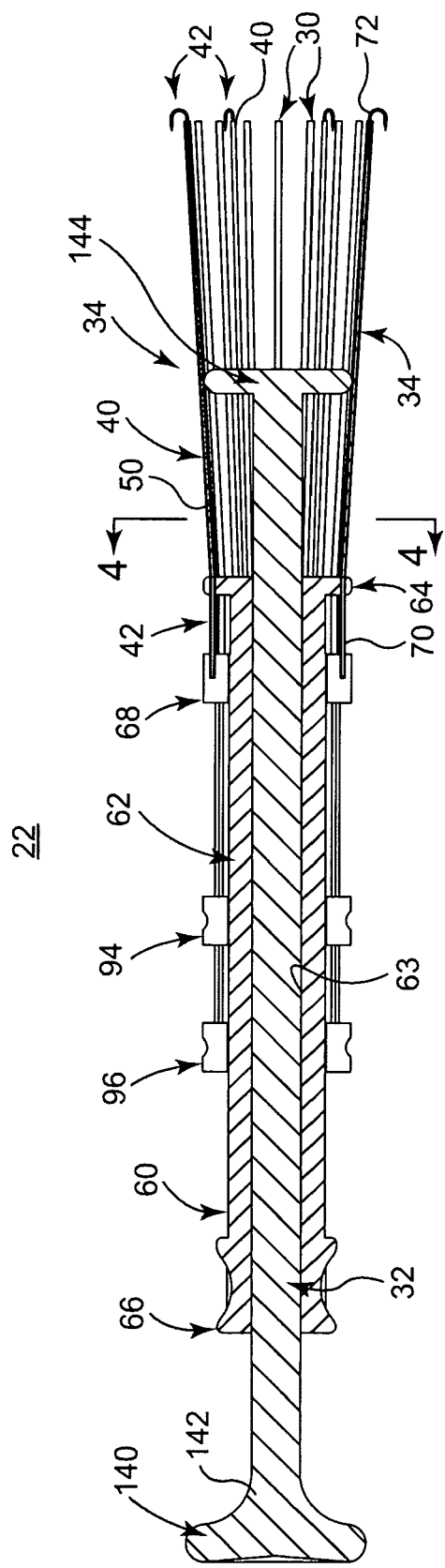
FIG. 2 is a longitudinal, cross-sectional view of the apparatus of FIG. 1B.
Figure 3A:
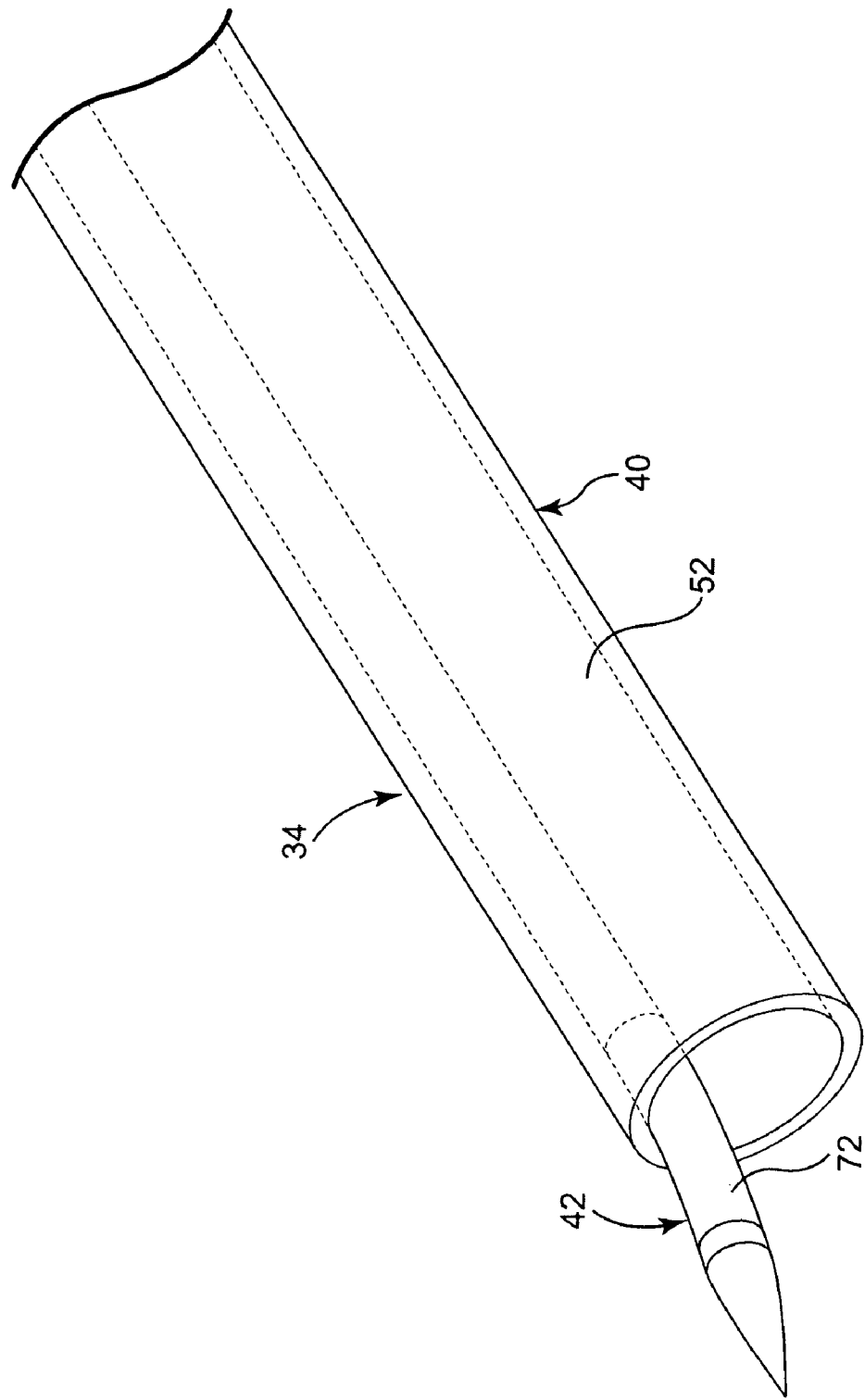
FIG. 3A is an enlarged perspective view of a distal portion of one of the valve holding mechanisms of FIG. 1A.
Figure 3B:
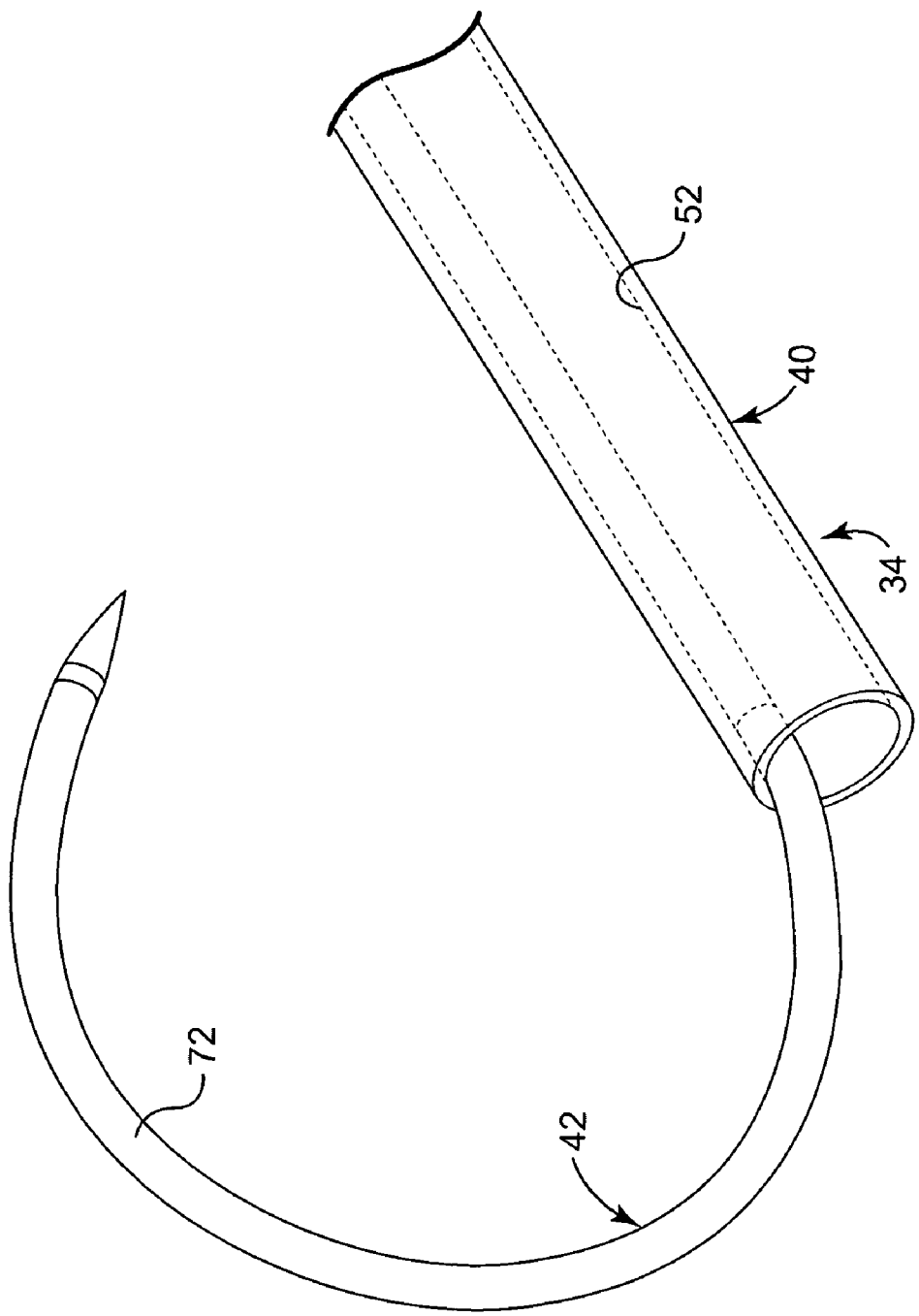
FIG. 3B is an enlarged view of the distal portion of the valve holding mechanism of FIG. 3A and illustrating a holding member in an extended state.

Referring to FIGS. 2, 3A, 3B, and 4, the valve holding assemblies 34 will be described. In the illustrative embodiment, six of the valve holding assemblies 34 (see FIG. 4) are provided, although any other number is also acceptable. The purpose of these assemblies 34 is to hold the valve 26 (FIG. 11) to the deployment device 22 while it is being implanted. After the attachment clips 24 (FIG. 9) are set, the valve holding assemblies 34 are operated to release the valve 26. Each assembly 34 comprises, in some embodiments, a hollow cylinder 40 and a holding member 42. The assemblies 34 are arranged longitudinally and circumferentially around the device 22. The hollow cylinders 40 are held fixed to the deployment device 22 as described below. Respective ones of the holding members 42 are slidably received with a corresponding one of the hollow cylinders 40 and are extendable from the distal end of the respective hollow cylinder 40, and thus from the distal end of the device 22 (as shown in FIG. 3B).

The hollow cylinders 40 are elongated tubes made of a surgically safe, rigid material such as stainless steel, and exhibit sufficient structural integrity to maintain corresponding ones of the holding members 42 in a relatively straight state as described below. In addition, the hollow cylinders 40 are sufficiently resilient to repeatedly deflect in response to operation of the valve sizing rod 32, consistently self-returning to a relatively straight shape. Regardless, the hollow cylinders 40 each define a proximal region 50 and a distal region 52, with the proximal regions 50 being commonly maintained relative to the device 22 via a retractor assembly 60. In some embodiments, and as best shown in FIG. 2, the retractor assembly 60 includes an elongated shaft 62 defining a passage 64 within which the valve sizing rod 32 is slidably received. Further, the retractor assembly 60 includes a base 64 formed at or connected to a distal end of the shaft 62, a grip body 66 formed at or connected to a proximal end of the shaft 62, and a hub 68. The base 64 is configured to rigidly maintain the proximal regions 50 of the hollow cylinders 40 such that the hollow cylinders 40 are circumferentially arranged. Conversely, the clip holding assemblies 30 slidably extend through the base 64. With this configuration, other components of the device 22 (e.g., the clip holding assemblies 30) can be moved relative to the hollow cylinders 40, and vice-versa, by sliding of a corresponding holder component along the shaft 62 as described below.

The holding members 42 are each elongated bodies, extending from a proximal portion 70 to a distal portion 72. The distal portion 72 terminates at a distal end 74 that, in some embodiments, is sharpened (as shown in FIGS. 3A and 3B). Further, at least the distal portion 72 has a shape memory attribute, naturally assuming or self-reverting to a curved shape akin to that shown in FIG. 3B. In some embodiments, the holding member 42 is an integrally formed body, for example a Nitinol® wire provided with a memory set shape that at least partially corresponds to the shape shown in FIG. 3B as is known in the art. Regardless, when retracted into the corresponding hollow cylinder 40, the holding member 42 is readily forced to a relatively straight shape (FIG. 3A).

The holding members 42 are slidably maintained relative to a corresponding one of the hollow cylinders 40 via the hub 68 of the retractor assembly 60. In some embodiments, the hub 68 is a ring slidably disposed over the shaft 62 (as is best shown in FIG. 2). The proximal portion 70 of each of the holding members 42 is affixed to the hub 68 and collectively define a circumferential spacing commensurate with that defined by the hollow cylinders 40 (via the base 64). Thus, the hub 68 positions the holding members 42 to be slidably disposed within respective ones of the hollow cylinders 40. Further, the hub 68 includes apertures 80 (FIG. 6) through which the clip holding assemblies 30 slidably extend such that the hub 68 is slidable over the clip holding assemblies 30 (and vice-versa).

With the above construction, the holding members 42 are held by the hub 68 and thus assembled to the retractor assembly 60. When the hub 68 is pushed distally along the shaft 62, the holding member 42 are extended from the corresponding hollow cylinder 40 (FIG. 3B). When the hub 68 is pulled proximally, the holding members 42 are retracted into the corresponding hollow cylinder 40 (FIG. 3A). When retracted into the hollow cylinder 40, the cylinder 40 straightens the corresponding holding member 42. When extended from the hollow cylinder 40, the holding member 42 assumes its predetermined curved form.

Figure 4:
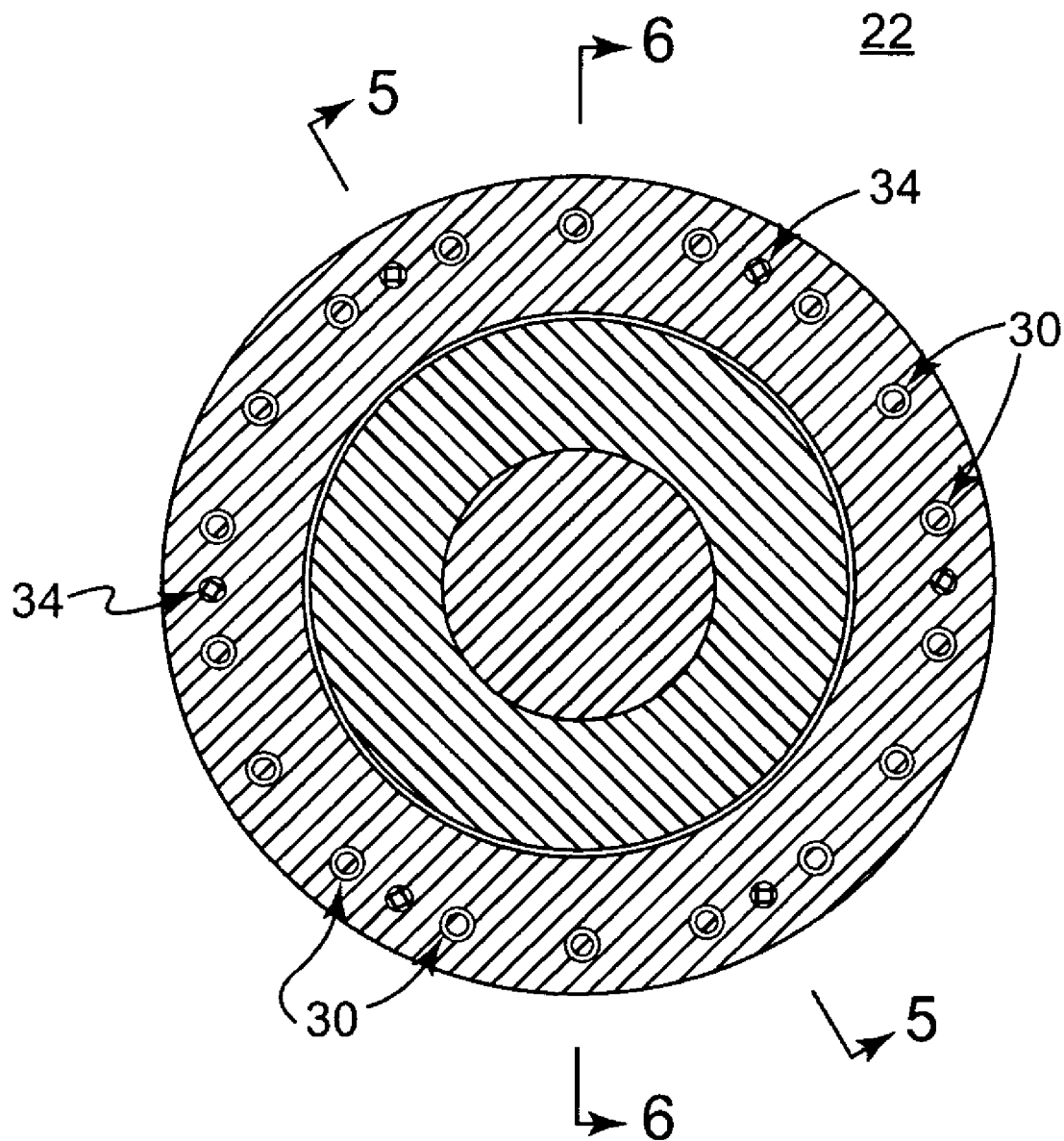
FIG. 4 is a transverse, cross-sectional view of a portion of the apparatus of FIG. 1A taken along line 4-4 in FIG. 2.

Returning to FIGS. 1A and 1B, in some embodiments, there are twelve of the clip holding assemblies 30 (best reflected in FIG. 4). It should be understood that other numbers of the clip holding assemblies 30 can alternatively be provided depending on the application. For example, six or nine of the clip holding assemblies 30 can be used. The clip holding assemblies 30 deploy the attachment clips 24 (FIG. 9) in a manner so as to, for example, affix a replacement aortic valve to an aortic annulus. With additional reference to FIGS. 6 and 9, in some embodiments, each clip holding assembly 30 includes a pair of hollow containment arms 90a, 90b (e.g., hollow piercing members) and a pair of transfer rods 92a, 92b (e.g., clip alignment tubes). As described in greater detail below, simultaneous operation of the clip holding assemblies 30 is dictated by a first control device 94 and a second control device 96.

Figure 9:
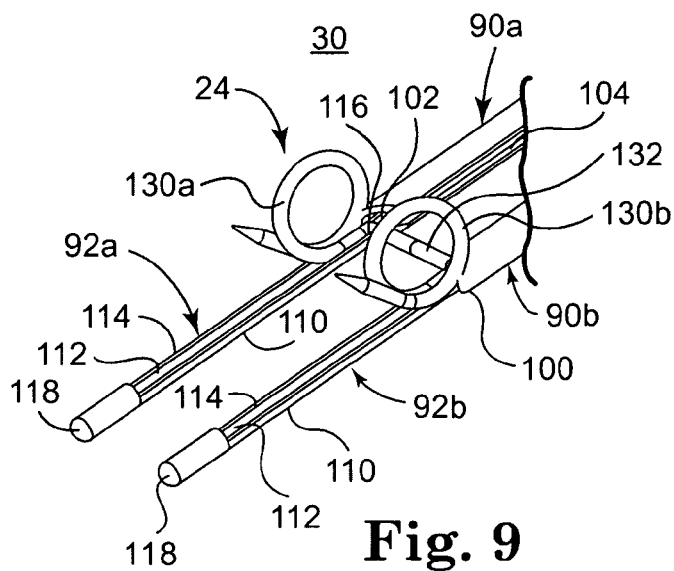
FIG. 9 is an enlarged perspective view of a distal portion of the clip holding assembly of FIG. 7 in a fully deployed state and illustrating a clip or fastener in a natural, memory shape.

With specific reference to FIG. 9 (otherwise showing the clip 24 partially assembled to the clip holding assembly 30), the hollow containment arms 90a, 90b are elongated tubes, each terminating at a distal end 100 that can be sharpened. A lumen 102 (referenced generally) defined by each of the hollow containment arms 90a, 90b is open at the distal end 100, and is sized to slidably receive a portion of the clip 24. With some constructions, the hollow containment arms 90a, 90b forms a side aperture 104 extending from the distal end 100, as described below. Where provided, the slide aperture 104 of the first hollow containment arm 90a "faces" the second hollow containment arm 90b, and vice-versa.

Figure 5:
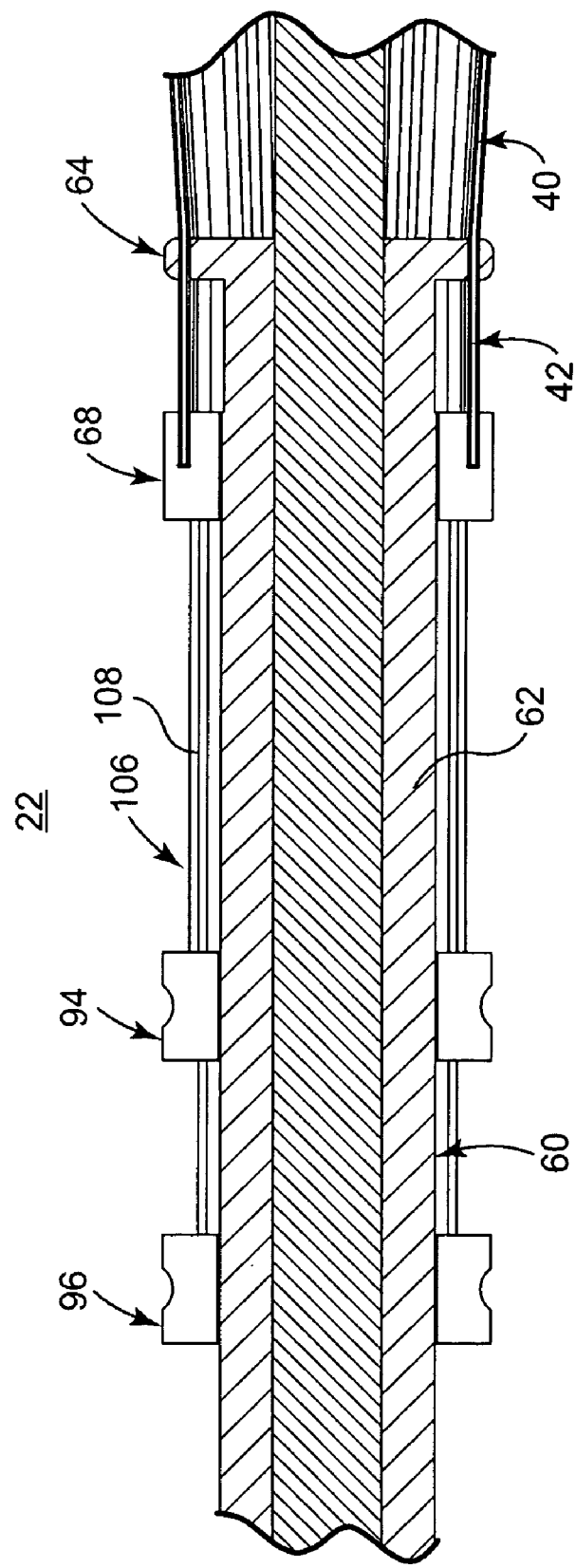
FIG. 5 is a longitudinal, cross-sectional view of a portion of the apparatus of FIG. 1A taken along line 5-5 in FIG. 4.

A lateral spacing between the hollow containment arms 90a, 90b is selected in accordance with a width of the clip 24. Further, the hollow containment arms 90a, 90b are slidable relative to other components of the deployment device 22 (FIG. 1A). For example, in some embodiments, the containment arms 90a, 90b are provided of formed as a distal port of an outer component 106 of the clip holding assembly 30, as best shown with cross-reference to FIG. 5. More particularly, the outer component 106 includes a proximal conduit 108 from which the hollow containment arms 90a, 90b distally extend. With this but one acceptable construction, the proximal conduit 108 is sized to slidably receive a corresponding body associated with the transfer rods 92a, 92b, and is mounted to the first control device 94 (e.g., a ring). Alternatively, the hollow containment arms 90a, 90b can be directly mounted to the first control device 94. Regardless, the first control device 94 is slidably mounted over the shaft 62 of the retractor assembly 60, and the distal ends 100 of the hollow containment arms 90a, 90b float freely. With this configuration, when the first control device 94 is pushed distally, the hollow containment arms 90a, 90b of each of the clip holding assemblies 30 simultaneously move in a distal fashion. When the first control device 94 is pulled proximally, the hollow containment arms 90a, 90b of all of the clip holding assemblies 30 collectively move in a proximal direction.

The transfer rods 92a, 92b are elongated bodies, sized to be slidably received within a respective one of the hollow containment arms 90a, 90b of the corresponding clip holding assembly 30. As best shown in FIG. 9, a distal segment 110 of each of the transfer rods 92a, 92b is configured to releasably maintain a portion of a respective one of the clips 24. More particularly, the distal segment 110 is a tubular body defining a passage 112. The passage 112 serves as part of an engagement feature for selectively retaining a portion of the clip, with the engagement feature further including an axial slot 114 and a radial notch 116. The axial slot 114 is open to the passage 112, and extends from a distal end 118 of the transfer rod 92a and 92b that can otherwise be closed or rounded to minimize traumatic contact with tissue. The radial notch 116 is formed opposite the distal end 118, and is open relative to the passage 112 and the axial slot 114. In this regard, a circumferential width and longitudinal length of the axial slot 114 is commensurate with a diameter and length, respectively, of the clip 24 as described below, such that a portion of the clip 24 can be releasably captured within the passage 112. Similarly, the radial notch 116 is sized in accordance with a diameter of the clip 24 to facilitate loading and subsequent release of the clip 24 relative to the transfer rods 92a, 92b.

The transfer rods 92a, 92b associated with an individual clip holding assembly 30 are configured such that the corresponding radial notches 116 "face" one another. For example, with respect to the representation of FIG. 9, the radial notch 114 of the first transfer rod 92a "faces" the second transfer rod 92b, and the radial notch 114 of the second transfer rod 92b "faces" the first transfer rod 92a.

Figure 6:
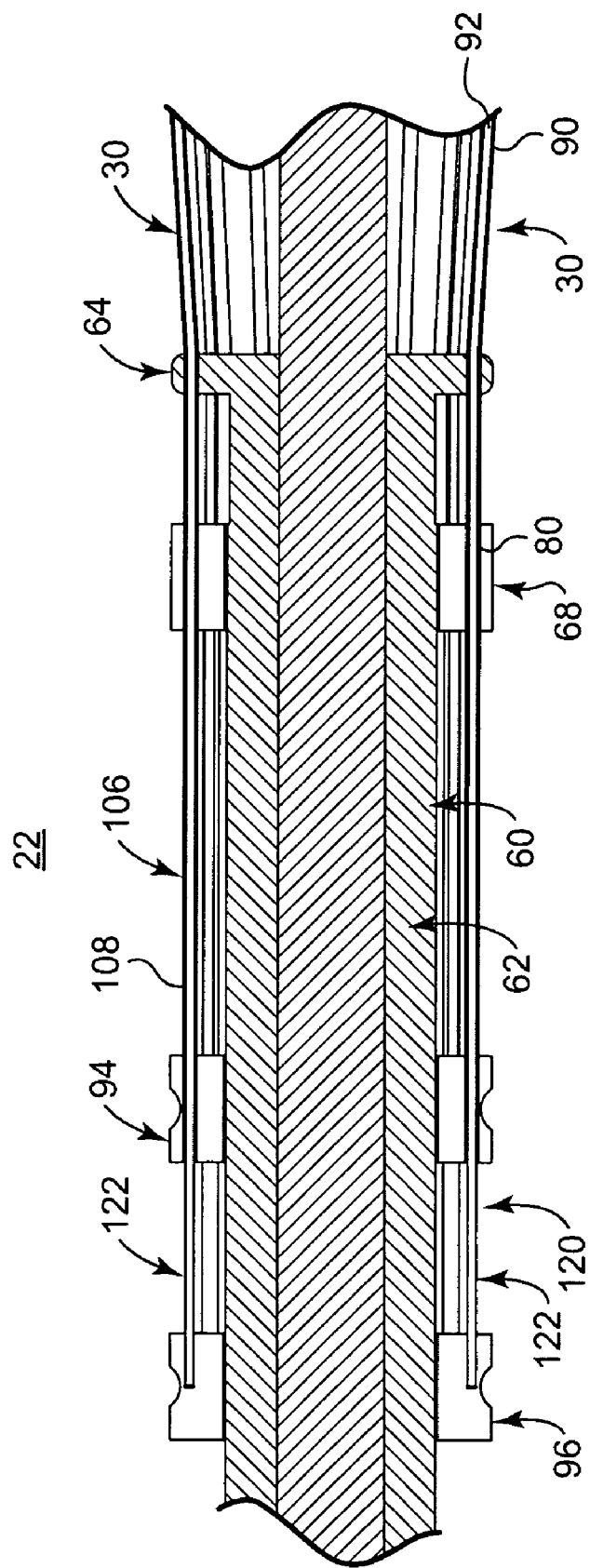
FIG. 6 is a longitudinal, cross-sectional view of a portion of the apparatus of FIG. 1A taken along line 6-6 in FIG. 4.
Figure 7:
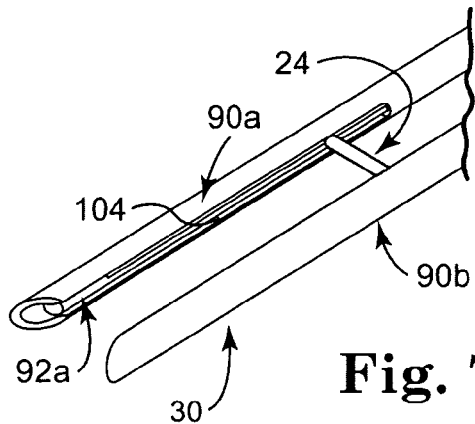
FIG. 7 is an enlarged perspective view of a distal portion of one of a clip holding assemblies of the device of FIG. 1A in a loaded state.

With cross-reference between FIGS. 6 and 9, the transfer rods 92a, 92b (hidden in FIG. 6) of each of the clip holding assemblies 30 are commonly connected to the second control device 96. For example, in some embodiments, the transfer rods 92a, 92b are provided or formed as a distal port of an inner component 120 of the clip holding assembly 30. More particularly, the inner component 120 includes a proximal shaft 122 (FIG. 6) from which the transfer rods 92a, 92b distally extend. With this but one acceptable construction, the proximal shaft 122 is sized to be slidably received within the proximal conduit 108 of the corresponding, inner component 106, with movement of the proximal shaft 122 effectuating a corresponding movement of the transfer rods 92a, 92b. Thus, as shown in FIG. 6, the proximal shafts 122 of each of the clip holding assemblies 30 are commonly mounted to the second control device 96 (e.g., a ring) that in turn is slidably mounted relative to the deployment device 22, such as over the shaft 62 of the retractor assembly 60. Alternatively, all of the transfer rods 92a, 92b can be directly mounted to the second control device 96. Regardless, movement of the second control device 96 effectuates simultaneous movement of the transfer rods 92a, 92b of all the clip holding assemblies 30.

Figure 8:
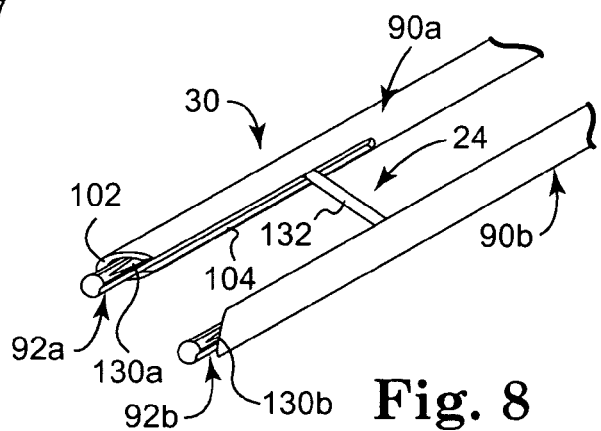
FIG. 8 is an enlarged perspective view of a distal portion of the clip holding assembly of FIG. 7 in a partially extended or deployed state.

With the above construction, the clip holding assembly 30 can be loaded with one of the clips 24 as follows. The clips 24 are described in greater detail below. In general terms, however, in some embodiments each of the clips 24 includes opposing side portions 130a, 130b and an intermediate portion 132. The intermediate portion 132 interconnects the side portions 130a, 130b as shown in FIGS. 8 and 9. Each of the side portions 130a, 130b are transitionable from a natural, loop-like state (FIG. 9) to a straightened state (FIG. 8). With these general parameters in mind and with reference to the clip holding assembly 30 of FIGS. 8 and 9, the clip holding assembly 30 is loaded with the clip 24 by first distally extending the transfer rods 92a, 92b relative to the corresponding hollow containment arms 90a, 90b, for example by distally moving the second control device 96 relative to the first control device 94 (FIG. 6). More particularly, the transfer rods 92a, 92b are positioned such that the corresponding radial notches 116 are distally beyond the distal end 100 of the corresponding hollow containment arms 90a, 90b. The clip 24 is then arranged such that side end portions 130a, 130b pass through the axial slots 114 and into a respective one of the passages 112. The intermediate portion 132 projects through the corresponding radial notches 116, thus extending between the pair of transfer rods 92a, 92b.

The pair of transfer rods 92a, 92b are then proximally retracted relative to the pair of hollow containment arms 90a, 90b (e.g., transitioned from the position of FIG. 9 to the position of FIG. 8 via proximal movement of the second control device 96 (FIG. 6) relative to the first control device 94 (FIG. 6)). With this retraction, the side portions 130a, 130b of the clip 24 move within the lumen 102 and contact the containment arms 90a, 90b, respectively, with this interface forcing the side portions 130a, 130b to a straightened state. The side aperture 104 of the hollow containment arms 90a, 90b facilitate passage of the intermediate portion 132. Conversely, the clip 24 can be released from the clip holding assembly 30 by sliding the transfer rods 92a, 92b distally relative to the hollow containment arms 90a, 90b (e.g., moving the second control device 96 distally relative to the first control device 94).

The attachment clips 24 as described above can be constructed from a single Nitinol wire. The wire can be shape set in the form shown in FIG. 9. Both ends of the side portions 130a, 130b of the wire can be sharpened to allow it to pierce tissue, for example the annular tissue. Thus, the attachment clip 24 can be used to secure a replacement aortic valve to an aortic annulus, for example.

More specifically, the self-closing fasteners or clips 24 can comprise wire made from shape memory alloy or elastic material or wire so that they tend to return to their memory shape after being released from the deployment device 22. As is well known in the art, shape memory material has thermal or stress relieved properties that enable it to return to a memory shape. For example, when stress is applied to shape memory alloy material causing at least a portion of the material to be in its martensitic form, it will retain its new shape until the stress is relieved as described in U.S. Pat. No. 6,514,265 to Ho, et al., entitled "Tissue Connector Apparatus with Cable Release" and U.S. Pat. No. 6,641,593, entitled "Tissue Connector Apparatus and Methods". Then, it returns to its original, memory shape. Accordingly, at least a portion of the shape memory alloy of each clip 24 is converted from its austenitic phase to its martensitic phase when the wire 24 is in its deformed, open configuration inside the relatively straight distal end portion 100 of a respective hollow containment arms 90a, 90b (see e.g., FIG. 8). When the stress is removed and a respective clip 24 unrestrained, the material undergoes a martensitic to austenitic conversion and the clip springs back to its undeformed configuration (FIG. 9).

One suitable shape memory material for the clip 24 is a nickel titanium (Nitinol) based alloy, which exhibits such pseudoelastic (superelastic) behavior. The Nitinol may include additional elements which affect the yield strength of the material or the temperature at which particular pseudoelastic or shape transformation characteristics occur. The transformation temperature may be defined as the temperature at which a shape memory alloy finishes transforming from martensite to austenite upon heating (i.e., $A_f$ temperature). The shape memory alloy preferably exhibits pseudoelastic (superelastic) behavior when deformed at a temperature slightly above its transformation temperature. As the stress is removed, the material undergoes a martensitic to austenitic conversion and springs back to its original undeformed configuration. In order for the pseudoelastic wire to retain sufficient compression force in its undeformed configuration, the wire should not be stressed past its yield point in it deformed configuration to allow complete recovery of the wire to its undeformed configuration. The shape memory alloy is preferably selected with a transformation temperature suitable for use with a stopped heart condition where cold cardioplegia has been injected for temporary paralysis of the heart tissue (e.g., temperatures as low as 9-10 degrees Celsius).

The clip 24 can be made by wrapping a Nitinol wire having a diameter in the range of about 0.003 to 0.015 inch, for example 0.010 inch, and wrapping it around two spaced mandrels. The heat treatment of the Nitinol wire to permanently set its shape as shown in FIG. 9 can be achieved by heat-treating the wire and mandrel in either a convection oven or bath at a temperature range of 400 to 650° C., for example 520° C., for a duration of 1 to 45 minutes, for example 15 minutes. As a point of reference, the holding members 42 can be provided with a set memory shape in the same manner.

The attachment clips 24 generally are formed with a memory set shape that comprises the looped side portions 130a, 130b and the straight, fixed length intermediate portion 132 therebetween. The length of the intermediate portion 132 can vary depending on the application. This configuration provides for a mattress suture-like connection, and the intermediate portion 132 minimizes or eliminates tissue plication. This is especially advantageous in aortic applications where the primary defect is aortic stenosis where dilation is preferred. Under these circumstances, the clip or fastener 24 pulls in a radial direction to seal the connection between the prosthesis and valve annulus.

Returning to FIGS. 1A and 2, the valve sizing rod 32 runs longitudinally through the center of the deployment device 22, and in particular the shaft 62 of the retractor assembly 60. With this arrangement, the valve sizing rod 32 is axially slidable relative to the shaft 62, and thus relative to the clip holding assemblies 30 and the valve holding assemblies 34. A handle 140 can be provided on a proximal end 142 of the rod 32, whereas a radial spacer 144 is formed or provided at a distal end. The valve sizing rod 32, and in particular the spacer 144, is used to spread the distal end of the valve and clip holding assemblies 30, 34 in a radial direction. By spreading the holding assemblies 30, 34, the effective diameter of the circle made by the holding assemblies 30, 34 is increased. This allows the deployment device 22 to fit a wide range of valve sizes.

Figure 10A:
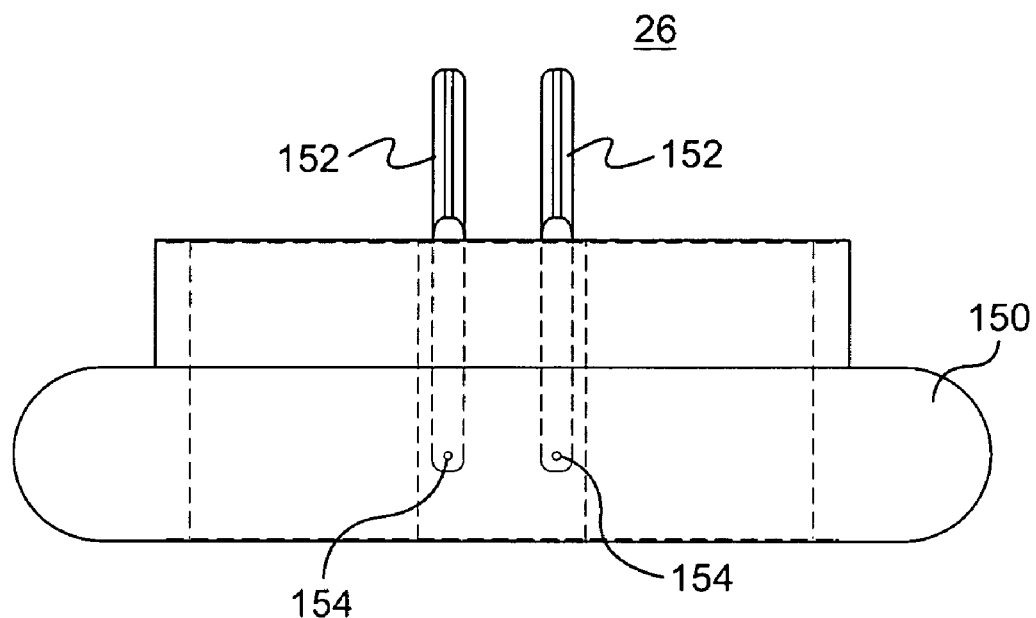
FIG. 10A diagrammatically illustrates a replacement valve in an open state.
Figure 10B:
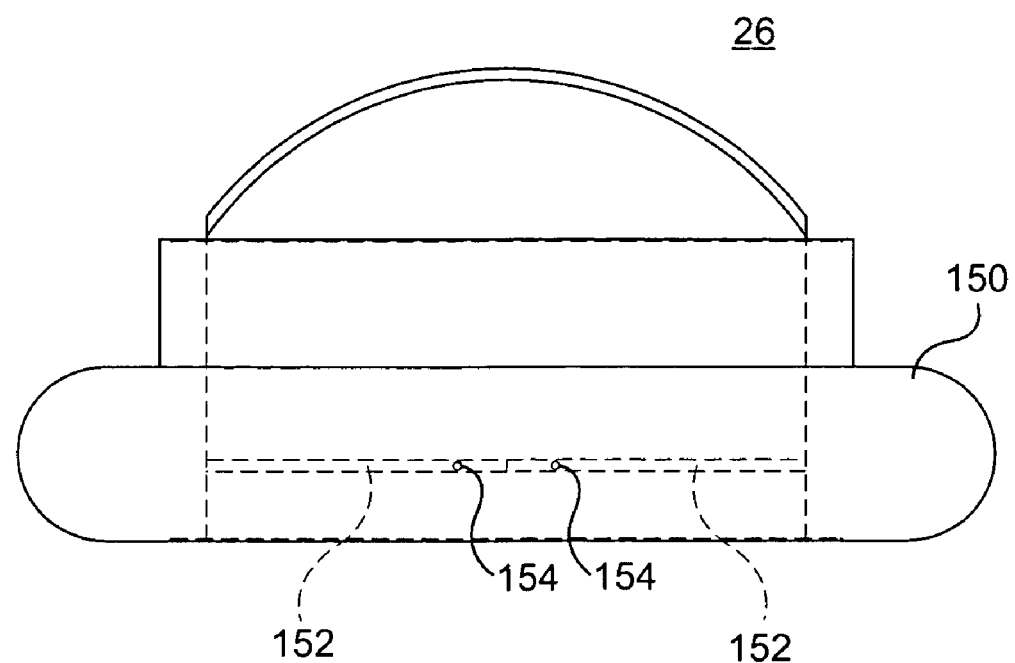
FIG. 10B diagrammatically illustrates the replacement valve of FIG. 10A in a closed state.
Figure 11:
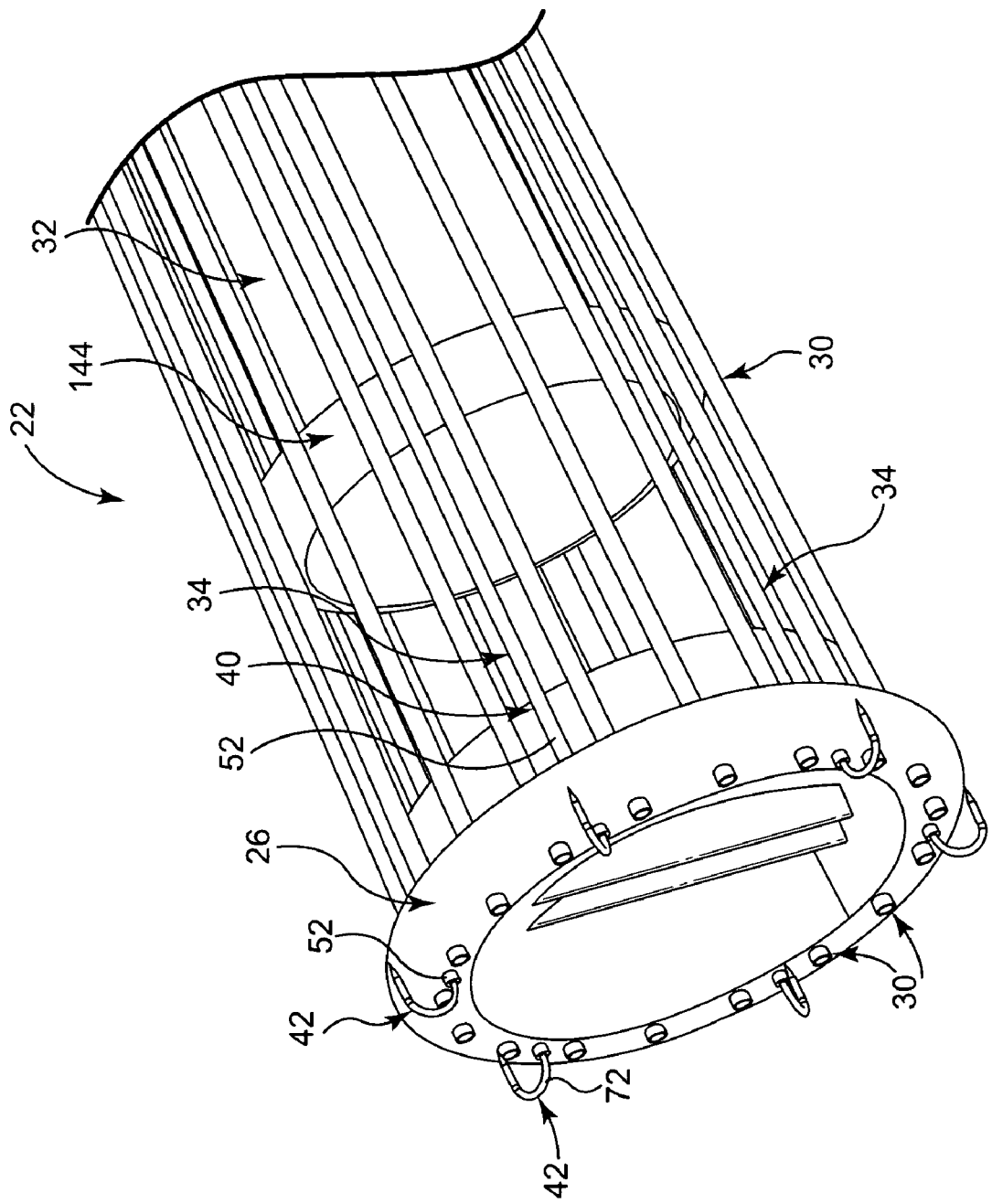
FIG. 11 illustrates the distal end portion of the embodiment of FIG. 1A with the replacement valve of FIGS. 10A and 10B secured thereto with the valve holding mechanisms.

The following example is set forth with reference to various ones of the figures to further illustrate operation of the prosthesis delivery apparatus 20 in replacing a malfunctioning aortic valve with the prosthetic valve 26. It should be understood, however, that this example is not intended to limit a scope of the present disclosure. That is to say, the apparatus 20 can be used to surgically fasten a wide variety of first bodies or structures to second bodies or structures.

Where a prosthetic valve is to be fastened, the replacement valve 26 can assume a variety of forms, including mechanical valves or tissue values. As a point of reference, referring to FIGS. 10A, 10B, and 11, FIG. 10A diagrammatically illustrates a mechanical replacement valve 26 in an open state, whereas FIG. 10B diagrammatically illustrates the replacement valve 26 of FIG. 10A in a closed state. FIG. 11 illustrates the distal end portion of the device 22 of FIG. 1A, with the replacement valve 26 of FIGS. 10A and 10B secured thereto with the valve holding mechanisms 34. In general terms, the mechanical heart valve prosthesis 26 comprises an annular ring or housing 150, which can be metal or carbon material, to which two valve leaflets 152 are pivotably mounted. Each leaflet 152 is pivotably mounted to the ring 150 with two pivots 154 (two of the four pivots being hidden from view in FIG. 10A). A portion of each leaflet 152 extends beyond its respective pivot 154 as shown in FIG. 10A so that the leaflets 152 can fully close the valve opening formed by ring 150 (FIG. 10B). Referring to FIG. 11, the apparatus 20 is shown in combination with the conventional mechanical heart valve prosthesis generally designated with reference numeral 26.

Although a particular mechanical heart valve prosthesis is shown, it should be understood that any suitable mechanical heart valve prosthesis (or other valve prosthesis including a tissue valve prosthesis) can be used without departing from the scope of the present disclosure. For example, a mechanical valve having a ball can be used. Such ball valves also are known in the art.

During an aortic valve replacement procedure in accordance with the present disclosure, first, the existing aortic valve is removed using standard surgical techniques. The native annulus should be debrided of calcium to minimize the risk of having the replacement valve leaking. Then, normal valve sizing procedures are used to determine the proper size of the replacement valve, which is to be placed in the aortic annulus. Each replacement valve (e.g., shown generally at 26 in FIG. 11) may come with its own proprietary sizing techniques. The selected prosthetic valve 26 is then loaded onto the distal end of the device 22 (FIG. 11). The sewing cuff of the valve (for stented valves) or the inflow track of the valve (for stentless valves) is placed in intimate contact with the distal end of the valve holding assemblies 34. More particularly, the valve holding assemblies 34 are arranged such that the holding members 42 are fully retracted within the corresponding hollow cylinders 40, and the valve 26 is placed into contact with the distal region 52 of each of the circumferentially arranged hollow cylinders 40. In this regard, the valve sizing rod 32 can be moved distally or proximally to adjust the effective diameter collectively defined by the distal regions 52 of the hollow cylinders 40 to best fit the valve 26.

The valve holding assemblies 34 are then operated to establish a more robust engagement with the valve 26 via the holding members 42. The hub 68 for the holding members 42 is actuated (e.g., pushed distally), causing the holding members 42 to extend from the corresponding hollow cylinders 40 and into the sewing cuff (stented) or inflow track (stentless) of the valve 26. As they extend from the hollow cylinders 40, the holding members 42 curl back (e.g., the distal portions 72 self-revert to a natural, curved or loop-like state), locking the replacement valve 26 into place (FIG. 11).

The clip holding assemblies 30 are then operated to establish a desired pre-deployment arrangement with the replacement valve 26. The first control device 94 for the hollow containment arms 90a, 90b is pushed distally, causing the hollow containment arms 90a, 90b of all of the clip holding assemblies 30 to collectively move distally toward the valve 26. The hollow containment arms 90a, 90b are allowed to pierce but not extend all the way through the sewing cuff (stented) or inflow track (stentless) of the valve 26.

Guide sutures are then set onto the annulus. Standard surgical sutures can be used to guide the prosthetic valve 26 into the aortic annulus. The surgeon can set these sutures into the annulus of the valve 26. One suture can be set at each commissure and one half way in between each commissure. The surgeon may opt to set more sutures around sensitive areas such as fragile tissue or areas surrounding the conduction system. The guide sutures can then be set through the valve 26. The surgeon desirably lines up the anatomy of the replacement valve 26 with the anatomy of the native valve annulus.

The apparatus 20 is then manipulated to slide the replacement valve 26 down the guide sutures until the replacement valve 26 is in intimate contact with native valve annulus in a parachuting fashion.

The clip holding assemblies 30 can then be further manipulated to ensure desired positioning relative to the valve 26 and the native annulus. For example, the first control device 94 is pushed distally causing the distal end 100 of the all of the hollow containment arms 90a, 90b to extend past the valve sewing cuff or inflow track of the replacement valve 26.

The clip holding assemblies 30 are then operated to deploy the clips 24 (otherwise previously loaded to the device 22 as described above). For example, the second control device 96 is pushed distally, causing the transfer rods 92a, 92b of all the clip holding assemblies 30 to simultaneously extend distally beyond the corresponding hollow containment arms 90a, 90b. This, in turn, allows the clips 24 to deploy as described above. In this regard, all of the clips 24 can be substantially simultaneously deployed or released from the clip holding assemblies 30 with distal movement of the second control device 96.

The valve holding assemblies 34 are then disengaged from the replacement valve 26. For example, the hub 68 of the retractor assembly 60 is pulled proximally, retracting the holding members 42 into the hollow cylinders 40. The valve 26 is now no longer being held to the deployment device 22. The deployment device 22 can then be removed from the surgical site.

The guide sutures are also removed. For example, the guide sutures can be cut at one end and pulled out of the annulus.

Figure 12:
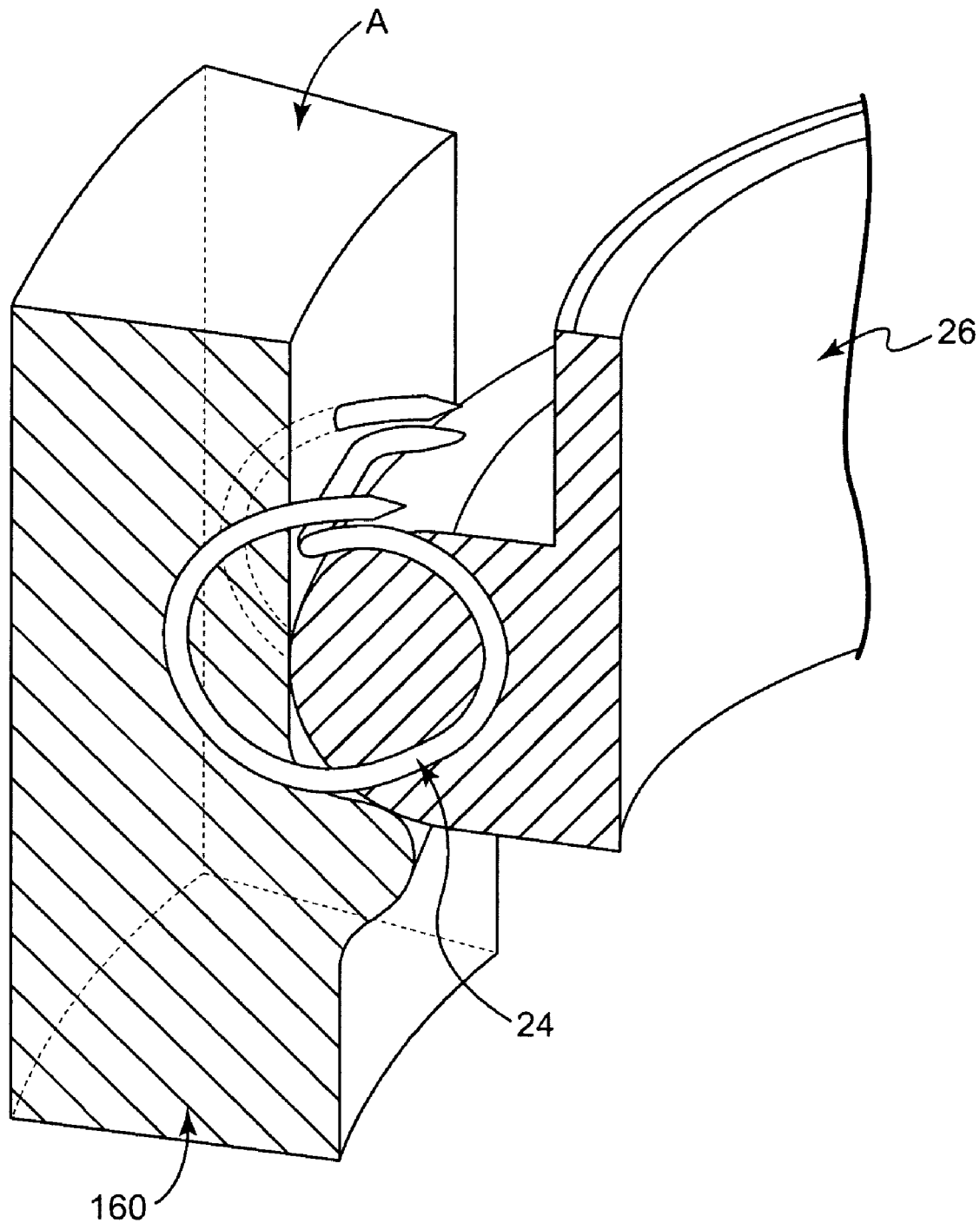
FIG. 12 illustrates a deployed fastener securing the replacement valve of FIGS. 10A and 10B to an aortic root in accordance with the present disclosure.
Figure 13:
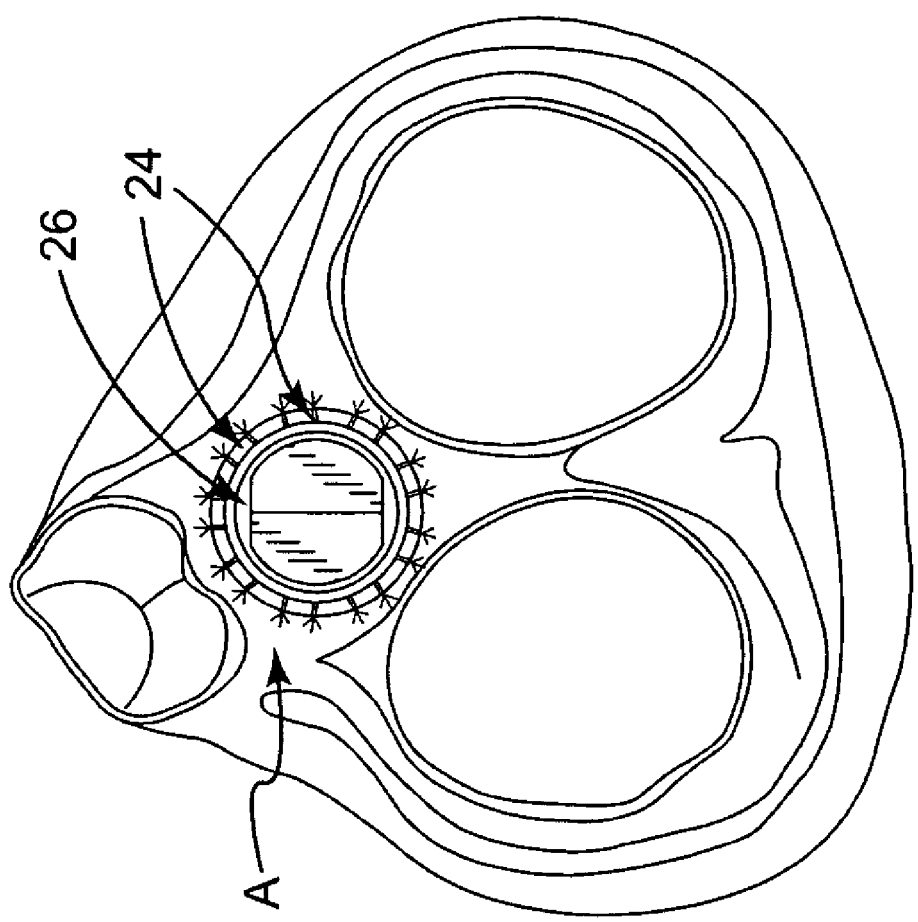
FIG. 13 illustrates the replacement valve of FIGS. 10A and 10B secured to the annulus of the aorta with a plurality of the fasteners or clips in accordance with the present disclosure.

Referring to FIGS. 12 and 13, securement of the prosthesis 26 is shown. FIG. 12 illustrates a deployed fastener or clip 24 securing the replacement valve 26 of FIGS. 10A and 10B to an aortic root 160 of an aorta A. FIG. 13 illustrates the replacement valve 26 of FIGS. 10A and 10B secured to the annulus of the aorta with a plurality of the fasteners or clips 24. The valve prosthesis 26 is in place over an aortic valve after delivery with the device 22 (FIG. 1A). Clips 24 penetrate through the replacement valve 26 and the aortic root 160 of the aorta A.

Although the apparatus 20 has been described in connection with aortic valve replacement, it also can be used to replace mitral, tricuspid, and pulmonary valves without any modifications. The apparatus 20 also can be used to implant annuloplasty rings or bands. For implanting annuloplasty bands, attachment clips on the posterior surface of the device 22 are not required and should be removed prior to beginning. The apparatus 20 also has catheter based applications. In this case, an angioplasty balloon replaces the valve sizing rod 32, thereby allowing the entire apparatus 20 to be collapsed into a catheter. Concentric tubes replace the hub 68 and the control devices, 94, 96. The concentric tubes communicate with the proximal end of the catheter to give the surgeon the ability to control the hub 68 and the control devices, 94, 96 from outside the body. A stentless valve (not shown) is loaded onto the distal end of the deployment device 22 as described above. The angioplasty balloon is deflated and the entire assembly collapsed into the catheter. The catheter is maneuvered into place via radiographic guidance. The valve 26 can be pushed out from the catheter and into the annulus. The angioplasty balloon can be inflated to cause the valve 26 and the clip holding assemblies 30 to expand radially until the valve 26 covers the valve annulus.

Figure 14:
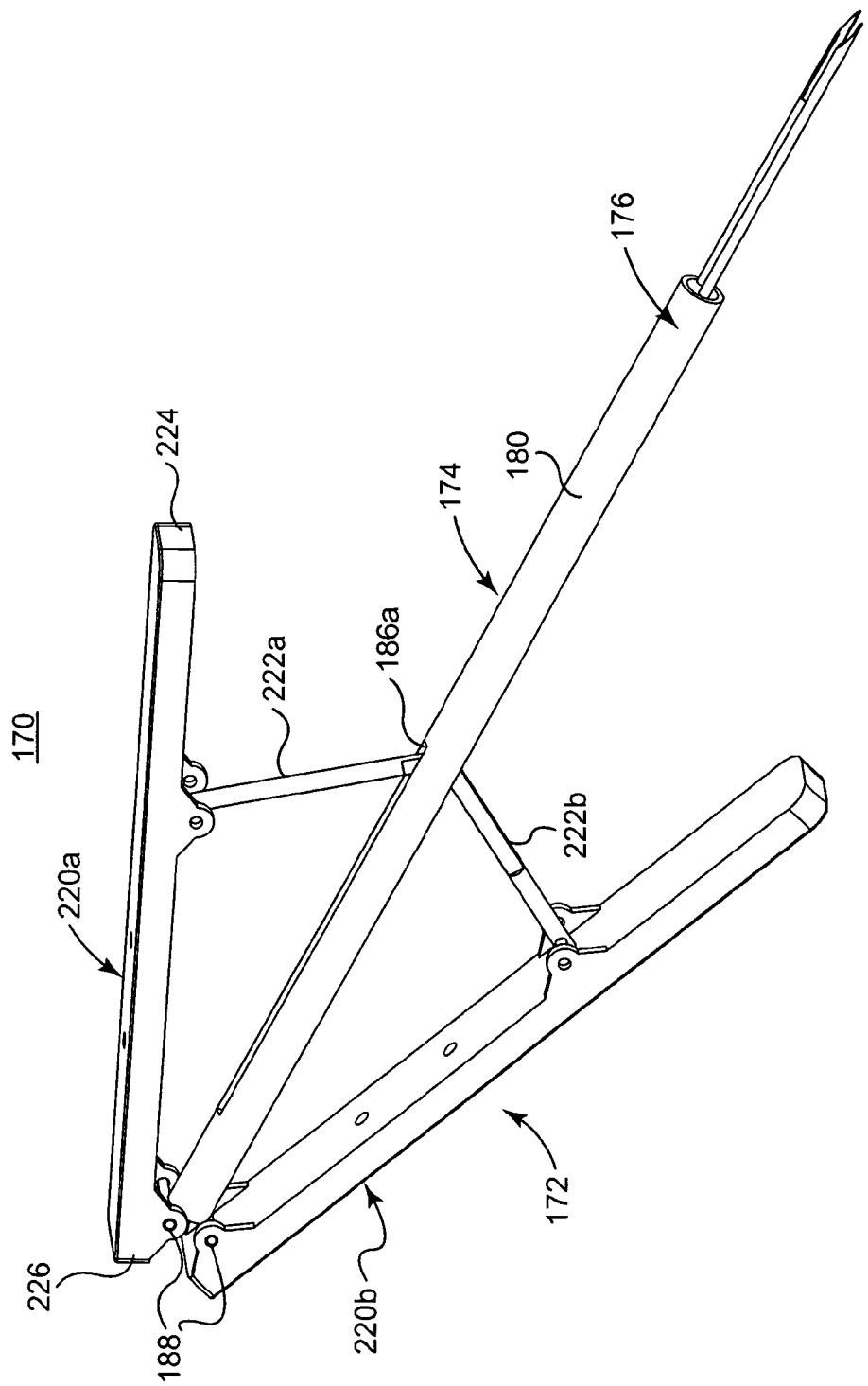
FIG. 14 is a perspective view of another surgical fastening apparatus in accordance with the present disclosure, including another deployment device.

While the deployment device 22 has been described in connection with substantially simultaneous delivery of a plurality of the clips 24, in other embodiments in accordance with aspects of the present disclosure, a single one of the clips 24 is delivered. For example, an alternative embodiment deployment device 170 is shown in FIG. 14, and includes a handle assembly 172 and a clip holding assembly 174. In general terms, the clip holding assembly 174 releasably retains the clip previously described (e.g., the clip 24 of FIG. 9). The clip holding assembly 174 is mounted to the handle assembly 172, with the handle assembly 172 being configured to effectuate operation of the clip holding assembly 174 in loading and deploying the clip 24.

The clip holding assembly 174 is akin to the clip holding assembly 30 (FIG. 1A) previously described. Unlike previous embodiments, however, the deployment device 170 provides or includes only a single one of the clip holding assemblies 174. With this in mind, the clip holding assembly 174 includes an outer component 176 and an inner component 178 (hidden in FIG. 14 and best shown in FIGS. 17A and 17B). The inner component 178 is slidably disposed within the outer component 176, and is adapted to selectively retain the clip 24. Further, the inner component 178 is configured for coupling to the handle assembly 172 to effectuate operation of the device 170.

Figure 15A:
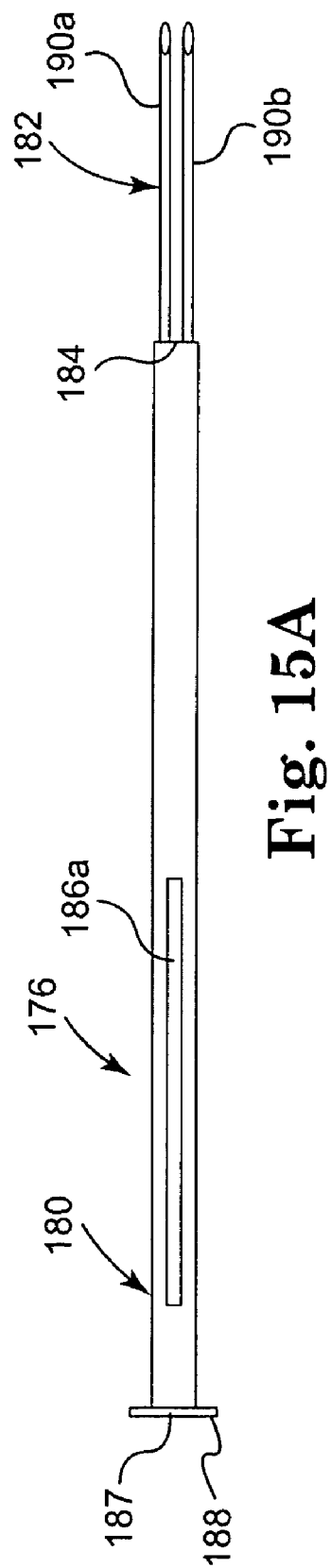
FIGS. 15A and 15B illustrate an outer component of a clip deployment assembly useful with the deployment device of FIG. 14.
Figure 15B:
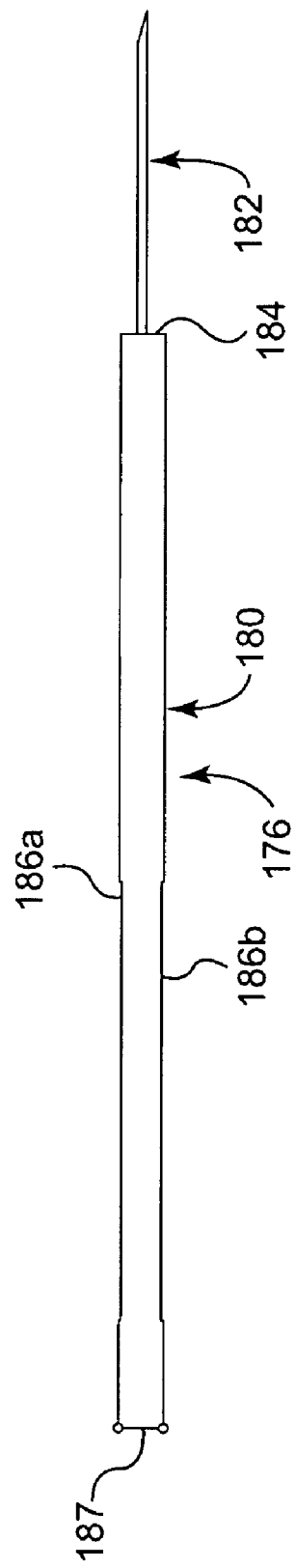

The outer component 176 is shown in greater detail in FIGS. 15A and 15B, and is akin to the outer component 106 (FIG. 5) previously described. The outer component 176 defines a proximal segment 180 and a distal segment 182. The proximal segment 180 is, in some embodiments, a conduit forming an inner lumen (not shown) sized to slidably receive the inner component 178 (FIG. 14). The lumen can extend an entire length of the proximal segment 180, and is longitudinally open at a leading end 184 thereof. In addition, the proximal segment 180 forms opposing slots 186a, 186b that are open to the lumen, and are sized to receive corresponding components of the handle assembly 172 as described below. Regardless, a trailing end 187 (that otherwise serves as the proximal end of the outer component 176) is configured for attachment to the handle assembly 172, and can include radially extending pins 188 for reasons described below.

Figure 16A:
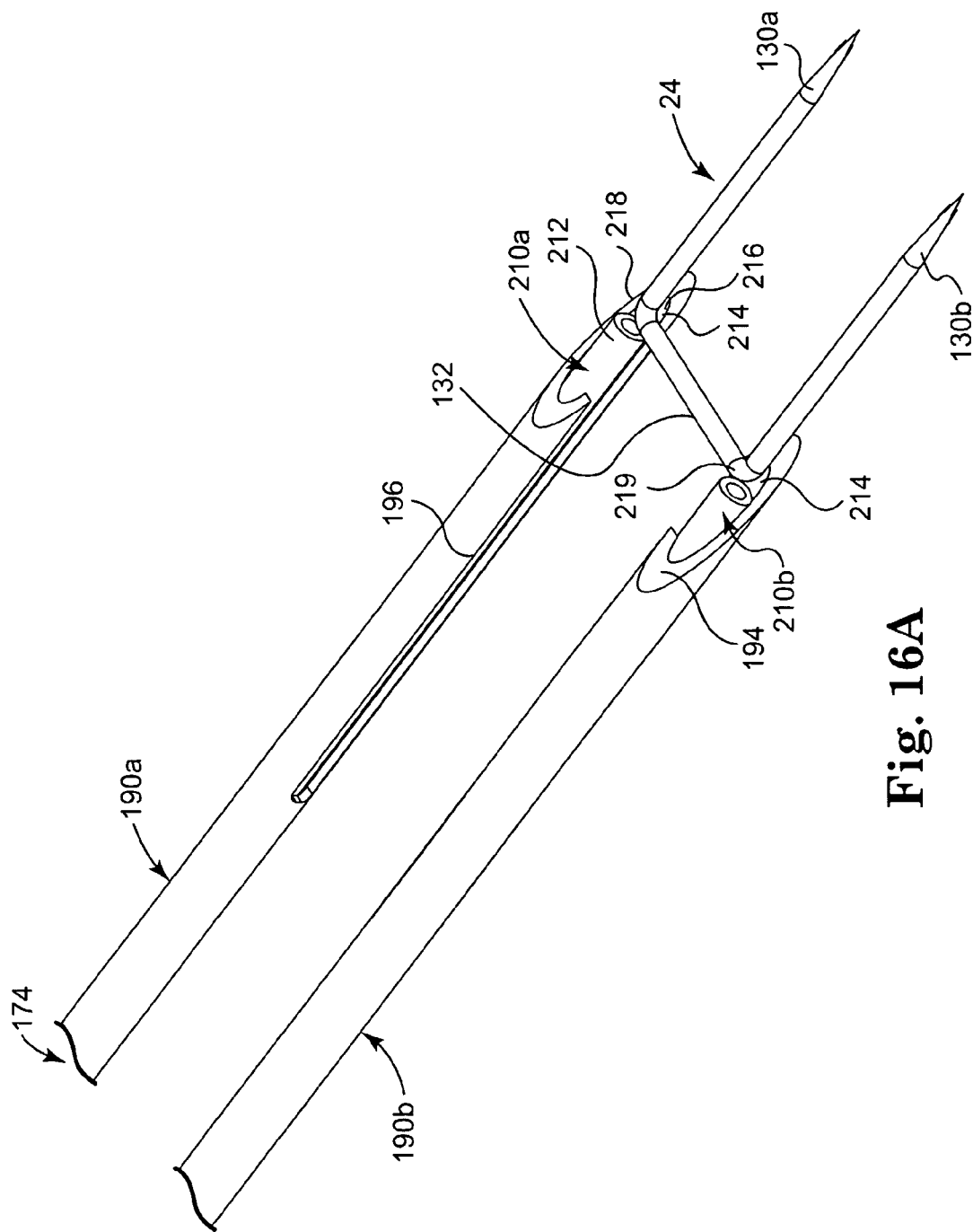
FIGS. 16A and 16B are enlarged views of a distal portion of the apparatus of FIG. 14 during use.
Figure 16B:
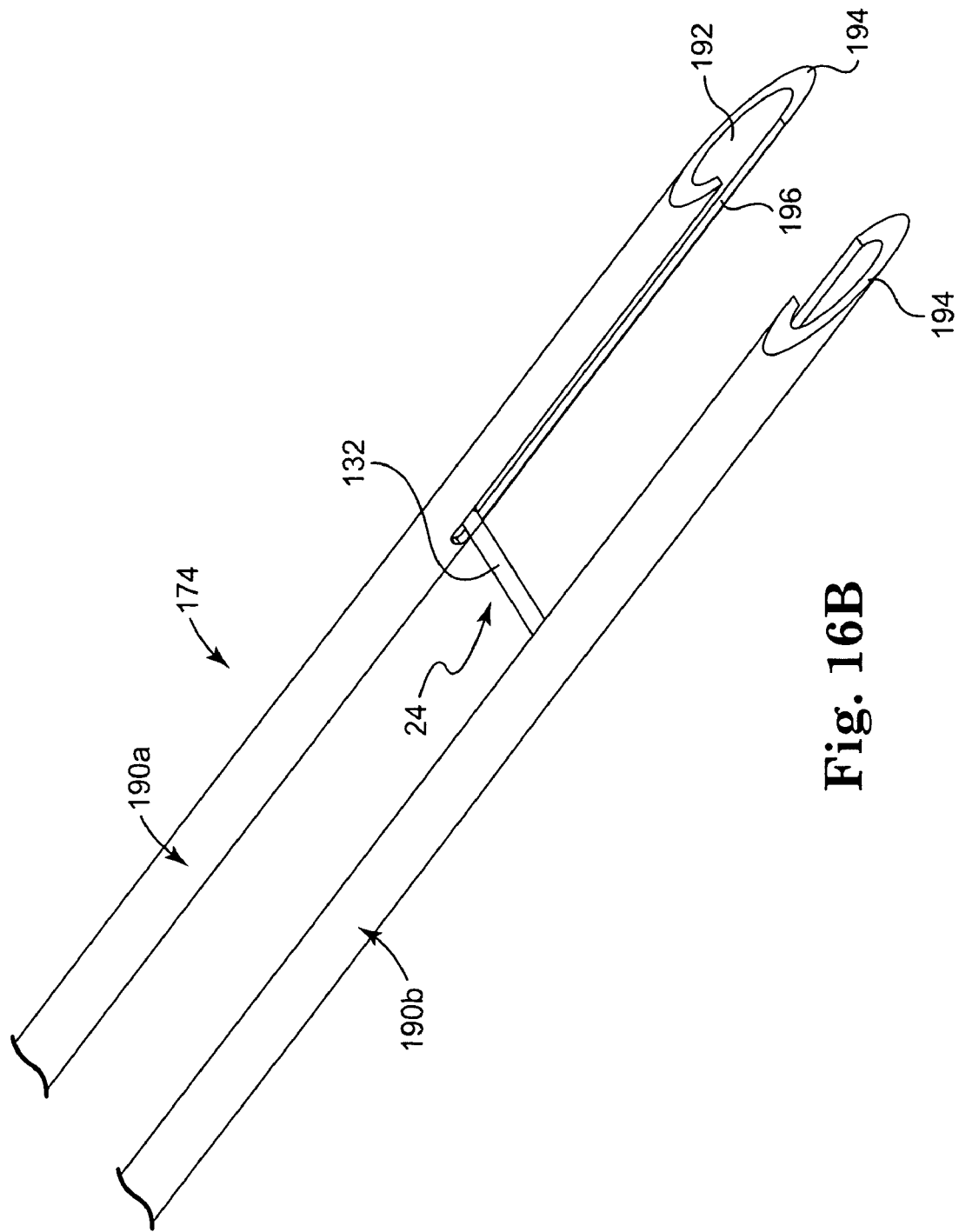

The distal segment 182 extends distally from the leading end 184 of the proximal segment 180 and includes or forms first and second hollow containment arms 190a, 190b that are akin to the hollow containment arms 90a, 90b (FIG. 9) previously described. As best shown in FIGS. 16A and 16B, the arms 190a, 190b each form a lumen 192 that and is open at a distal end 194. In this regard, the distal ends 194 can be sharpened as desired to promote piercing of tissue during use. Regardless, each of the containment arms 190a, 190b forms a side aperture 196 extending from the distal end 194 and open to the corresponding lumen 192. A length of the side apertures 196, as well as a lateral spacing between containment arms 190a, 190b, is commensurate with a size and shape of the clip 24 in the straightened state. As shown, the hollow containment arms 190a, 190b are arranged such that the slots 196 "face" one another. That is to say, the slot 196 of the first hollow containment arm 190a faces the second hollow containment arm 190b, and vice-versa.

The inner component 178 is shown in FIGS. 17A and 17B, and is akin to the inner component 120 (FIG. 6) previously described. The inner component 120 includes or defines a proximal portion 200 and a distal portion 202. The proximal portion 200 is sized to be slidably received within the lumen (not shown) of the proximal segment/conduit 180 of the outer retainer member 176 (FIGS. 15A and 15B), and can be solid or tubular shaft. Further, a trailing end 204 (that otherwise serves as a proximal end of the inner component 178) is configured for attachment to the handle assembly 172 as described below. For example, the trailing end 204 can form or include a pin 206.

The distal portion 202 extends from a leading end 208 of the proximal portion 200, and includes first and second transfer rods 210a, 210b that are akin to the transfer rods 92a, 92b (FIG. 9) previously described. The transfer rods 210a, 210b are sized and shaped to be coaxially received within a respective one of the lumens 192 of the arms 190a, 190b. At least a distal region 212 of each of the transfer rods 210a, 210b is tubular, configured to include an engagement feature that selectively receives the clip 24. For example, and as best shown in FIG. 16A, the distal region 212 is a tubular body having a wall 214 defining a passage of trough 216 sized in accordance with the clip 24. The passage 216 is exteriorly open along an axial slot 218. Further, a radial notch 219 is formed along the wall 214, and is open to the passage 216. The notch 219 is sized to facilitate extension of the clip 24 as described below. In this regard, the transfer rods 210a, 210b are arranged such that the corresponding notches 219 "face" one another. That is to say, the notch 219 of the first transfer rod 210a "faces" the second transfer rod 210b, and vice-versa.

Returning to FIG. 14, the handle assembly 172 includes first and second handle bodies 220a, 220b, and first and second levers 222a, 222b. The first lever 222a is pivotably attached to the first handle body 220a, and the second lever 222b is pivotably attached to the second handle body 220b. Further, the levers 222a, 222b are sized to be slidably received through a corresponding one of the slots 186a or 186b formed by the outer component 176.

Each of the handle bodies 220a, 220b includes or defines a leading end 224 and a trailing end 226. The corresponding lever 222a or 222b extends from the handle body 220a, 220b intermediate the ends 224, 226. In addition, the trailing end 226 is configured for mounting to the clip holding assembly 174. In particular, the trailing end 226 is pivotably attached to the pins 188 formed by the outer component 176. With this construction, the handle bodies 220a, 220b can be pivoted relative to the clip holding assembly 174, with the pins 188 acting as a fulcrum or pivot point. Finally, though not visible in the Figures, the levers 222a, 222b are adapted for mounting to the inner deployment apparatus 178. In particular, an end of the levers 222a, 222b opposite the corresponding handle body 220a, 220b is configured for mounting to the pin 206 of the inner component 178.

Upon final assembly, the inner component 178 is slidably disposed within the outer component 176, with the proximal portion/shaft 200 of the inner component 178 being slidably disposed within the proximal segment/conduit 180 of the outer component 176. Further, the transfer rods 210a, 210b are slidably disposed within respective ones of the hollow containment arms 190a, 190b. The handle bodies 220a, 220b are mounted to the outer component 176 in a hinged manner, with the levers 222a, 222b projecting into the lumen (not shown) of the proximal segment 180 via the slots 186a, 186b. Further, the levers 222a, 222b are connected to the pin 206 204 of the inner component 178 as described above.

With the above construction, when the handle bodies 220a, 220b are pivoted away from the clip holding assembly 174 (i.e., to the position of FIG. 14), the levers 222a, 222b proximally retract the inner component 178 relative to the outer component 176 (and thus retracted the transfer rods 210a, 210b relative to the hollow containment arms 190a, 190b). Conversely, when the handle bodies 220a, 220b (and in particular the leading ends 224) are pressed toward the clip holding assembly 174, the levers 222a, 222b distally extend the inner component 178 relative to the outer component 176, in turn causing the transfer rods 210a, 210b to slide distally relative to the hollow containment arms 190a, 190b.

During use, and with additional reference to FIG. 16A, the handle assembly 172 is actuated as described above, causing the transfer rods 210a, 210b to slide distally relative to the containment arms. Distal extension of the inner component 178 continues until the distal regions 212 of the transfer rods 210a, 210b are exteriorly accessible via the open, distal ends 194 of the hollow containment arms 190a, 190b. The clip 24 is then assembled to the transfer rods 210a, 210b, such as by placing the side portions 130a, 130b of the clip 24 into respective ones of the passages 216 of the arms 210a, 210b, via the respective slots 218. The intermediate portion 132 extends between the transfer rods 210a, 210b, passing through the corresponding notches 219. As a point of reference, for ease of illustration, the clip 24 is shown in FIG. 16A with the unconstrained side portions 130a, 130b being substantially straight. As described above, however, in some embodiments, the clip 24 is constructed such that the side portions 130a, 130b naturally assume or self-revert to a looped or curved state.

The handle assembly 172 (FIG. 14) is actuated to retract the inner component 178 proximally within the outer component 176. For example, the user can manually maneuver the leading end 224 of the handle bodies 220a, 220b outwardly away from the outer retainer member 176. Alternatively, the handle assembly 172 can include one or more biasing devices (e.g., springs) that bias the handle bodies 220a, 220b to the raised position of FIG. 14. With retraction of the inner component 178, the transfer rods 210a, 210b proximally retract with the hollow containment arms 190a, 190b, respectively. Due to engagement between the transfer rods 210a, 210b and the clip 24, this action the proximally pulls the clip 24 within the containment arms 190a, 190b. As part of this movement, the intermediate portion 132 passing through the side apertures 196 of the containment arms 190a, 190b as shown in FIG. 16B.

Deployment of the clip 24 from the delivery device 170 is accomplished in a reverse fashion. The handle assembly 172 is actuated (e.g., the handle bodies 220a, 220b are pivoted toward the clip holding assembly 174), causing the levers 222a, 222b (FIG. 14) to distally slide the inner component 178 relative to the outer component 176. This action, in turn, distally extends the transfer rods 210a, 210b, and thus the clip 24, relative to the distal ends 194 of the hollow containment arms 190a, 190b. Upon release from the confines of the containment arms 190a, 190b, the side portions 130a, 130b of the clip 24 self-revert to the natural, looped state. Further, once the intermediate portion 132 is distally at or beyond the distal end 194 of the containment arms 190a, 190b, the clip 24 is no longer captured by the clip holding assembly 174, effectuating complete deployment of the clip 24.

The single shot deployment device 170 described above is useful in performing a variety of tissue approximation procedures normally implicating use of a sewn mattress stitch. Often times, sewing a mattress stitch is time consuming and labor intensive; further, access to the mattress stitch is often times tenuous, greatly increasing the difficulty of stitch placement. Further, tiny sutures in areas of difficult access runs the risk of suture breakage, tying the suture too tight (thus resulting in tissue damage), or tying the tissue too loose (such that the tissue is not secure). The deployment device 170 allows a user to quickly and accurately place a mattress stitch without the risk associated with sutures in areas of difficult access. Thus, for example, the clip deployment device 170 can be used in connection with a number of different procedures, such as attaching annuloplasty bands; placement of an Alferi stitch placed between the anterior and posterior mitral leaflets to reduce mitral valve regurgitation; closure of a patent foramen ovala; pacemaker lead placement; and laparoscopic approximation. Further, the deployment device 170 can include alternative or different features apart from those described above. For example, a distal region of the deployment device 170 can be curved to enable approximation at various angles. Similarly, the distal region of the deployment device 170 can be configured for placement within, and delivery through, a catheter. With this approach, a concentric tube within the catheter will replace the inner component 178, with this concentric tube communicating with a proximal end of the catheter, thus giving a user the ability to extend and retract the inner component 178 from outside the patient. In yet another alternative configuration, the distal region of the deployment device 170 can be made into a cartridge. This would allow the device to "fire" multiple ones of the clips 24 with simple reloading. This configuration would also allow users to have a sharp piercing point on every use.

Figure 18:
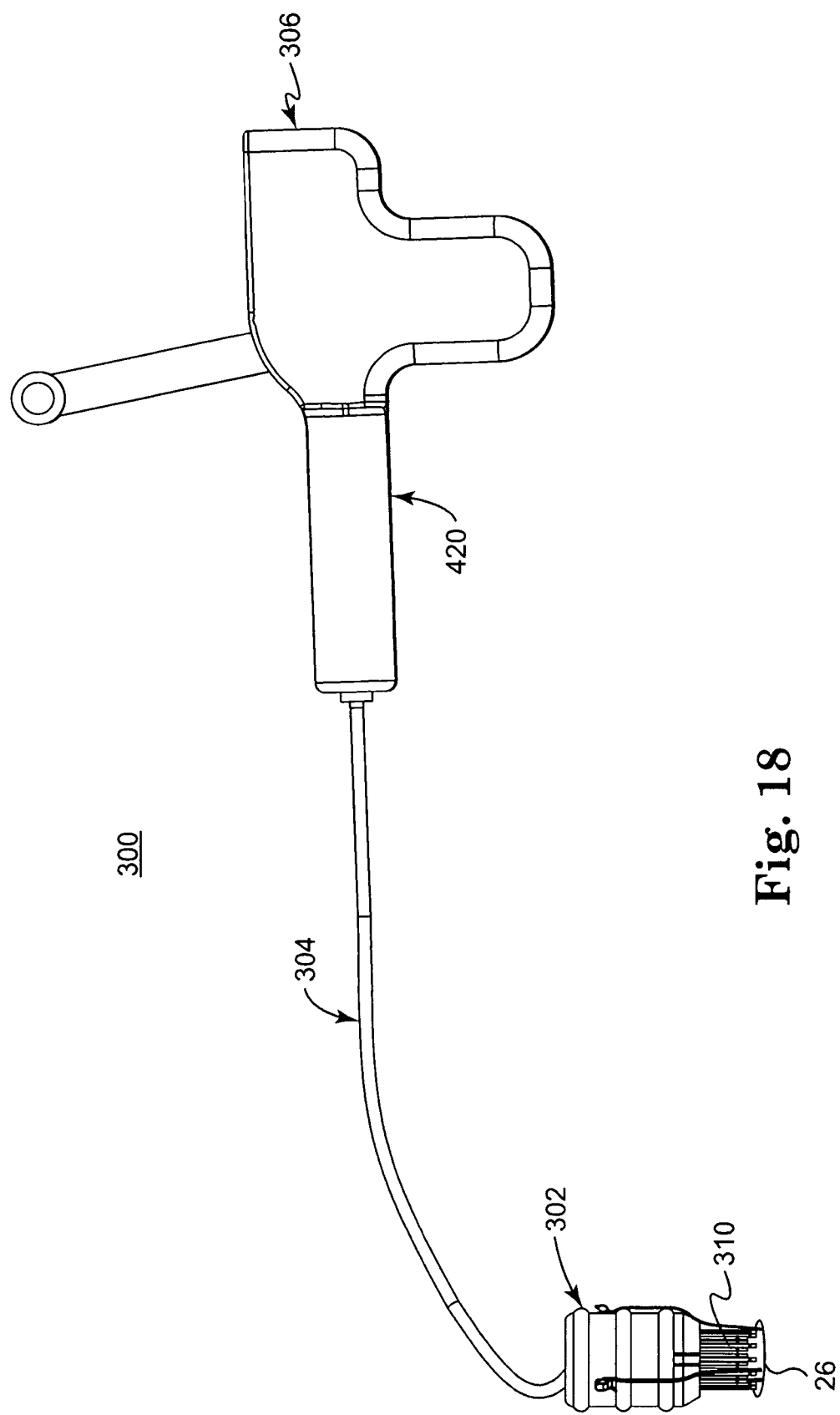
FIG. 18 is a side view of another deployment device in accordance with the present disclosure.

The deployment device 22 (FIG. 1A), 170 (FIG. 14) has been described as providing a direct, rigid connection of the clip holding assemblies 30 (FIG. 1A), 174 (FIG. 14) relative to an actuator or actuator assembly. With other constructions in accordance with the present disclosure, however, a remote actuation or deployment configuration can be employed. For example, FIG. 18 illustrates an alternative deployment device 300 in accordance with aspects of the present disclosure, and includes a deployment head 302, tubing 304, and a remote handle assembly 306. Details on the various components are provided below. In general terms, however, the deployment device 300 incorporates a hydraulic actuator to effectuate deployment of one or more clips (hidden in FIG. 18, but akin to the clips 24 previously described) at a surgical site. More particularly, the deployment head 302 includes various assemblies that releasably retain one or more of the clips. The deployment head 302 is hydraulically actuated, and is fluidly connected to the remote handle 306 via the tubing 304. Finally, the remote deployment handle assembly 306 provides user-actuated control over operation of the deployment head 302 via delivery and withdrawal of fluid to and from the deployment head 302.

Figure 19:
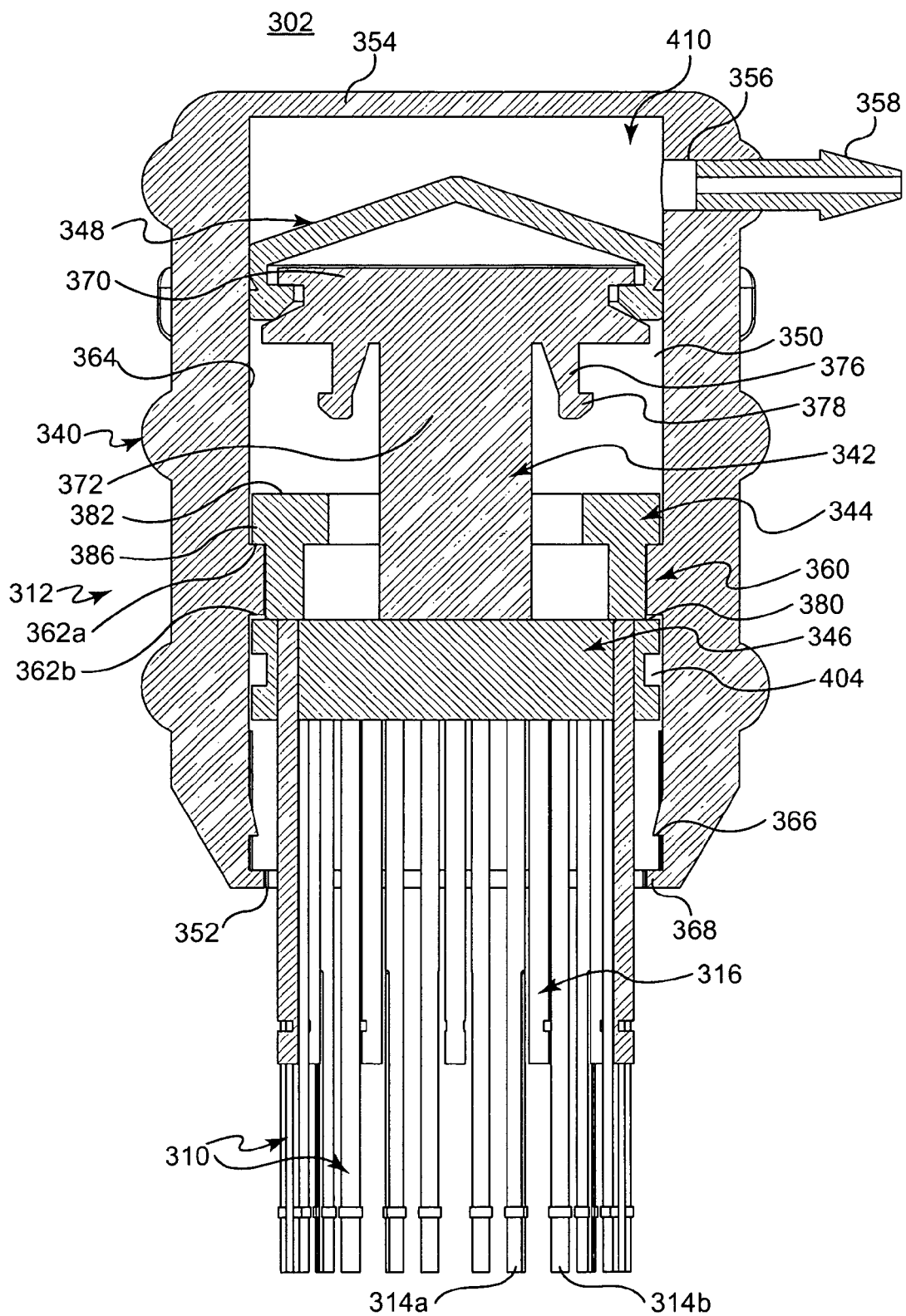
FIG. 19 is an enlarged, cross-sectional view of a deployment head portion of the deployment device of FIG. 18.
Figure 20:
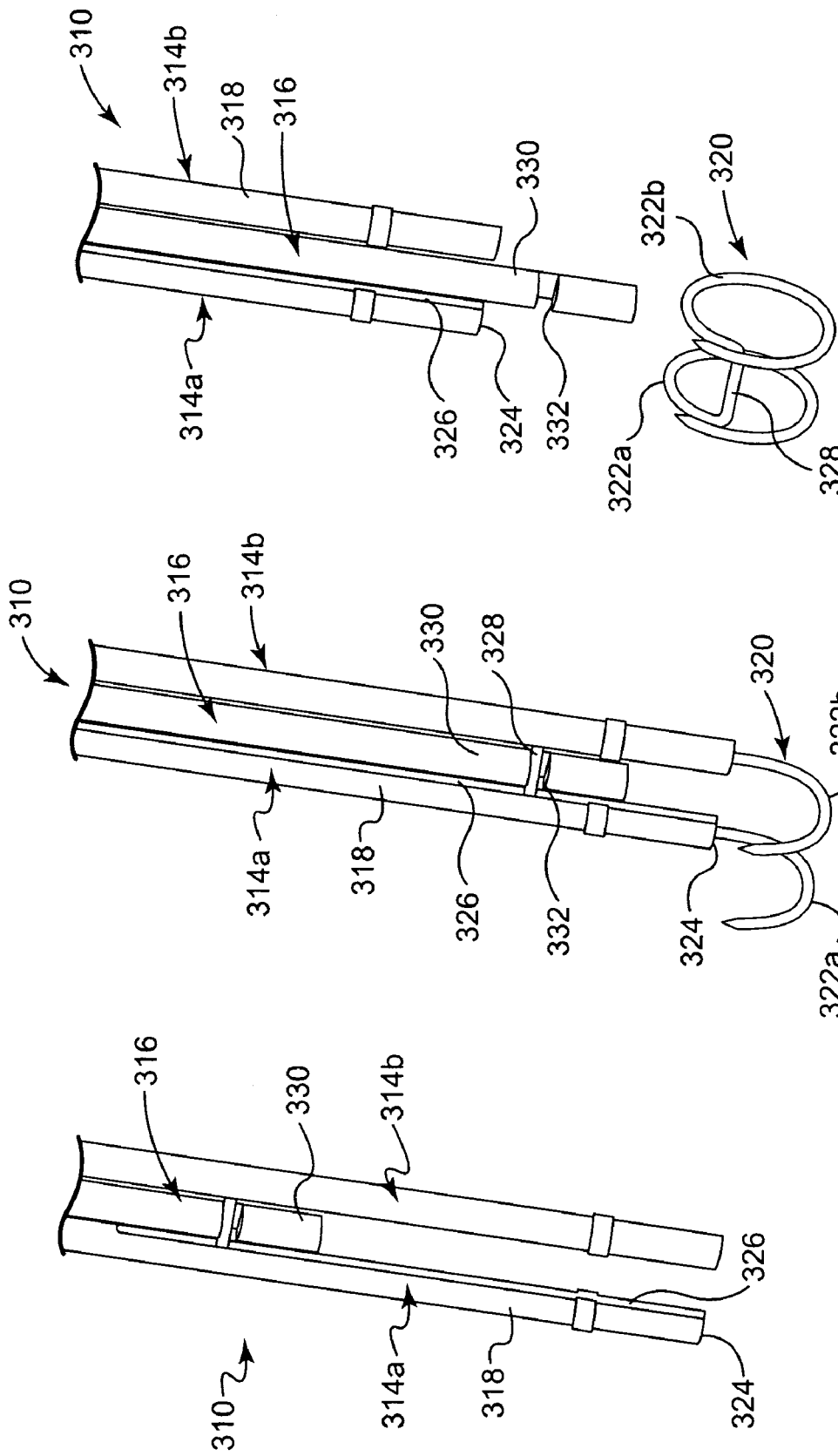
FIGS. 20A-20C are enlarged, perspective views of a distal portion of a clip holding assembly portion of the deployment device of FIG. 18, illustrating deployment of a clip.

The deployment head 302 is shown in greater detail in FIG. 19, and includes a plurality of clip holding assemblies 310 maintained by, and extending distally from, a housing assembly 312. With additional reference to FIGS. 20A-20C, each of the clip holding assemblies 310 includes, in some embodiments, an opposing pair of hollow containment arms 314a, 314b and a transfer rod 316. The hollow containment arms 314a, 314b each form a lumen (not shown) along at least a distal region 318 thereof, with the lumen being sized to receive a portion of a clip 320 (e.g., a side portion 322a or 322b of the clip 320). In this regard, the lumen formed by each of the hollow containment arms 314a, 314b is longitudinally open at a distal end 324, as well as along a longitudinally extending side aperture 326. The side aperture 326 is sized to permit passage of a corresponding portion of the clip 320 (e.g., an intermediate portion 328), with the hollow containment arms 314a, 314b being arranged such that the respective side apertures 326 "face" one another. For example, the side aperture 326 of the first hollow containment arm 314a "faces" the second hollow containment arm 314b, and vice-versa.

The transfer rod 316 is slidably disposed between the hollow containment arms 314a, 314b as shown, and can be solid or tubular. In this regard, operation of the deployment head 302 (FIG. 19) in transitioning from the transfer rod 316 from the position of FIG. 20A to the position of FIG. 20C (and vice-versa) is described below. A distal segment 330 of the transfer rod 316 includes an engagement feature configured to selectively receive or engage a portion of the clip 320. For example, the distal segment 330 can form a notch 332 sized in accordance with a diameter or other dimension of the intermediate portion 328 of the clip 320. With this arrangement, axial movement of the drive rod 316 relative to the hollow containment arms 314a, 314b operates to capture and deploy the clip 320 as described below.

Returning to FIG. 19, the housing assembly 312 is configured to establish a desired circumferential arrangement and spacing of the clip holding assemblies 310 relative to one another, as well as to effectuate movement of the individual containment arms 314a, 314b and the transfer rods 316. With this in mind, and in some embodiments, the housing assembly 312 includes a housing 340, a drive piston 342, a retractor body 344, a drive plate 346, and a stopper 348. The housing 340 retains the various components 342-348. The drive piston 342 is releasably connectable to the retractor body 344 that in turn commonly maintains the transfer rods 316. Upon final assembly, the drive piston 342/retractor body 344 is axially slidable within the housing 340, as is the drive plate 346. With this in mind, the drive plate 346 retains the hollow containment arms 314a, 314b, such that movement of the drive piston 342/retractor body 344 relative to the transfer plate 346 axially moves the drive rods 316 relative to the corresponding hollow containment arms 314a, 314b. Similarly, the drive piston 342 selectively moves the drive plate 345 relative to the retractor body 344, and thus the hollow containment arms 314a, 314b relative to the corresponding transfer rods 316. Finally, the stopper 348 establishes a fluid tight seal of the drive piston 342 within the housing 340.

The housing 340 can assume a variety of forms appropriate for maintaining the components 342-348. In some embodiments, the housing 340 forms or defines an internal cavity 350 extending from an open, first end 352 to a closed, second end 354. Relative to these orientations, the housing 340 is configured to establish a fluid connection with the cavity 350 (apart from the open, first end 352), such as via a passage 356 formed adjacent the top end 354. In this regard, the housing 340 can be configured to facilitate connection of the tubing 304 (FIG. 18) relative to the passage 356, and thus may include or form a barbed port 358.

Figure 21:
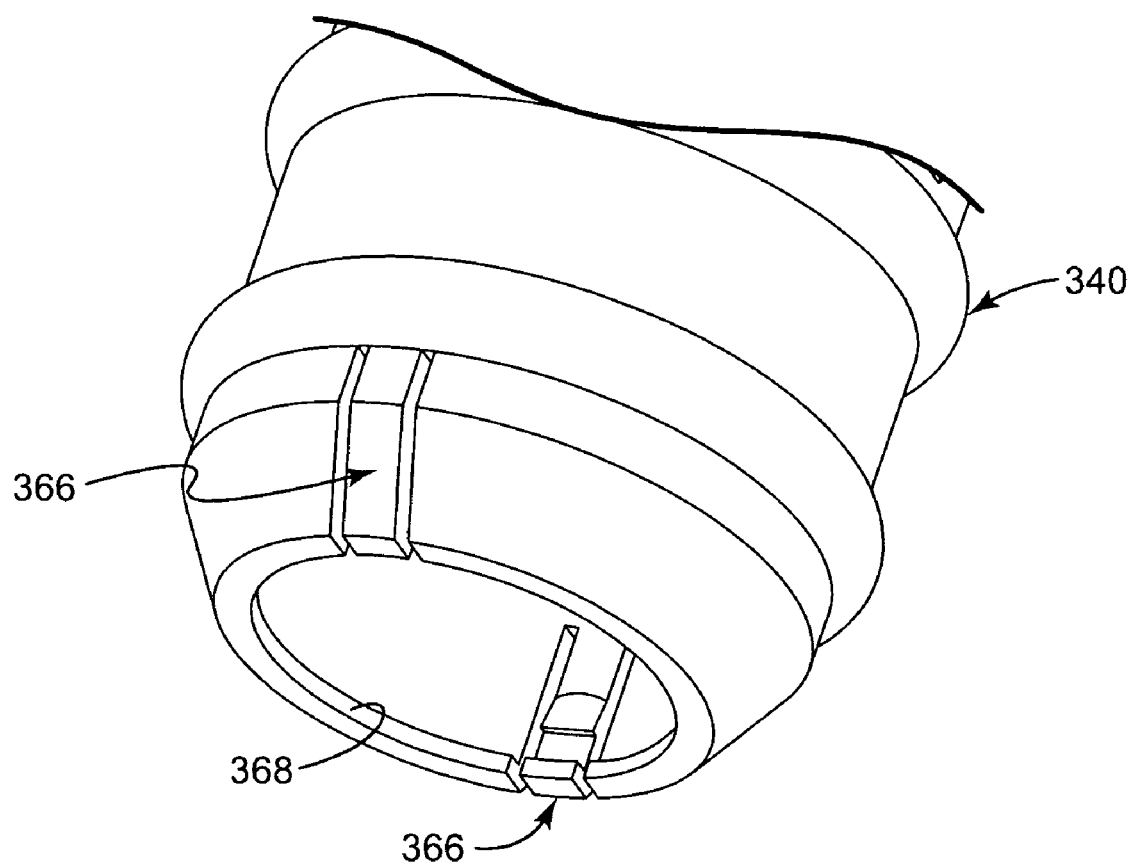
FIG. 21 is a perspective view of a portion of a housing associated with the deployment device of FIG. 18.

The housing 340 can form additional features for interfacing with the components 342-348. For example, an intermediate shoulder 360 can be formed as an annular projection within the cavity 350. The shoulder 360 defines opposing, first and second sides 362a, 362b. Relative to the closed, second end 354 of the housing 340, the first side 362a establishes a first region 364 of the cavity 350. The first region 364 is characterized by a constant diameter commensurate with an outer dimension of the stopper 348 as described below. Further, dimensions of the first side 362a correspond with dimensions of the retractor body 344, thus serving as a stop surface relative to movement of the retractor body 344 toward the first end 352. Conversely, the second side 362b is dimensioned in accordance with the drive plate 346, and thus serves as a stop surface relative to movement of the drive plate 346 toward the second end 354. Finally, the housing 340 forms, in some embodiments, one or more deflectable fingers 366 adjacent the first end 352, along with a lip 368. As described below, the fingers 366 are configured in accordance with features of the drive plate 346, and are adapted to selectively engage and capture the drive plate 346 (in combination with the lip 368) upon placement of the drive plate 346 or over the fingers 366. For example, as shown in FIG. 21, the fingers 366 can be deflectable (e.g., molded as living hinges) relative to a remainder of the housing 340 for reasons described below.

Figure 22:
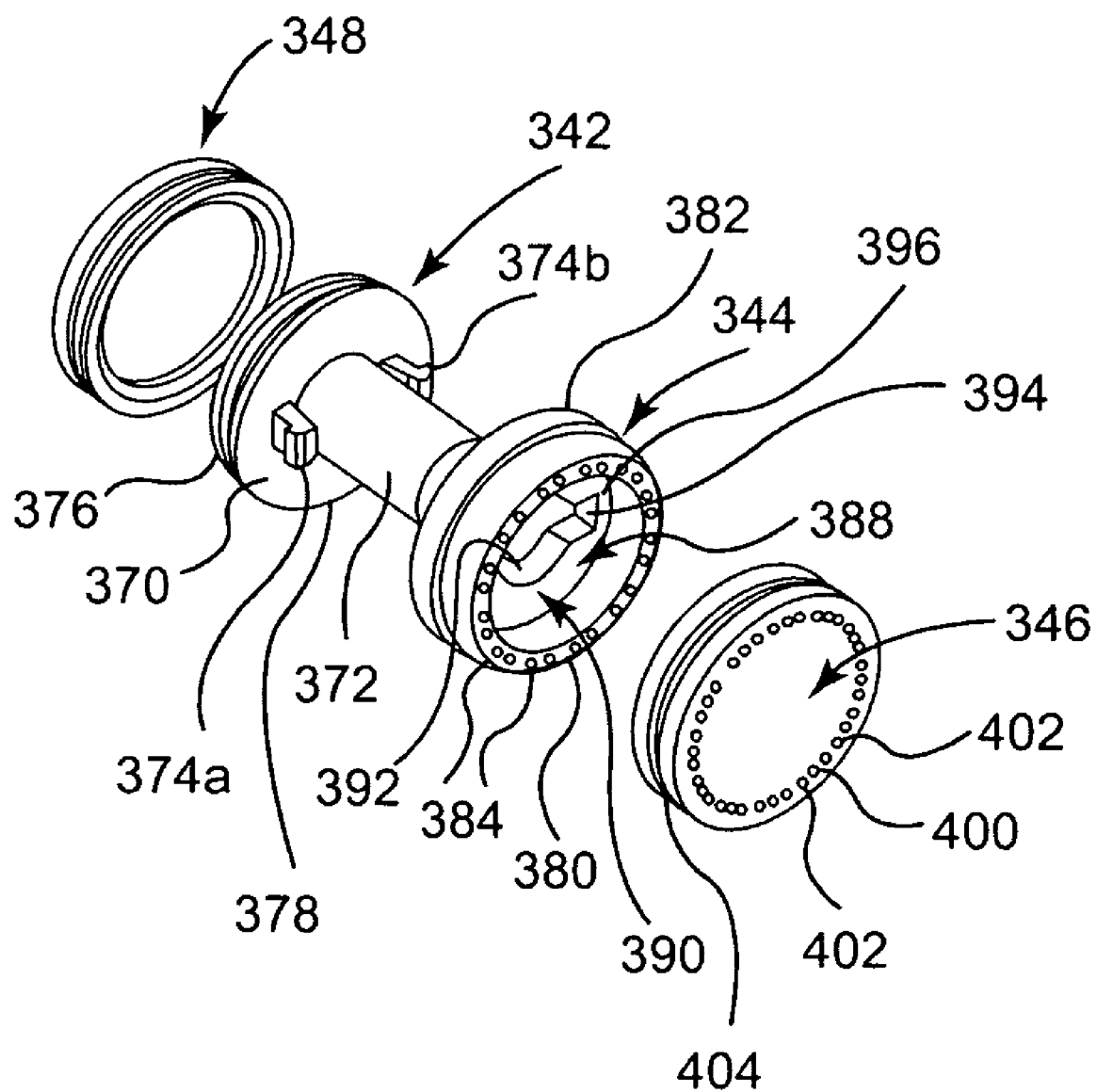
FIG. 22 is an exploded view of a portion of the deployment head of FIG. 19 in deploying a fastener or clip.

With reference to FIGS. 19 and 22, the drive piston 342 includes a head 370 and a shaft 372. The head 370 is sized to receive the stopper 348. The shaft 372 is rigidly attached to, and extends from, the head 370. In addition, in some embodiments, the drive piston 342 includes engagement legs 374a, 374b. The legs 374a, 374b are positioned at opposite sides of the shaft 372, and each include a body 376 terminating at a locking end 378 opposite the head 370. The bodies 376 are deflectable in a radially inward manner (e.g., molded as living hinges), and exhibit sufficient structural stiffness to self-return to the orientation shown in FIG. 22. The locking ends 378 are configured to releasable engage a corresponding feature of the retractor body 344 as described below.

The retractor body 344 has a ring-like shape, defining a leading side 380 and a trailing side 382. The leading side 380 forms a plurality of apertures 384 sized to receive corresponding ones of the hollow containment arms 314a, 314b of each of the clip holding assemblies 310. While the retractor body 344 is annular, an increased outer diameter is defined at a trailing portion 386 otherwise extending from the trailing side 382. Further, the retractor body 344 includes or forms a transverse wall 388 at the trailing side 382. The transverse wall 388 forms or defines a passageway 390 having a central region 392 and opposing side regions 394 (one of which is shown in FIG. 22). The central region 392 is sized in accordance with the shaft 372 of the drive piston 342, permitting slidable movement of the shaft 372 through the central region 392. Conversely, the side regions 394 are sized in accordance with the legs 374a, 374b of the drive piston 342. More particular, the transverse wall 388 defines an engagement surface 396 (one of which is shown in FIG. 22) adjacent the side regions 394. During operation, the legs 374a, 374b extend through a corresponding one of the side regions 394, with the locking ends 378 contacting a corresponding one of the engagement surfaces 396.

The drive plate 346 is a disc-shaped body, forming a plurality of apertures 400 interposed between corresponding pairs of passages 402. The apertures 400 are sized for mounting to a respective one of the transfer rods, whereas the passages 402 are sized to coaxially receive a respective one of the hollow containment arms 314a, 314b. The drive plate 346 further defines a circumferential groove 404, intermediately formed between opposing, first and second ends 406, 408. As described below, the circumferential groove 404 is configured to selectively interface with the fingers 366 (FIG. 21) provided with the housing 340.

Finally, the stopper 348 is configured for assembly to the head 370, as well as for mounting within the housing 340 (FIG. 19). In this regard, the stopper 348 is formed of a material appropriate for forming a fluid-tight seal within the housing 340, and thus can be formed of rubber or other materials.

Construction of the housing assembly 312 is provided with specific reference to FIG. 19. The stopper 348 is mounted to the head 370 of the drive piston 342. The stopper 348/drive piston 342 is assembled within the cavity 350 of the housing 340, with the stopper 348 forming a seal relative to the housing 340. Upon assembly, then, a hydraulic chamber 410 is established within the cavity 350 between the housing 340 and the stopper 348, with the passage 356/barbed port 358 being fluidly connected to the hydraulic chamber 410.

The retractor body 344 is also disposed within the cavity 350. In particular, the retractor body 344 is positioned such that the trailing portion 386 is between the intermediate shoulder 360 and the second end 354 of the housing 340. As shown, a dimensional relationship between the trailing portion 386 and the shoulder 360 is such that the trailing portion 386 abuts or rests against the first side 362a of the shoulder 360. Further, the shaft 372 of the drive piston 342 extends through the passageway 390 formed by the retractor body 344, and in particular the central region 392 (best shown in FIG. 22). The retractor body 344 is arranged such that the side regions 394 of the passageway 390 are axially aligned with the legs 374a, 374b.

The drive plate 346 is similarly disposed within the cavity 350. In the raised position of FIG. 19, the drive plate 346 abuts the second side 362b of the shoulder 360 of the housing 340. In this regard, the drive plate 346 can be partially retained in this raised position via an engagement feature (not shown) interiorly formed by the housing 340. Regardless, the drive plate 346 is axially slidable along the cavity 350 from the raised position shown, toward the first end 352 as described below.

The clip holding assemblies 310 can be assembled to corresponding components of the housing assembly 312 prior to, during, or following construction of the housing assembly 312. Regardless, the clip holding assemblies 310 are assembled such that the hollowing containment arms 314a, 314b associated with each of the clip holding assemblies 310 extend through the passages 402 (hidden in FIG. 19 but shown in FIG. 22), and are mounted to the retractor body 344 (e.g., via the apertures 384 of FIG. 22). The transfer rod 316 of each of the clip holding assemblies 310 is mounted to the drive plate 346 via corresponding ones of the apertures 400.

Figure 23A:
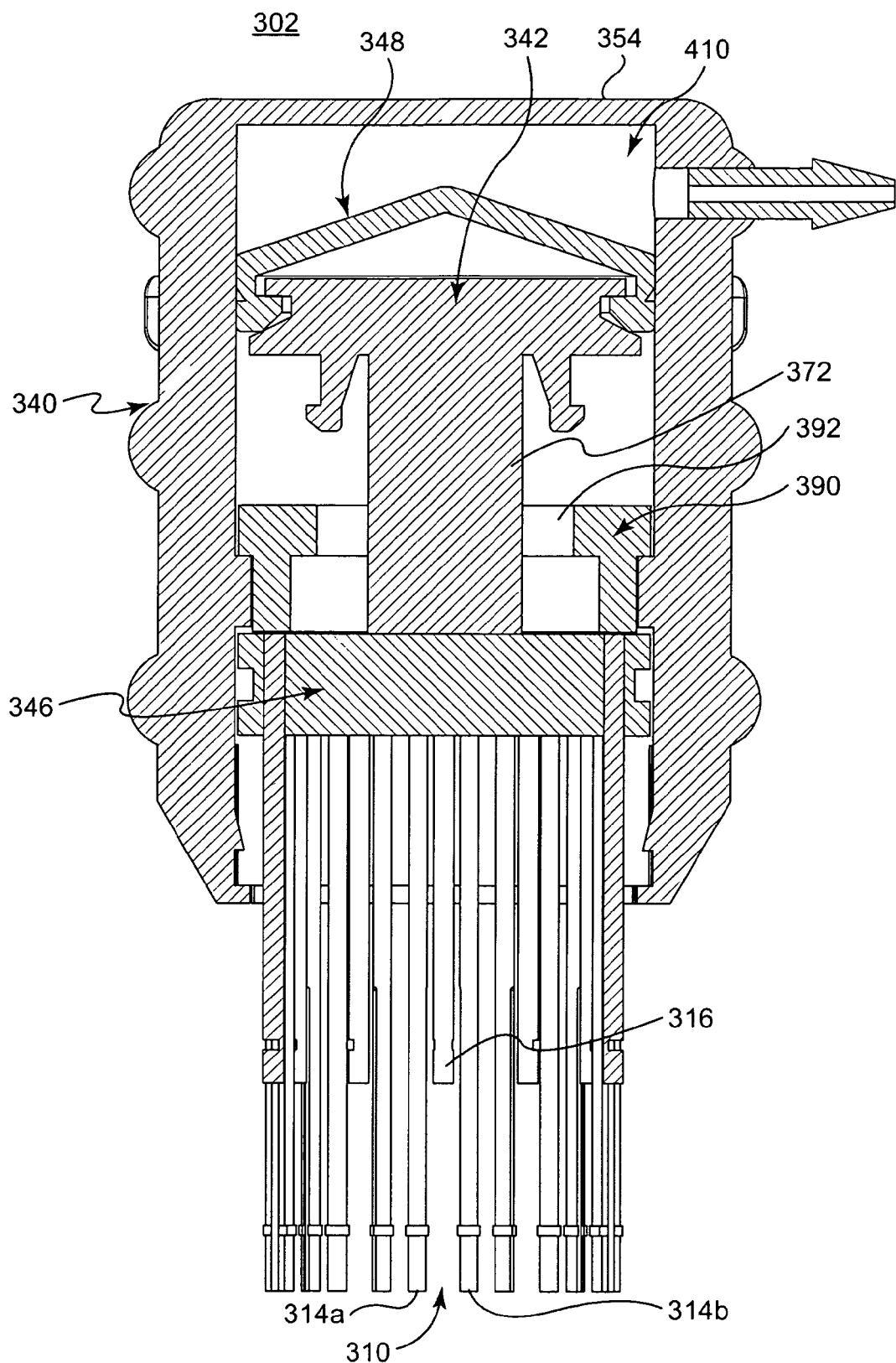
FIGS. 23A-23C are cross-sectional views illustrating operation of the deployment head of FIG. 19.

During operation, the deployment head 302 operates to substantially simultaneously deploy the clips 320 (FIG. 20C) from respective ones of the clip holding assemblies 310 as follows with reference to FIGS. 23A-23C. Operation of the deployment head 302 includes three stages. In an initial stage (FIG. 23A), the clips 320 (hidden in FIG. 23A) have been loaded within each of the clip holding assemblies 310 as previously described. In this regard, the transfer rod 316 of each assembly 310 is retracted relative to the corresponding hollow containment arms 314a, 314b in retracting the clips 320 within the clip holding assemblies 310. More particularly, the hydraulic chamber 410 is substantially evacuated of the hydraulic fluid (not shown), with the so-formed vacuum drawing the stopper 348/drive piston 342 toward the second end 354 of the housing 340 as shown. As a point of reference, the drive plate 346 can be releasably assembled to the shaft 372 of the drive piston 342, such that upward movement of the drive piston 342 forces the drive plate 346, and thus the transfer rods 316 maintained thereby, to the raised, initial position of FIG. 23A. Alternatively, the drive plate 346 can be releasably assembled to the housing 340 in the position shown in FIG. 23A.

Figure 23B:
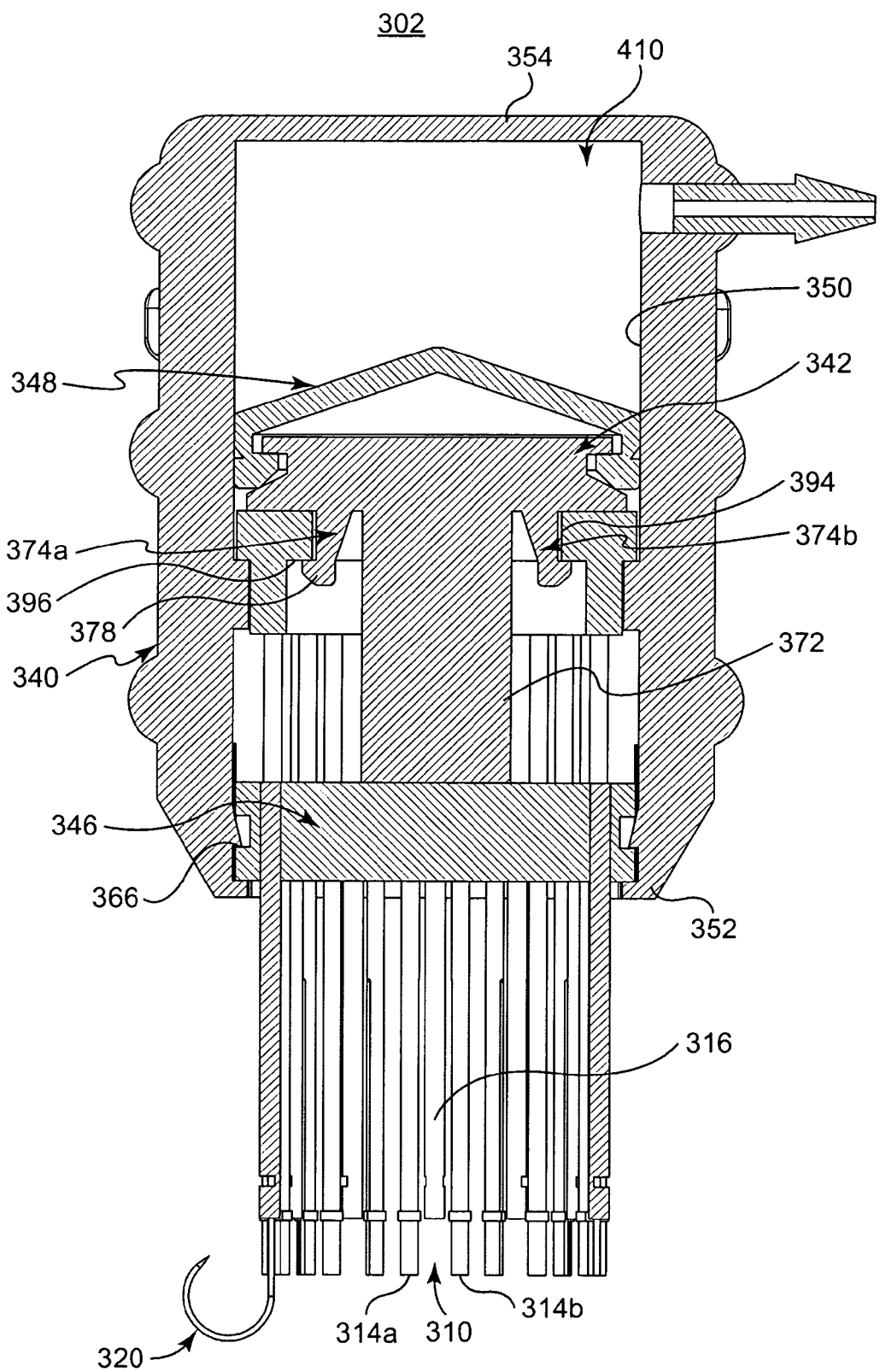
Figure 24:
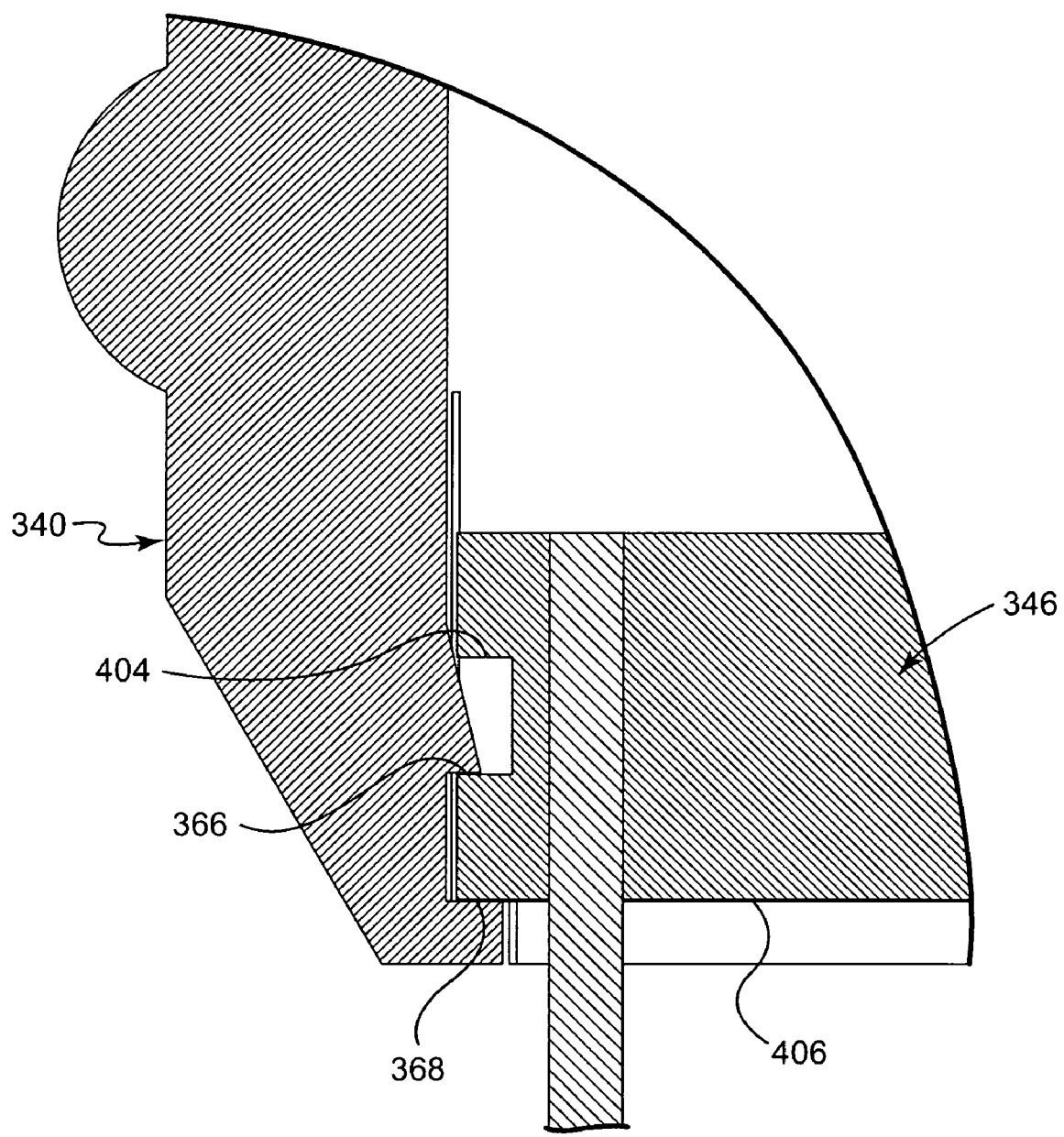
FIG. 24 is an enlarged view of a portion of the deployment head of FIG. 19 during use.

Regardless, during a deploy stage as shown in FIG. 23B, hydraulic fluid is forced into the hydraulic chamber 410, imparting a force onto the stopper 348/drive piston 342. In response, the drive piston 342 is forced to move within the cavity 350, and toward the first end 352. With this movement, the shaft 372 of the drive piston 342 progresses through the central region 392 of the passageway 390 of the retainer body 344 and contacts the drive plate 346. With further distal or downward movement of the drive piston 342, the shaft 372 forces the drive plate 346 to move or slide distally toward the first end 354. The transfer rods 316 similarly move in a distal manner with movement of the drive plate 346. As described above, all of the hollow containment arms 314a, 314b are slidably associated with the drive plate 346, and thus remain stationary with distal movement of the drive plate 346—transfer rods 316. Movement of the transfer rods 316 is, in turn, imparted onto the clips 320 (one of which is shown in FIG. 23B), effectuating at least partial deployment of the clips 24 from the corresponding clip holding assemblies 310 (as previously described with reference to FIGS. 20A-20C). Distal movement of the drive plate 346 continues until the drive plate 346 engages the capture fingers 366 of the housing 340. For example, and as best shown in FIG. 24, the fingers 366 are engaged within the circumferential groove 404 of the drive plate 346. Further, the lip 368 of the housing 340 contacts the first end 406 of the drive plate 346, thus preventing further downward or distal movement.

Returning to FIG. 23B, as part of the deploy stage, the legs 374a, 374b of the drive piston 342 deflect along the side regions 394 of the passageway 390. Upon clearing the transverse wall 388, the legs 374a, 374b are allowed to revert to a natural, radially outward extension, such that the locking ends 378 contact the engagement surfaces 396 of the retractor body 344. With this arrangement, then, the retractor body 344 is effectively locked relative to the drive piston 346.

Figure 23C:
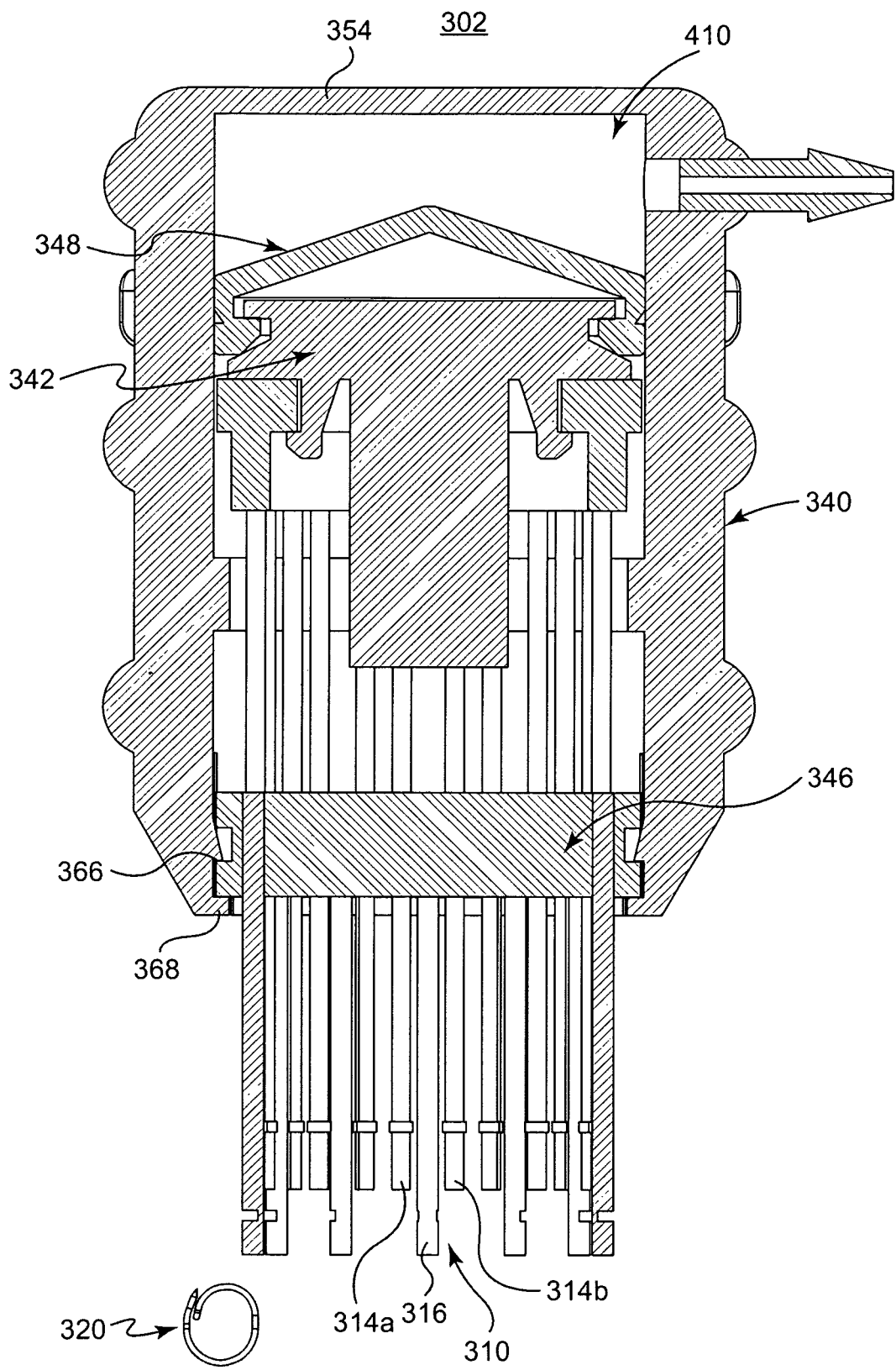

Following the deploy stage, the deployment head 302 is operated through a retraction stage as shown in FIG. 23C. In particular, the hydraulic fluid is withdrawn from the hydraulic chamber 410, establishing a vacuum-like condition. This, in turn, draws the stopper 348/drive piston 342 proximally (or upwardly). Because the retractor body 344 is now locked to the drive piston 342, the retractor body 344 moves in a similar, proximal direction. The hollow containment members 314a, 314b are attached to the retractor body 344, and thus proximally retract in a similar manner. In this regard, and as previously described, the hollow containment members 314a, 314b are slidably associated with the drive plate 346, such that the drive plate 346 does not move with movement of the drive piston 342. Further, the locked interface between the drive piston 342 and the housing 340 (via the fingers 366 and the lip 368) ensures that the drive plate 346, and thus the transfer rods 316, remain stationary during retraction of the retractor body 344/hollow containment members 314a, 314b. In conjunction with this proximal retraction of the hollow containment members 314a, 314b, an entirety of the corresponding clip 320 is fully exposed, and thus readily reverts away from the deployment head 302.

Figure 25:
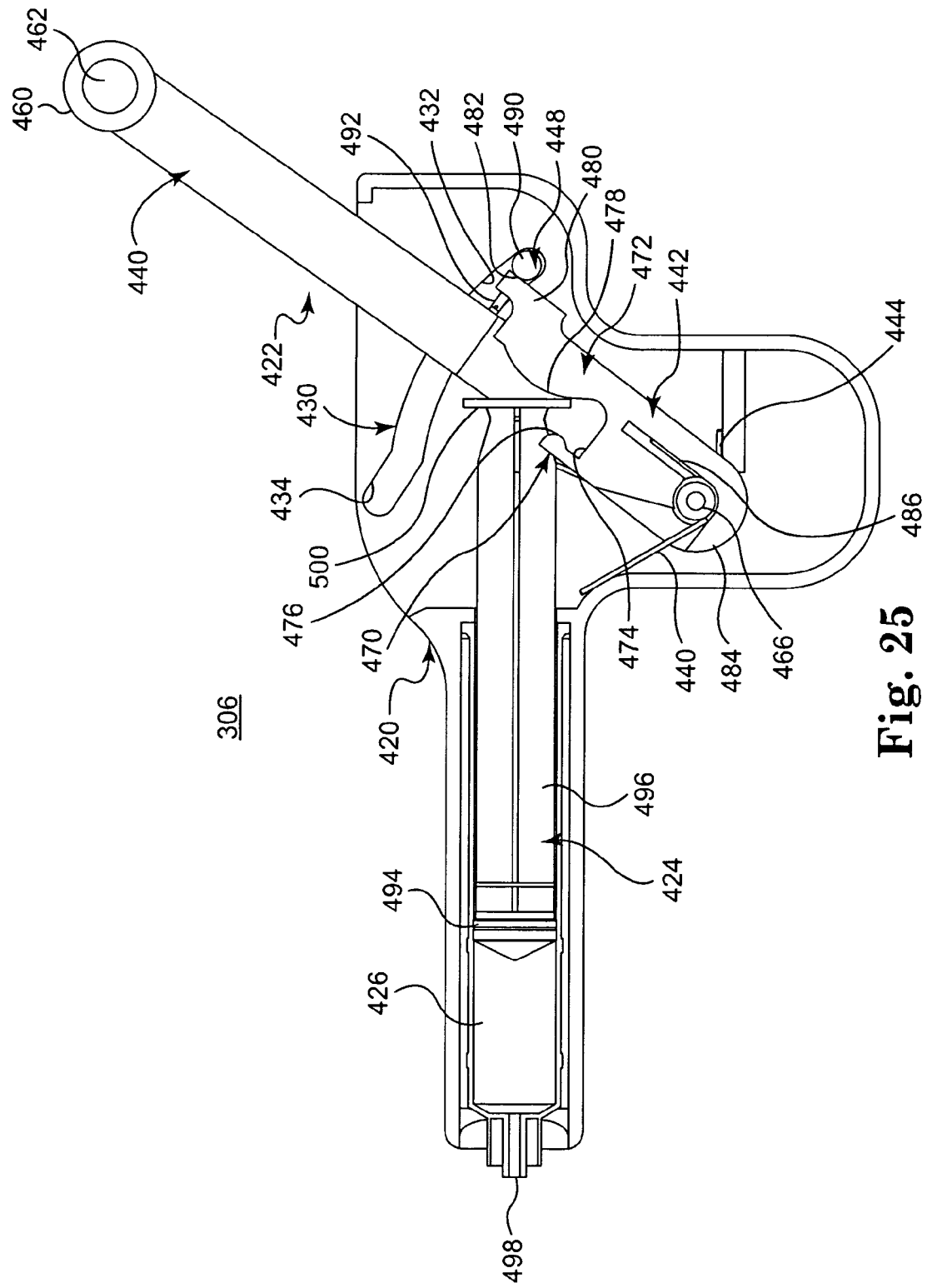
FIG. 25 is a cross-sectional view of a remote handle assembly portion of the deployment device of FIG. 18.

Returning to FIG. 18, and with additional reference to FIG. 25, the remote handle assembly 306 can assume a wide variety of forms capable of effectuating delivery and withdrawal of hydraulic fluid to and from the deployment head 302 in performing the above-described operations. For example, the handle assembly 306 can include a handle body 420, a lever assembly 422, and a syringe 424. In general terms, the handle body 420 maintains the lever assembly 422 and the syringe 424, with the syringe 424 containing a volume of hydraulic fluid 426. The lever assembly 422 is connected to the syringe 424, and controls the syringe 424 in dispensing and suctioning the hydraulic fluid 426 from and to the syringe 424.

The handle body 420 can have a wide variety of shapes or sizes conducive for handing by a user. Thus, while in the embodiment of FIG. 25 the handle body 420 has a pistol-like shape, other constructions are equally acceptable. With some configurations, however, the handle body 420 forms or provides a slot 430 adapted to interface with the lever assembly 422 as described below, and maintains the syringe 424 at an appropriate orientation and location for interaction with the lever assembly 422. The slot 430 is defined by a first segment 432 and a second segment 434. Paths defined by the segments 432, 434 differ, with the path of the first segment 432 corresponding with the arcuate pathways defined by the lever assembly 422.

The lever assembly 422 can also assume a wide variety of forms, and in some embodiments includes a primary lever arm 440, an engagement body 442, a first spring 444, a second spring 446, and a cam feature 448. The primary lever arm 440 and the engagement body 442 are pivotably mounted to the handle body 420. As described below, the engagement body 442 is configured to selectively interface with the syringe 424, with the springs 444, 446 biasing the engagement body 442 to desired positions during a deployment procedure. The cam feature 448 releasably couples and uncouples to the lever arm 440 and the engagement body 442 during, forced operation of the lever assembly 422.

The primary lever arm 440 can assume a wide variety of forms and is constructed for handling by a user. Thus, in some embodiments, the primary lever arm 440 includes or forms a grip 460 at a first end 462 thereof. A second end (hidden in FIG. 25) of the primary lever arm 440 is adapted for pivotable mounting to the handle body 420, such as via a pin 466.

The engagement body 442 includes first and second extensions 470, 472 that combine to define a gap 474 sized to receive a corresponding component of the syringe 424 as described below. In this regard, the extensions 470, 472 each form a contact surface 476, 478, respectively, adapted to interface with the corresponding syringe component. As shown, a length of the second extension 472 is greater than that of the first extension 470, with the second extension 472 further including a neck 480. As described below, a trailing surface 482 of the neck 480 is configured to interface with the cam feature 488 during operation of the lever assembly 422.

In addition to the above features, the engagement body 442 is configured for pivotable attachment to the handle body 420 at or adjacent a pivot end 484. For example, the pivot end 484 can be rotatably mounted to the pin 466. Further, the engagement body 442 forms a groove 486 sized to receive the second spring 446.

The cam feature 448 includes a pin 490 and a connector 492. The pin 490 is sized for slidable engagement within the slot 430 of the handle body 420, whereas the connector 492 extends from the pin 490 and is configured for pivotable mounting to the primary lever arm 440.

Finally, the syringe 424 can assume a variety of forms, and generally includes a tubular housing 494 and a piston 496. The housing 494 retains the hydraulic fluid 426, and is fluidly open at an open end 498. The piston 496 is slidably disposed within the housing 494, terminating at a head 500 as is known in the art.

Construction of the remote deployment handle assembly 306 includes positioning the syringe 424 within the handle body 420. The open end 498 is positioned to be accessible through the handle body 420, whereas the head 500 is positioned adjacent the slot 430. The lever assembly 422 is mounted to the handle body 420 by pivotably connecting the second end 464 of the primary lever arm 440 to the handle body 420, such as via the pin 466. Notably, the primary lever arm 440 is sized and positioned such that the primary lever arm 440 does not contact the head 500 of the syringe 424 with pivoting of the lever arm 440 at the second end 464. The engagement body 442 is similarly pivotably attached to the handle body 420, such as via the pin 466. As described below, positioning of the engagement body 442 is such that desired contact or interface with the syringe head 500 will occur during use.

The cam feature 468 is assembled such that the pin 490 is disposed within the slot 430, and the connector 492 is rotatably mounted to the primary lever arm 440. In this regard, the pin 490 is initially placed in the first segment 432 of the slot 430, and in contact with the trailing surface 482 of the neck 480 of the engagement body 442. With this construction, movement of the primary lever arm 440 (counterclockwise relative to the orientation of FIG. 25) is imparted onto the cam feature 448, that in turn transfers this motion onto the engagement body 442 via interface with the neck 480.

Finally, the first and second springs 444, 446 are assembled to the handle body 420 and placed into biased contact with the primary lever arm 440 and the engagement body 442, respectively, as shown. More particularly, the first spring 444 bears against the primary lever arm 440, biasing the primary lever arm 440 in counterclockwise direction (relative to FIG. 25); conversely, the second spring 446 bears against the engagement body 442 in a clockwise direction (relative to FIG. 25). Thus, when the primary lever arm 440 and the engagement body 442 are coupled to one another via the cam feature 448, forces of the springs 444, 446 essentially off-set one another. Conversely, once the coupling is removed, the first spring 444 freely biases the primary lever arm 440, and the second spring freely biases the engagement body 442.

During use, and commensurate with the above description relating to operation of the deployment head 302 (FIGS. 23A-23C) in deploying the clips 320 (FIG. 20C) the handle assembly 306 is first provided in the initial state of FIG. 25. In the initial state, the piston 496 is retracted relative to the syringe tube 494, such that the hydraulic fluid 426 is suctioned and retained within the housing 494. The lever arm 440 and the engagement body 442 are rotated to the position is shown, with the cam feature 448 interconnecting the lever arm 440 with the engagement body 442.

The hydraulic fluid 426 can be forcibly expelled from the syringe housing 494 by a user applying a forward (e.g., counterclockwise relative to the orientation of FIG. 25) force onto the lever arm 440, for example at the grip 460. Movement of the lever arm 440 is transferred to the cam feature 448, which in turn forces the engagement body 442 to rotate in a similar fashion. In this regard, the contact surface 478 of the second extension 472 contacts the head 500 of the syringe piston 496, thus forcing the piston 496 to move distally within the syringe housing 494. This motion, in turn, forces the hydraulic fluid 426 from the syringe 424. The first spring 444 assists in rotating or pivoting the primary lever arm 440, effectively counter-balancing a resistive force generated by the second spring 446.

Figure 26A:
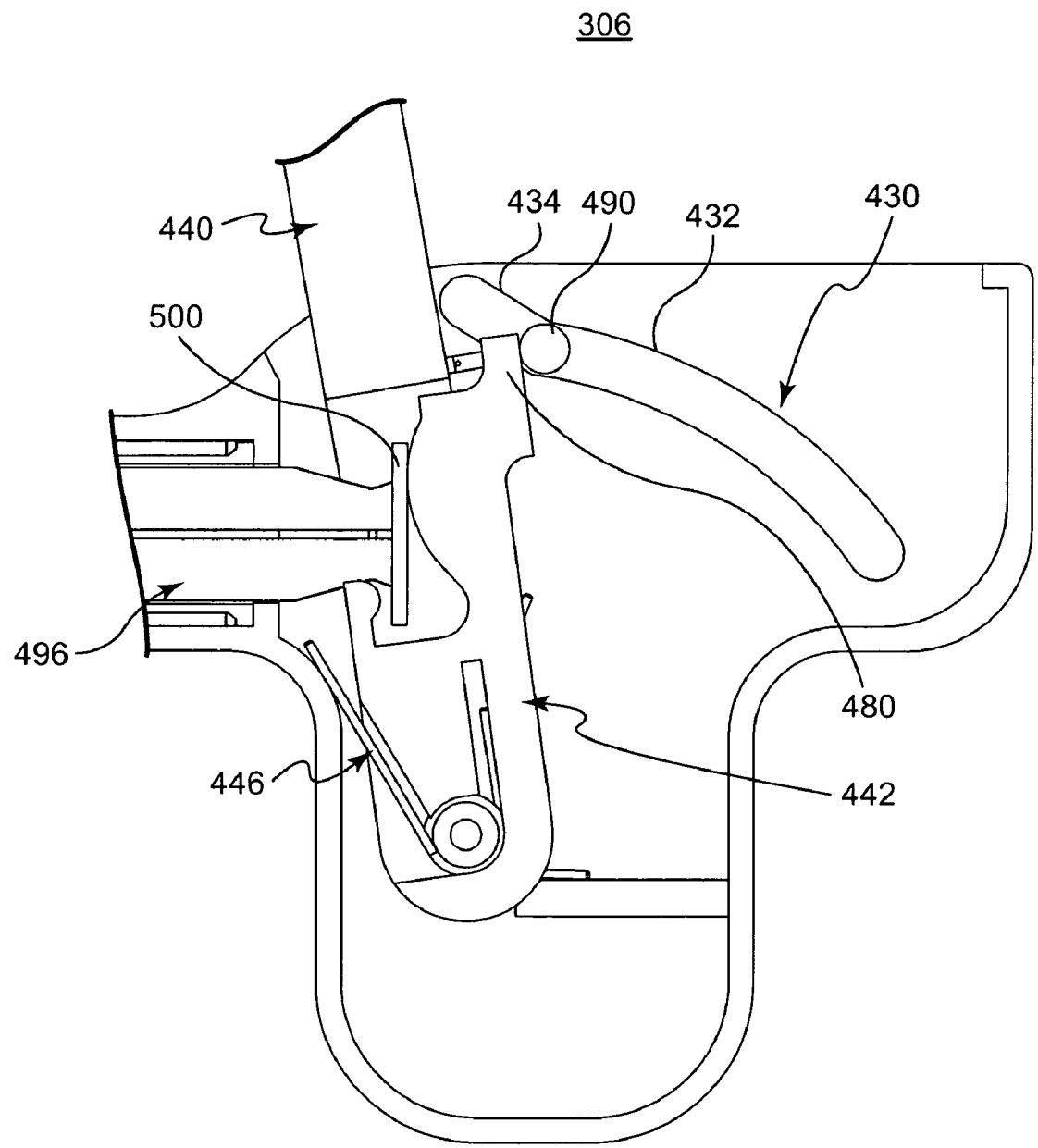
FIGS. 26A-26C illustrate operation of the remote handle assembly of FIG. 25.
Figure 26B:
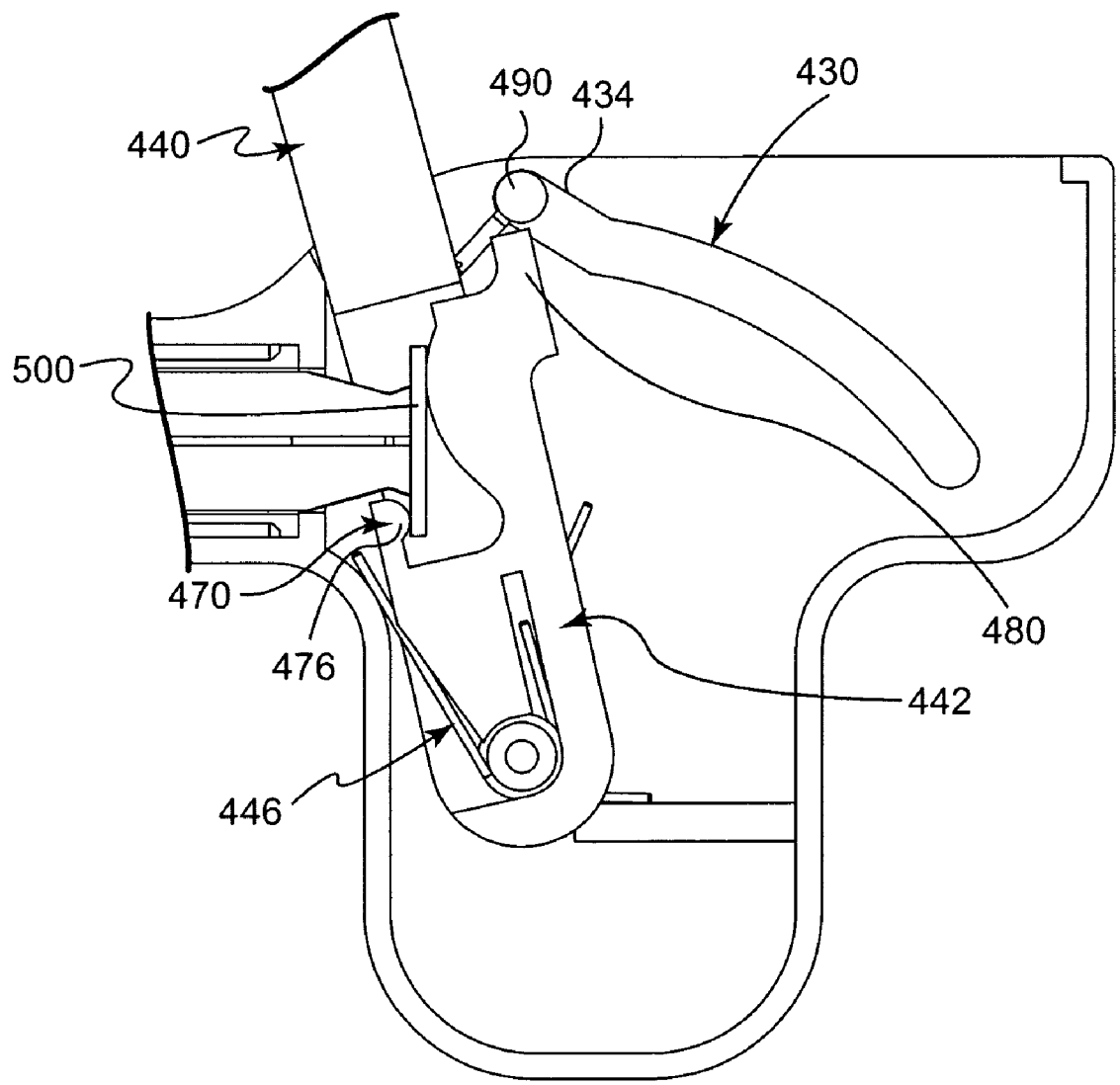

Coupling between the lever arm 440 and the engagement body 442 is maintained by the cam feature 448 throughout a majority of the above-described motion or movement of the primary lever arm 440. More particularly, as the lever arm 440 is pivoted forwardly, the pin 490 rides within the first segment 432 of the slot 430. Thus, and as shown in FIG. 26A, as the lever arm 440 is near an end of the forward motion, the pin 490 remains in intimate contact with the neck 480 of the engagement body 442. Upon reaching the second segment 434 of the slot 430, however, continued forward movement of the pin 490 along the slot 430 causes the pin 490 to disengage from the neck 480. For example, as the pin 490 progresses through the second segment 434 of the slot 430, the pin 490 is guided away from the neck 480. As shown in FIG. 26B, upon completion of a forward movement of the lever arm 440, the pin 490 is no longer in contact with the neck 480 such that the primary lever arm 440 is no longer coupled to the engagement body 442. This point of release generally correlates with a maximum desired forward position of the syringe piston 496. In other words, maximum hydraulic fluid displacement has occurred, thus applying maximum hydraulic pressure to the deployment head 302 (FIG. 23B). As previously described, this pressure state corresponds with distal movement of the transfer rods 316 (FIG. 23B) in connection with deployment of the clips 320 (FIG. 23B).

Figure 26C:
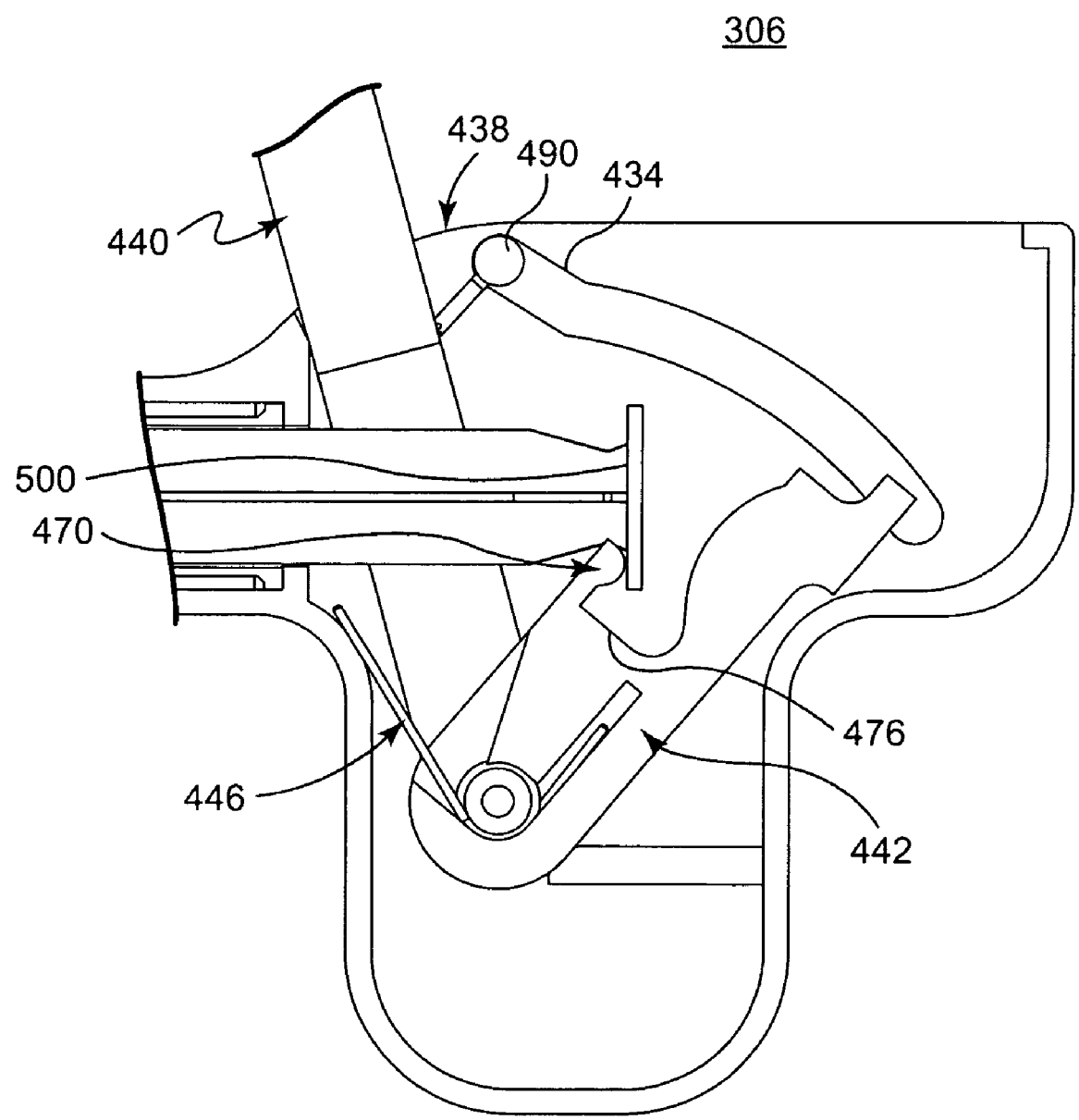

When the cam feature 448 is shifted away from a path of the engagement body 442, the second spring 446 freely forces or biases the engagement body 442 to rotate or pivot in a reverse fashion, returning to an initial position as shown in FIG. 26C. The primary lever arm 440 remains uncoupled from the engagement body 442. With this return, pivoting movement, the contact surface 476 of the first extension 470 interfaces with the head 500 of the syringe piston 496, causing the piston 496 to proximally retract relative to the syringe housing 494. Thus, a negative pressure condition is generated within the piston housing 494, suctioning or vacuuming the hydraulic fluid 426 (FIG. 25) from the deployment head 302 (FIG. 23C). As previously described, this action correlates with retraction of the hollow containment members 314a, 314b (FIG. 23C) in completing the clip deployment procedure.

Figure 27:
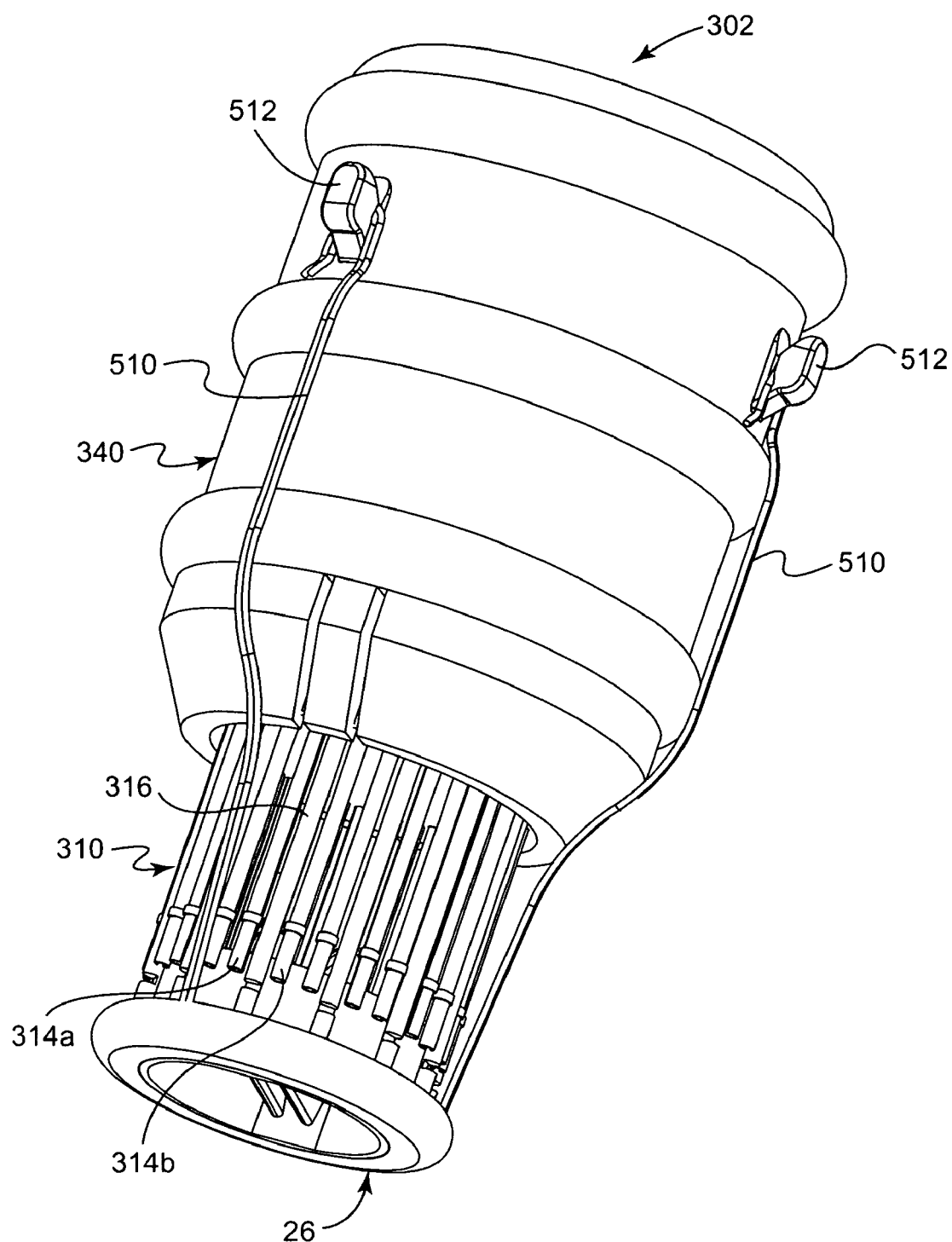
FIG. 27 is a perspective view of a replacement valve mounted to the deployment head of FIG. 19.

Returning to FIG. 18, use of the deployment device 300 in performing a surgical procedure, such as replacing a natural valve with a replacement prosthetic valve is akin to the procedures previously described with respect to the deployment device 22 (FIG. 1A). In general terms, and with additional reference to FIG. 27, the replacement valve 26 is preloaded onto the clip holding assemblies 310 (otherwise preloaded with the clips 320). As shown, the transfer rods 316 are fully retracted relative to the corresponding hollow containment members 314a, 314b. One or more sutures 510 can be employed to temporarily secure the replacement valve 26 to the deployment device 300. The sutures 510 are sewn through the replacement valve 26 and placed under tension. In this regard, the deployment head 302 can include one or more features for holding the temporary sutures 510. For example, the housing 340 can include or form exterior hooks 512 sized to selectively receive and retain the temporary sutures 510. Alternatively, the replacement valve 26 can be temporarily secured to the deployment device 300 in a wide variety of other manners.

Standard surgical sutures are then used to guide the device to the desired location (e.g., annulus of the native valve), followed by operation of the deployment device 300 to deploy the clips 320 (FIG. 20C) through the replacement valve 26 and the native anatomy (e.g., aortic wall). This operation can consist simply of the user applying a moment force onto the lever arm 440 (FIG. 25) as previously described. Regardless, the deployment head 302 is remotely operated to substantially simultaneously effectuate deployment of the clips 320 in a manner securing the replacement valve 26 to the native anatomy.

Figure 28A:
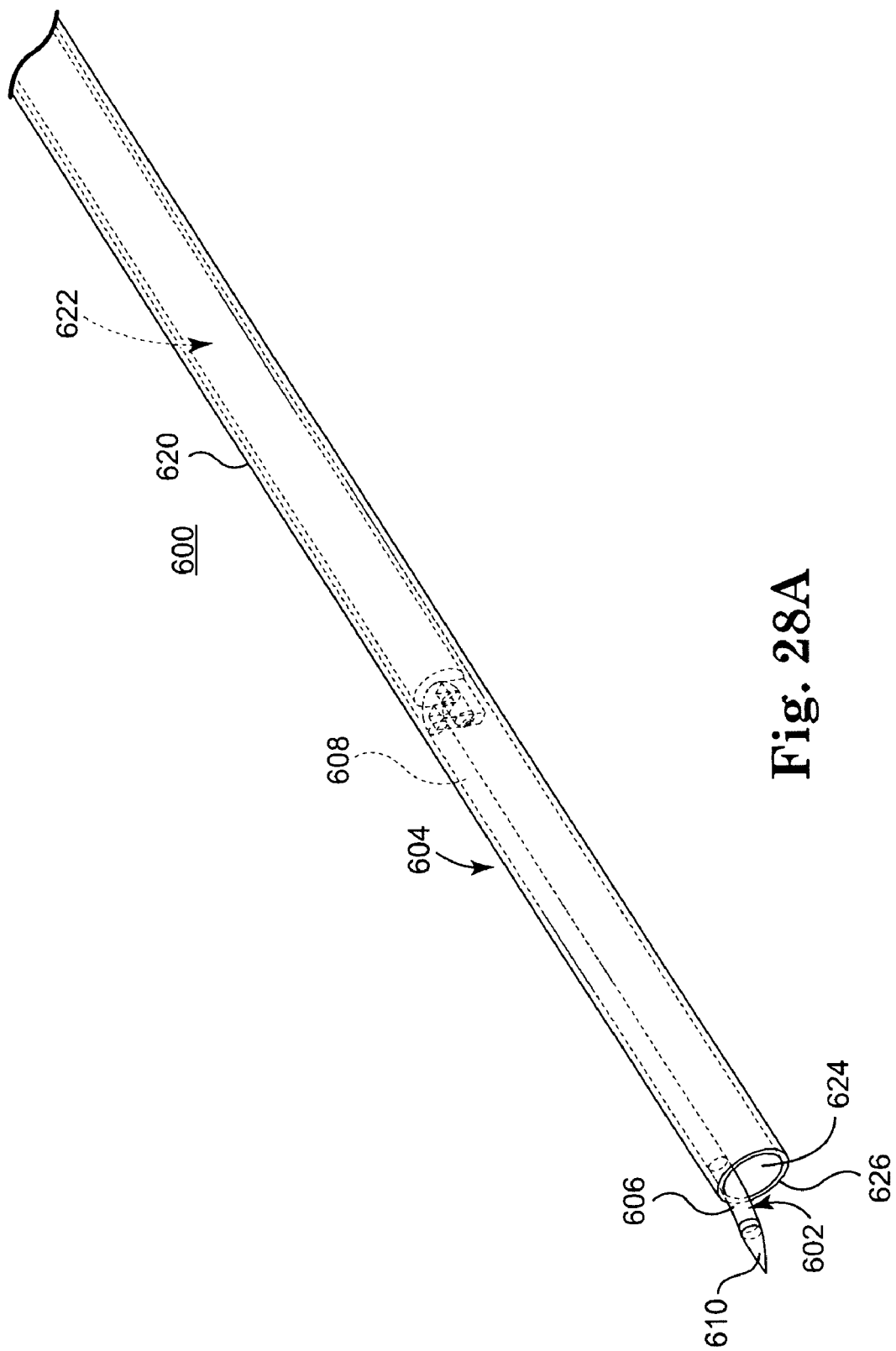
FIG. 28A illustrates a distal portion of another surgical fastening apparatus in accordance with the present disclosure and in a partially retracted state.
Figure 28B:
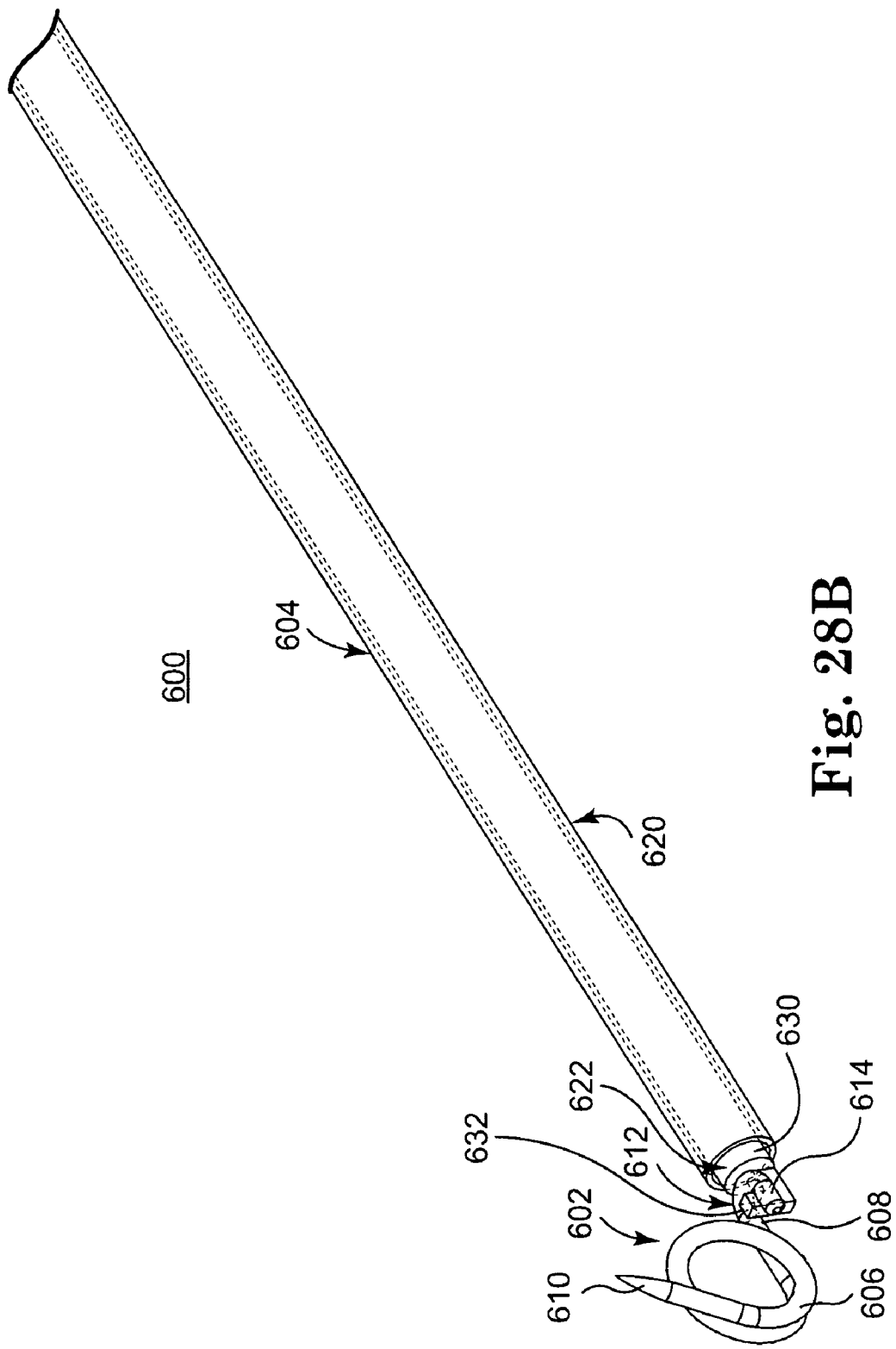
FIG. 28B illustrates the apparatus of FIG. 28A in a deployed state.

Referring to FIGS. 28A and 28B, a portion of another embodiment surgical fastening or prosthesis delivery apparatus 600 in accordance with the present disclosure is shown. In particular FIG. 28A illustrates an alternative surgical fastener or clip 602 and a corresponding clip holding assembly 604 in a partially retracted state, and FIG. 28B illustrates the apparatus 600 of FIG. 28A in a deployed state. In general terms, the clip 602 and the clip holding assembly 604 have only a single containment arm (as compared to the dual or double armed configurations described above). This single arm variation or arrangement is especially suitable for indications in which paravalvular leak is not a concern (i.e., annuloplasty ring placement). In this variation, the double arm clip 24 (FIG. 9) is replaced with the single arm clip 602, and the clip holding assembly 604 is modified.

The clip 602 is formed to exhibit the shape memory characteristics described above (e.g., Nitinol wire), naturally self-reverting from the straightened state of FIG. 28A to the curved or looped state of FIG. 28B. The clip 602 has or defines opposing, first and second end segments 606, 608. The first end segment 606 can terminate at a sharpened end 610 as shown. The second end segment 608 forms, in some embodiments, an engagement feature 612, for example a lateral hook 614. As described below, the engagement feature 612 facilitates releasable connection with the clip holding assembly 604.

The clip holding assembly 604 includes a hollow containment arm 620 and a transfer rod 622. The hollow containment arm 620 is akin to the hollow containment arm 90 (FIG. 1A) described above and forms a lumen 624 sized to slidably receive the transfer rod 622 and the clip 602. The lumen 624 is open at a distal end 626 of the hollow containment arm 620, and the distal end 626 may or may not be sharpened as previously described.

The transfer rod 622 is akin to the transfer rod 92 (FIG. 9) previously described, and can be solid or tubular. Regardless, the transfer rod 622 terminate at a distal end segment 630 adapted to selectively engage the clip 602. For example, the distal end segment 630 can include or form an engagement finger 632 sized to receive the lateral hook 614 of the clip 602. Alternatively, a wide variety of other connection techniques or components are also acceptable.

The clip 602 is loaded to the clip holding assembly 204 by first distally extending the transfer rod 622 relative to the containment arm 620 such that the distal end segment 630 is distal the distal end 626 of the containment arm 620. For example, the delivery apparatus 600 can include various retractor and/or control device(s) maintaining proximal ends of the containment arm 620 and the transfer rod 622 akin to the control devices 94, 96 (FIG. 1A) as previously described.

With the distal end segment 630 exposed, the clip 602 is connected to the transfer rod 622. With the one configuration of FIGS. 28A and 28B, the lateral hook 614 of the clip 602 is partially captured by the engagement finger 632 as shown in FIG. 28B. The transfer rod 622 is then proximally retracted relative to the hollow containment arm 620, thus pulling the clip 602 within the lumen 624 via engagement with the transfer rod 622. Proximal retraction continues until the clip 602 is completely or nearly completely within the lumen 624 as shown in FIG. 28A. Notably, as the clip 602 bears against the hollow containment arm 620 with proximal retraction of the transfer rod 622, the hollow containment arm 620 forces the clip 602 to a more straightened state as shown.

Deployment of the clip 602 from the clip holding assembly 604 is accomplished in a reverse manner. The transfer rod 622 is distally advanced relative to the hollow containment arm 620, thus forcing the clip 602 distally along the lumen 624 and through the distal end 626. As the clip 602 extends beyond the distal end 620, the clip self-reverts to the curled or looped shape (i.e., transitions from the shape of FIG. 28A to the shape of FIG. 28B). This rapid change in state/shape causes the engagement feature 612 of the clip 602 to automatically release from the distal end segment 630 of the transfer rod 622 (e.g., the lateral hook 614 dislodges from the engagement finger 632). Alternatively, the clip holding assembly 604 can include an additional feature and/or mechanism to assist in releasing the clip 602 and/or the clip holding assembly 604 can be maneuvered away from the now deployed clip 602.

Although the foregoing method has been described in connection with open chest surgery, the leaflets can be removed and prosthesis delivery apparatus described herein can be used with minimally invasive approaches that typically require a thoracotomy between adjacent ribs.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto.

What is claimed is:

1. A surgical fastening apparatus comprising:
    at least one self-closing clip comprising a wire defining an intermediate portion interconnecting opposing, first and second side portions, the side portions each having a memory set loop shape; and
    a deployment device comprising:
        at least one clip holding assembly for selectively retaining and deploying the clip, the clip holding assembly including:
            first and second hollow containment arms each forming a distal segment defining a lumen extending from an open, distal end, wherein the containment arms are arranged in a side-by-side fashion,
            a first transfer rod associated with at least one of the containment arms in an axially movable fashion relative to a longitudinal axis of the at least one containment arm, wherein a distal region of the transfer rod forms an engagement feature,
            an actuator connected to the transfer rod for controlling movement of the transfer rod relative to the containment arms;
        wherein upon final assembly in a pre-deployment state, the engagement feature of the transfer rod engages the intermediate portion of the clip, and the first and second side portions of the clip are captured by the distal segments of the first and second containment arms;
        and further wherein the deployment device is configured such that upon actuation of the actuator, the transfer rod extends distally relative to the containment arms in transitioning to a deployment state in which the first and second side portions of the clip extend distally beyond the distal end of the first and second containment arms, respectively.

2. The fastening apparatus of claim 1, wherein the containment arms each form a side aperture extending from the distal end and open to the corresponding lumen, the aperture sized to slidably receive the intermediate portion of the clip.

3. The fastening apparatus of claim 2, wherein upon final assembly, the aperture of the first containment arm faces the second containment arm, and the aperture of the second containment arm faces the first containment arm.

4. The fastening apparatus of claim 1, wherein the first transfer rod is slidably disposed within the first containment arm, the clip holding assembly further comprising:
    a second transfer rod slidably disposed within the second containment arm.

5. The fastening apparatus of claim 4, wherein the engagement feature of each of the transfer rods includes a tubular body forming a passage sized to receive a respective one of the side portions of the clip, and an axial slot formed in the tubular body and providing exterior access to the passage.

6. The fastening apparatus of claim 5, wherein the engagement feature further includes a notch formed contiguous with the slot and sized to receive the intermediate portion of the clip.

7. The fastening apparatus of claim 6, wherein upon final assembly, the notch of the first transfer rod is circumferentially aligned with the aperture of the first containment arm such that upon final assembly in the pre-deployment state, the first side portion of the clip is disposed within the passage of the first transfer rod and the lumen of the first containment arm, and the intermediate portion of the clip extends from the first containment arm via the notch of the first transfer rod and the aperture of the first containment arm.

8. The fastening apparatus of claim 4, wherein the clip holding assembly further comprises:
   a shaft interconnecting the first and second transfer rods; and
   a conduit from which the containment arms distally extend;
   wherein the shaft is slidably disposed within the conduit.

9. The fastening apparatus of claim 1, wherein the transfer rod is disposed between the first and second containment arms.

10. The fastening apparatus of claim 1, wherein the fastening apparatus includes a plurality of the clips and the deployment device includes a plurality of the clip holding assemblies selectively retaining respective ones of the clips.

11. The fastening apparatus of claim 10, wherein the clip holding assemblies are arranged in a circumferential manner relative to one another.

12. The fastening apparatus of claim 11, wherein the deployment device further comprises:
   a valve sizing rod disposed within the circumferentially arranged clip holding assemblies, the valve sizing rod configured to selectively alter a diameter collectively defined by the clip holding assemblies.

13. The fastening apparatus of claim 11, wherein the deployment device further comprises:
   a plurality of valve holding mechanisms associated with the plurality of clip holding assemblies.

14. The fastening apparatus of claim 13, wherein the valve holding mechanisms each include a holding member slidably disposed within a hollow cylinder.

15. The fastening apparatus of claim 14, wherein a distal region of each of the holding members has a memory set curve shape and terminates at sharpened, distal end.

16. The fastening apparatus of claim 14, wherein respective ones of the valve holding mechanisms are circumferentially interposed between the clip holding assemblies.

17. The fastening apparatus of claim 10, wherein the actuator includes a first control device connected to the transfer rods and a second control device connected to the containment arms of each of the plurality of clip holding assemblies, and further wherein the deployment device is constructed such that the first control member is slidable relative to the second control member in effectuating substantially simultaneous deployment of the clips.

18. The fastening apparatus of claim 10, wherein the actuator includes a source of hydraulic fluid remotely connected to the clip holding assemblies via tubing.

19. The fastening apparatus of claim 1, wherein the actuator includes opposing handle bodies each connected to a corresponding lever, and further wherein the levers are connected to the transfer rod.

* * * * *